(12) United States Patent
Kimura et al.

(10) Patent No.: US 8,480,685 B2
(45) Date of Patent: Jul. 9, 2013

(54) ENDO-THERAPY PRODUCT SYSTEM AND CARTRIDGE INCLUDING TREATMENT DEVICE

(75) Inventors: Koh Kimura, Tokyo (JP); Ken Fujisaki, Tokyo (JP)

(73) Assignees: Olympus Corporation (JP); Olympus Medical Systems Corp. (JP)

( * ) Notice: Subject to any disclaimer, the term of this patent is extended or adjusted under 35 U.S.C. 154(b) by 1543 days.

(21) Appl. No.: 11/554,465

(22) Filed: Oct. 30, 2006

(65) Prior Publication Data
US 2007/0112359 A1 May 17, 2007

Related U.S. Application Data

(63) Continuation of application No. PCT/JP2005/022010, filed on Nov. 30, 2005.

(30) Foreign Application Priority Data

Dec. 7, 2004 (JP) .................................. 2004-354618

(51) Int. Cl.
*A61B 17/10* (2006.01)
(52) U.S. Cl.
USPC ........................................................ 606/139
(58) Field of Classification Search
USPC .................. 606/139, 142, 143, 151, 157, 213, 606/219, 108, 138, 158; 623/23.72; 227/175.1, 227/176.1; 206/210, 338, 340, 438
See application file for complete search history.

(56) References Cited

U.S. PATENT DOCUMENTS

| 4,146,130 | A | 3/1979 | Samuels et al. | |
| 4,936,447 | A | 6/1990 | Peiffer | |
| 6,460,700 | B2 * | 10/2002 | Weisshaupt | 206/339 |
| 6,814,742 | B2 * | 11/2004 | Kimura et al. | 606/151 |
| 7,452,368 | B2 * | 11/2008 | Liberatore et al. | 606/220 |

FOREIGN PATENT DOCUMENTS

| JP | 2002-191609 | 7/2002 |
| JP | 2004-73646 | 3/2004 |

OTHER PUBLICATIONS

International Preliminary Report on Patentability in corresponding PCT Appln. No. PCT/JP2005/022010 dated Jun. 21, 2007.
International Search Report dated Feb. 28, 2006.

* cited by examiner

*Primary Examiner* — Melanie Tyson
(74) *Attorney, Agent, or Firm* — Ostrolenk Faber LLP

(57) ABSTRACT

An endo-therapy product system includes an introduction device led into a body cavity, a treatment device and a cartridge. The cartridge includes a treatment device accommodating portion in which the treatment device is accommodated. The treatment device accommodating portion includes a coupling member accommodating portion which accommodates a coupling member of the treatment device and a treatment device main body accommodating portion which accommodates a treatment device main body. The coupling member accommodating portion prevents a connecting portion of the introduction device from being engaged with an engagement portion at a proximal end of the coupling member. The treatment device main body accommodating portion is provided on a distal end side of the coupling member accommodating portion, has the treatment device main body arranged therein, and includes an engagement allowing portion which allows engagement when engaging the connecting portion of the introduction device with the engagement portion of the coupling member.

17 Claims, 29 Drawing Sheets

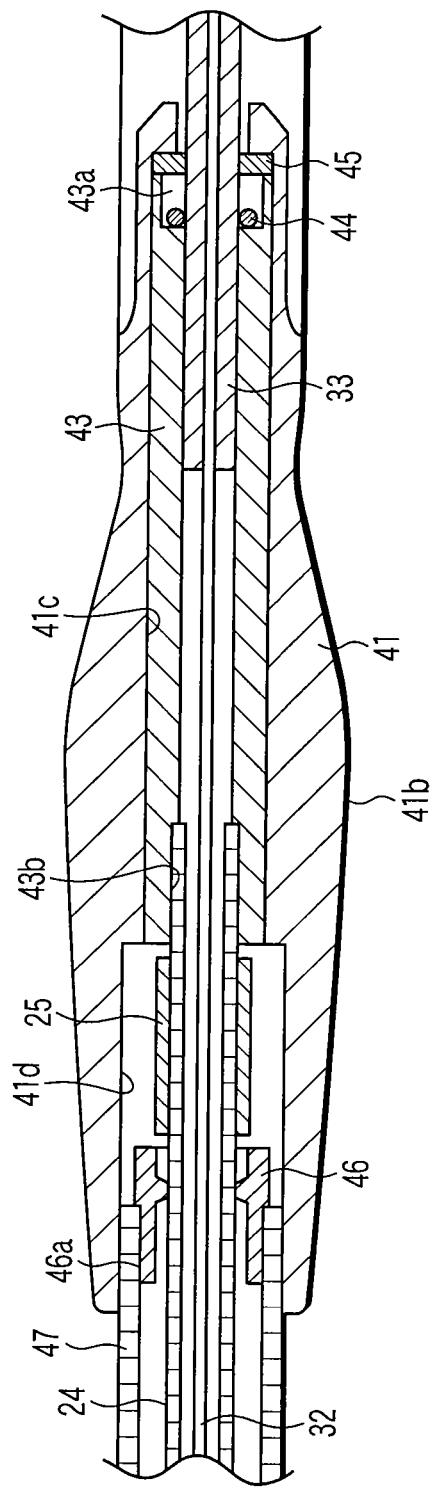
F I G. 3

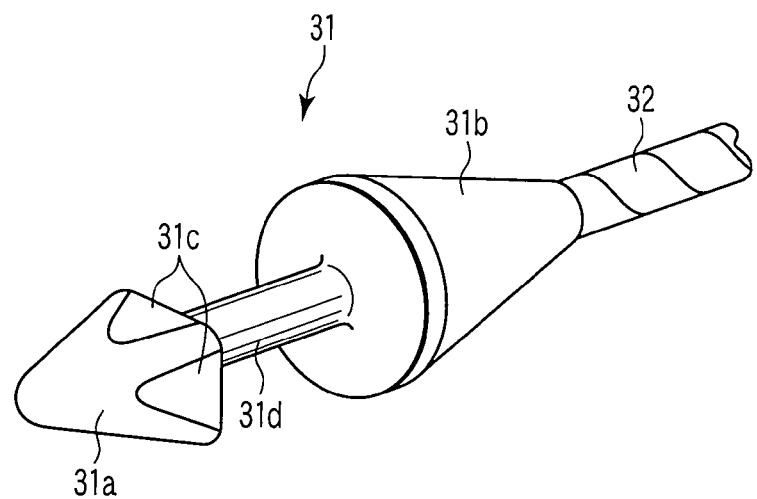
F I G. 4
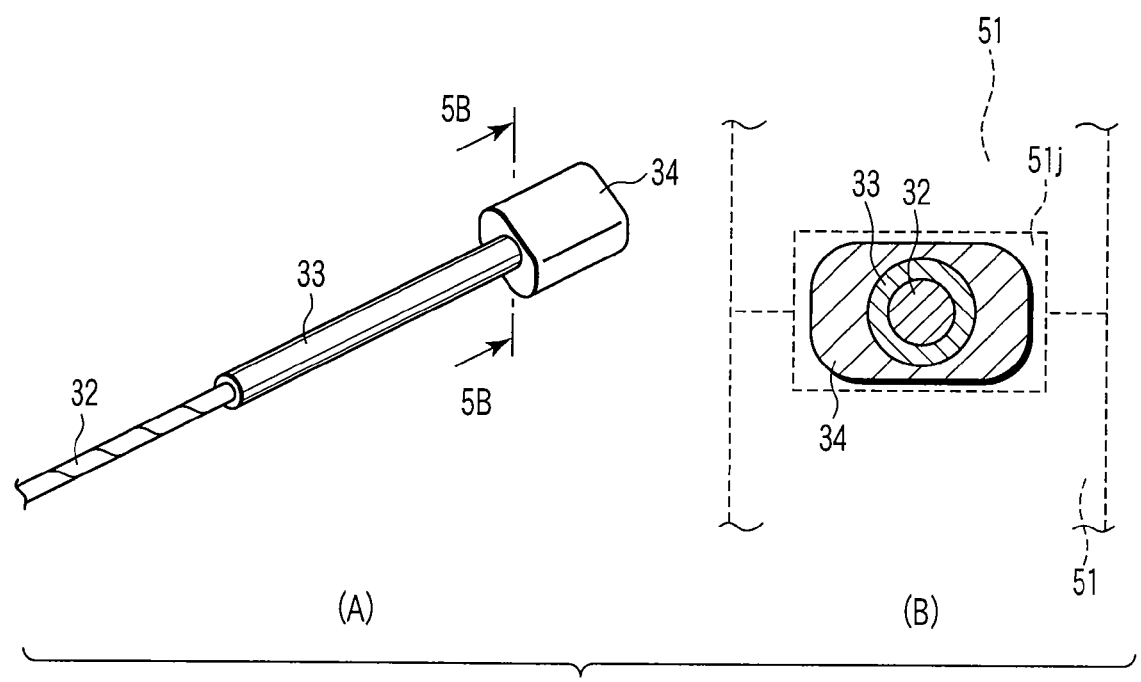
F I G. 5

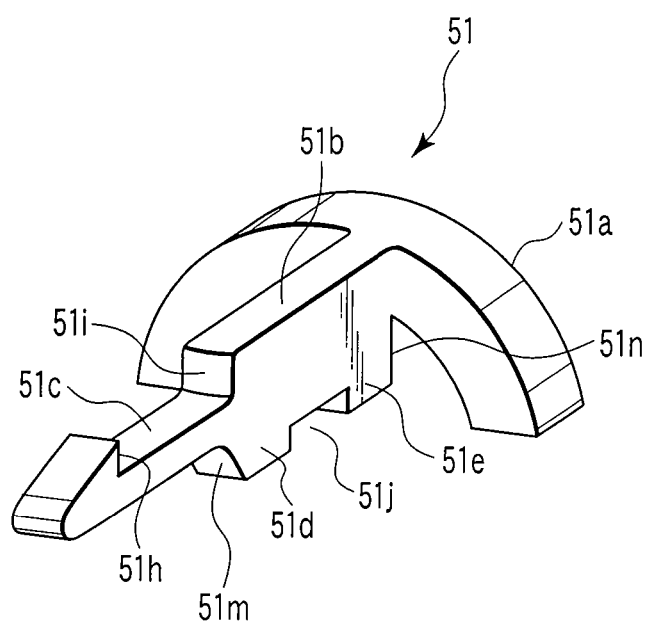
F I G. 6

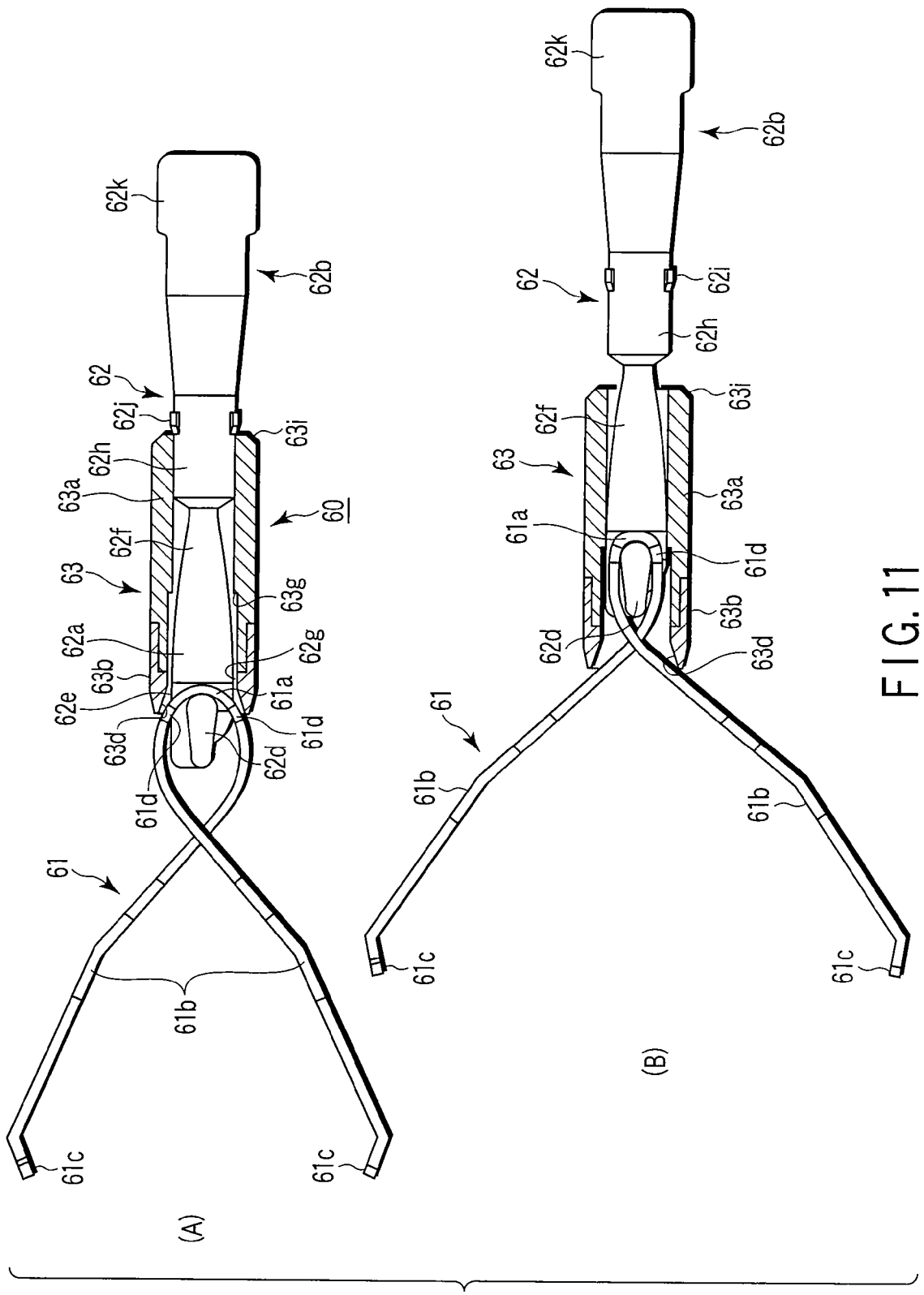
F I G. 11

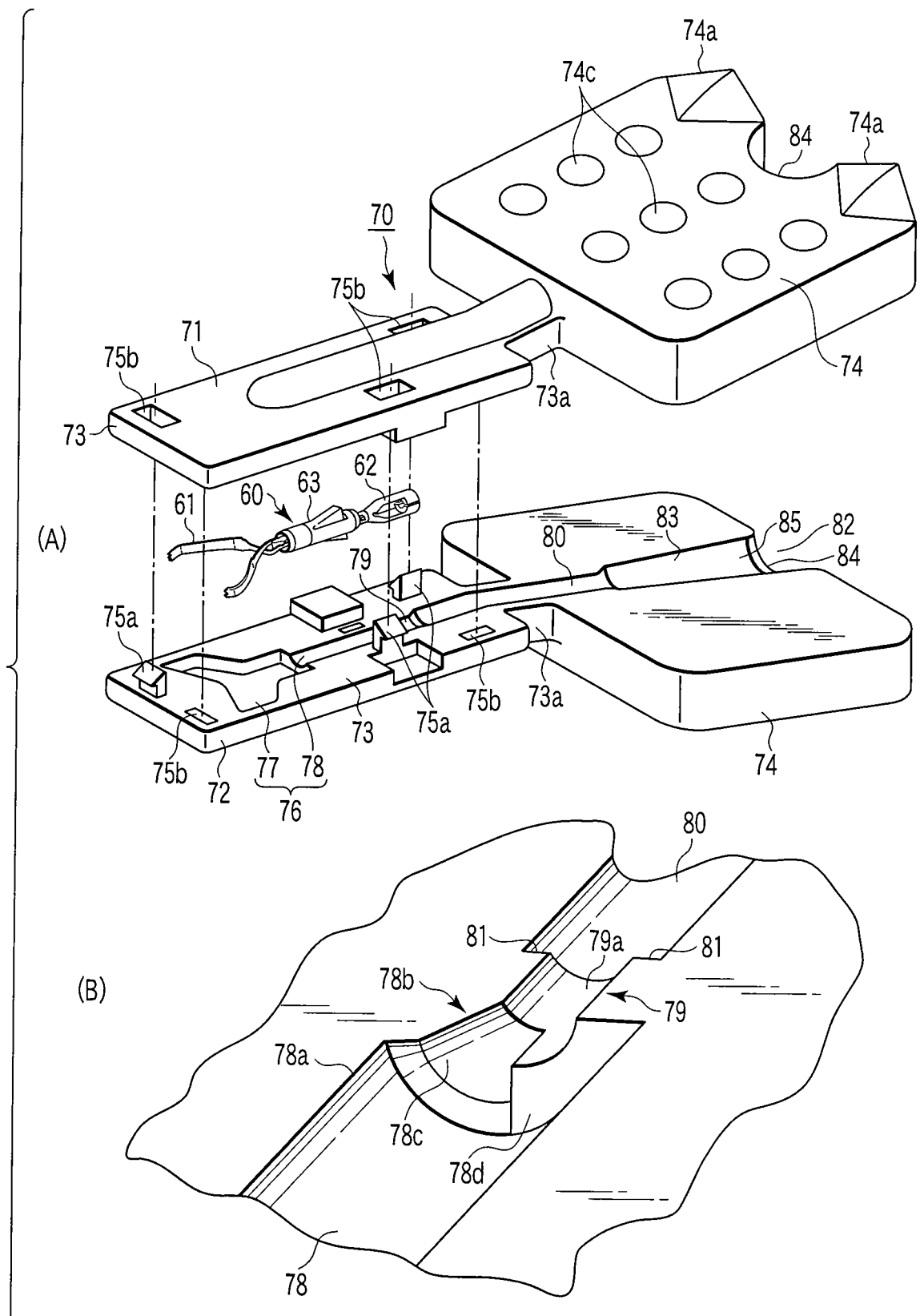
F I G. 12

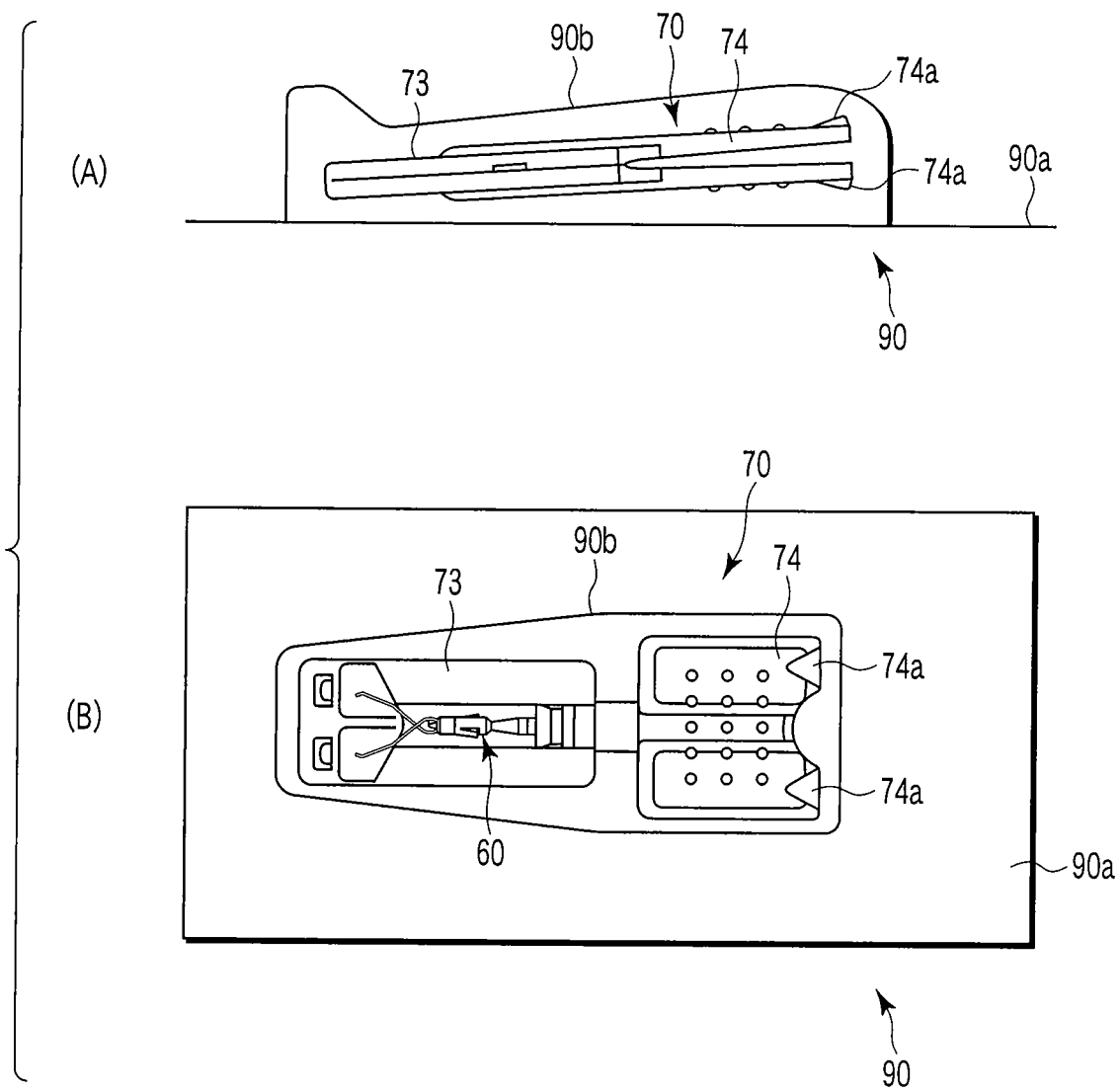
F I G. 14

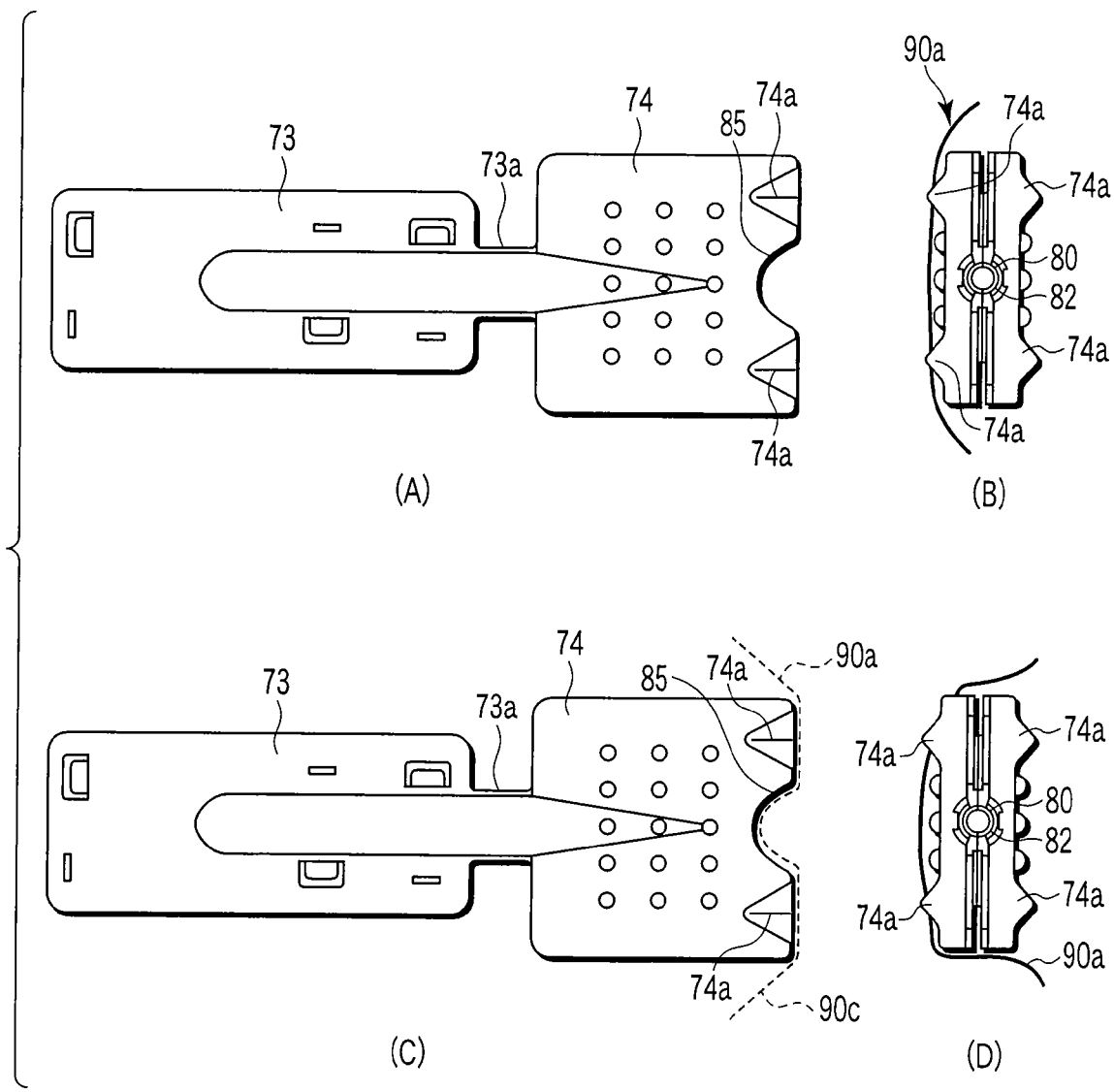
F I G. 15

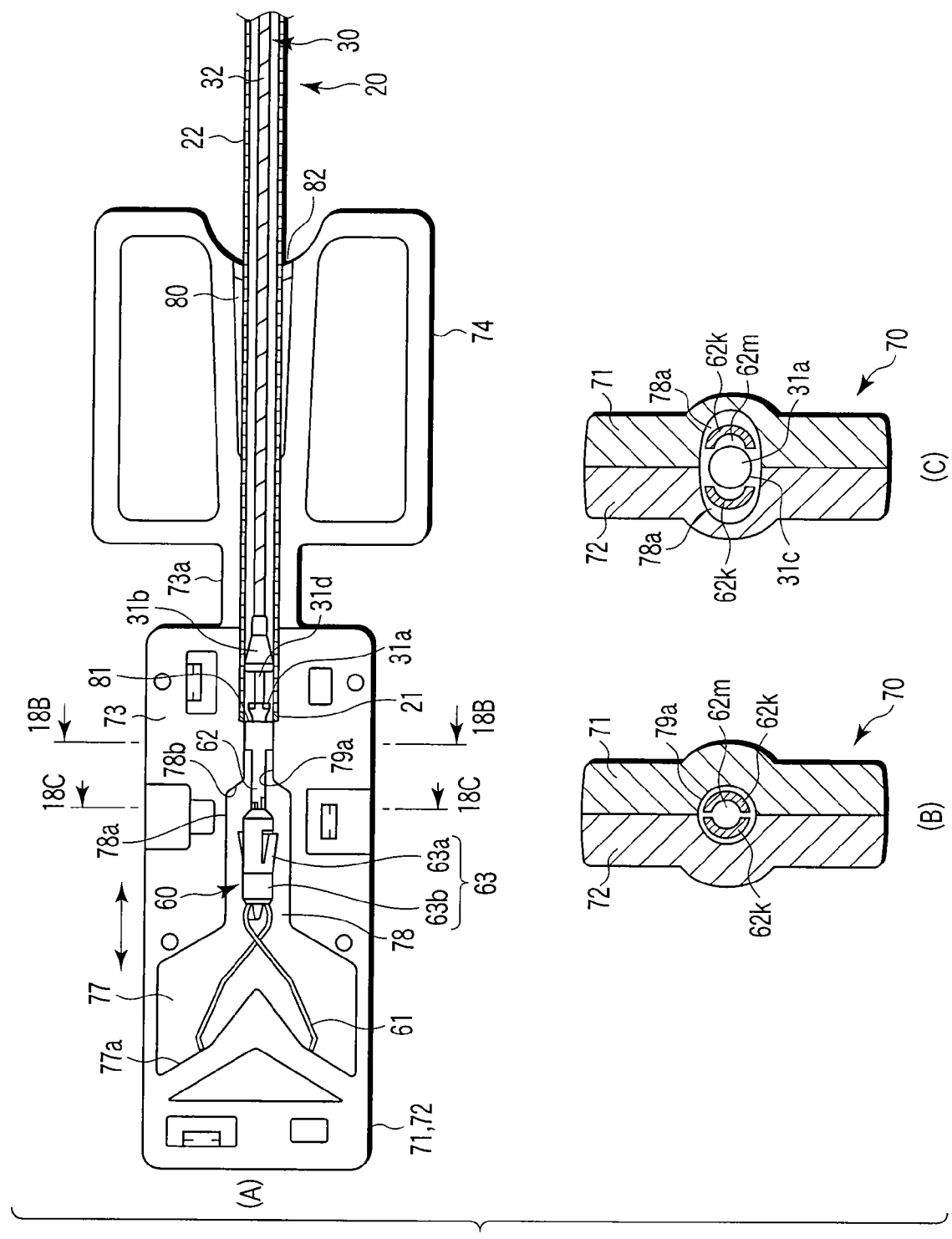
F I G. 18

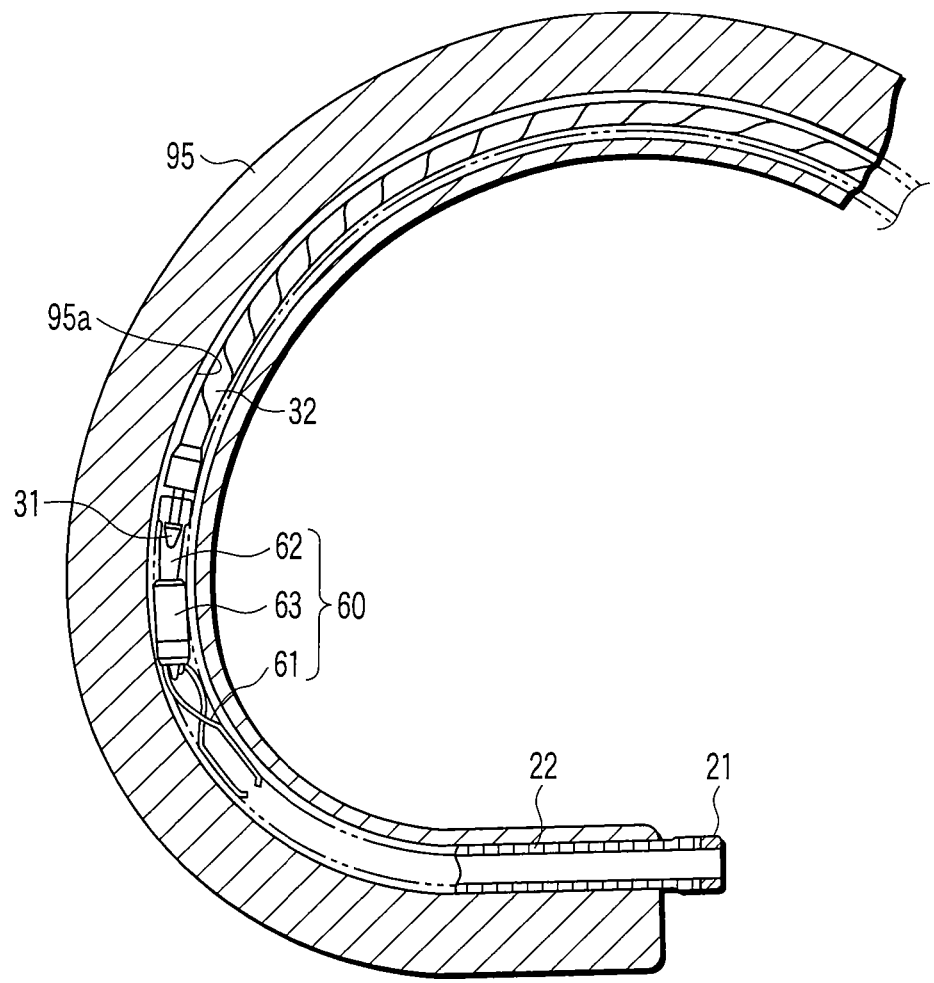
F I G. 20

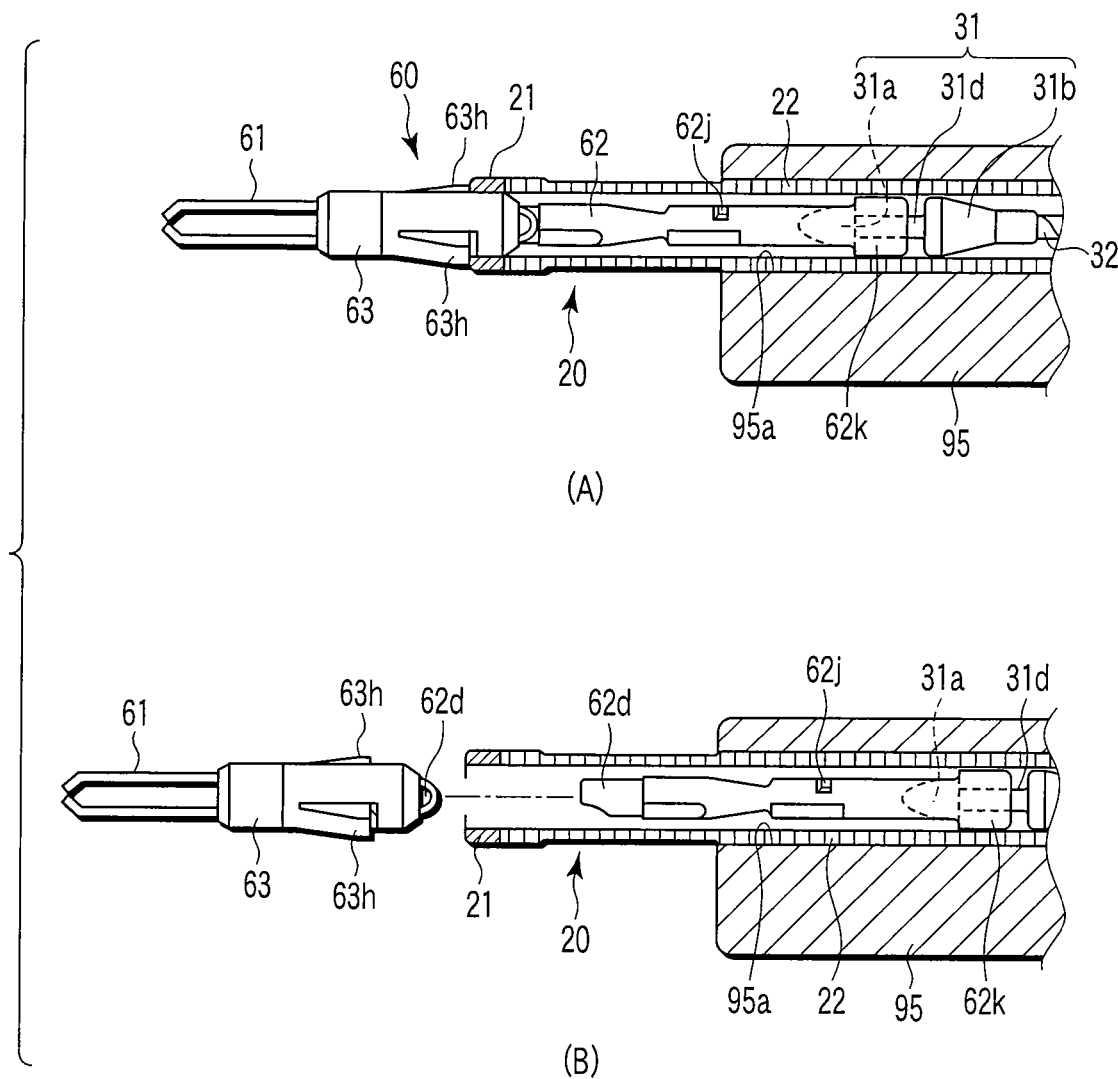
F I G. 23

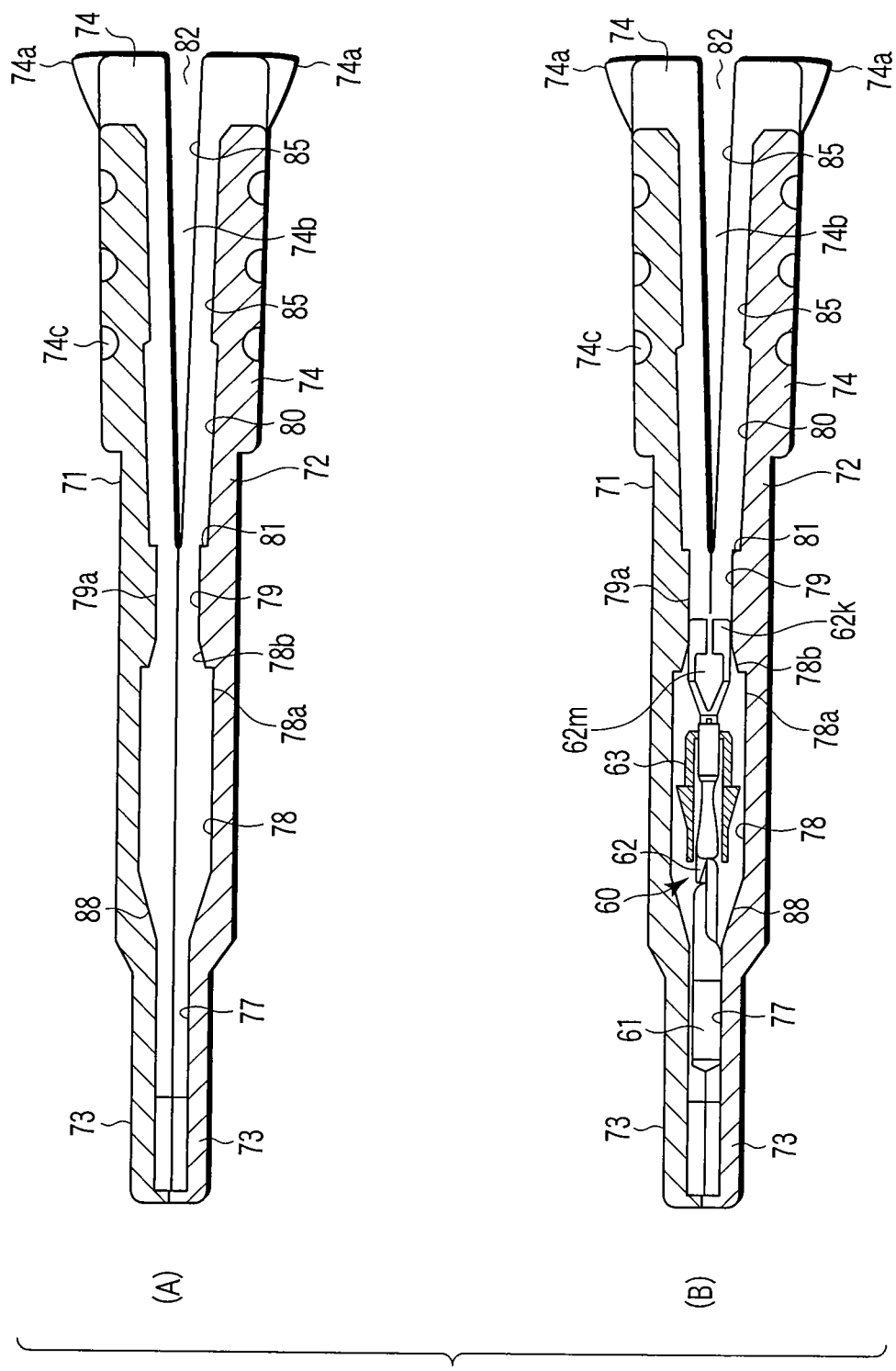
F I G. 27

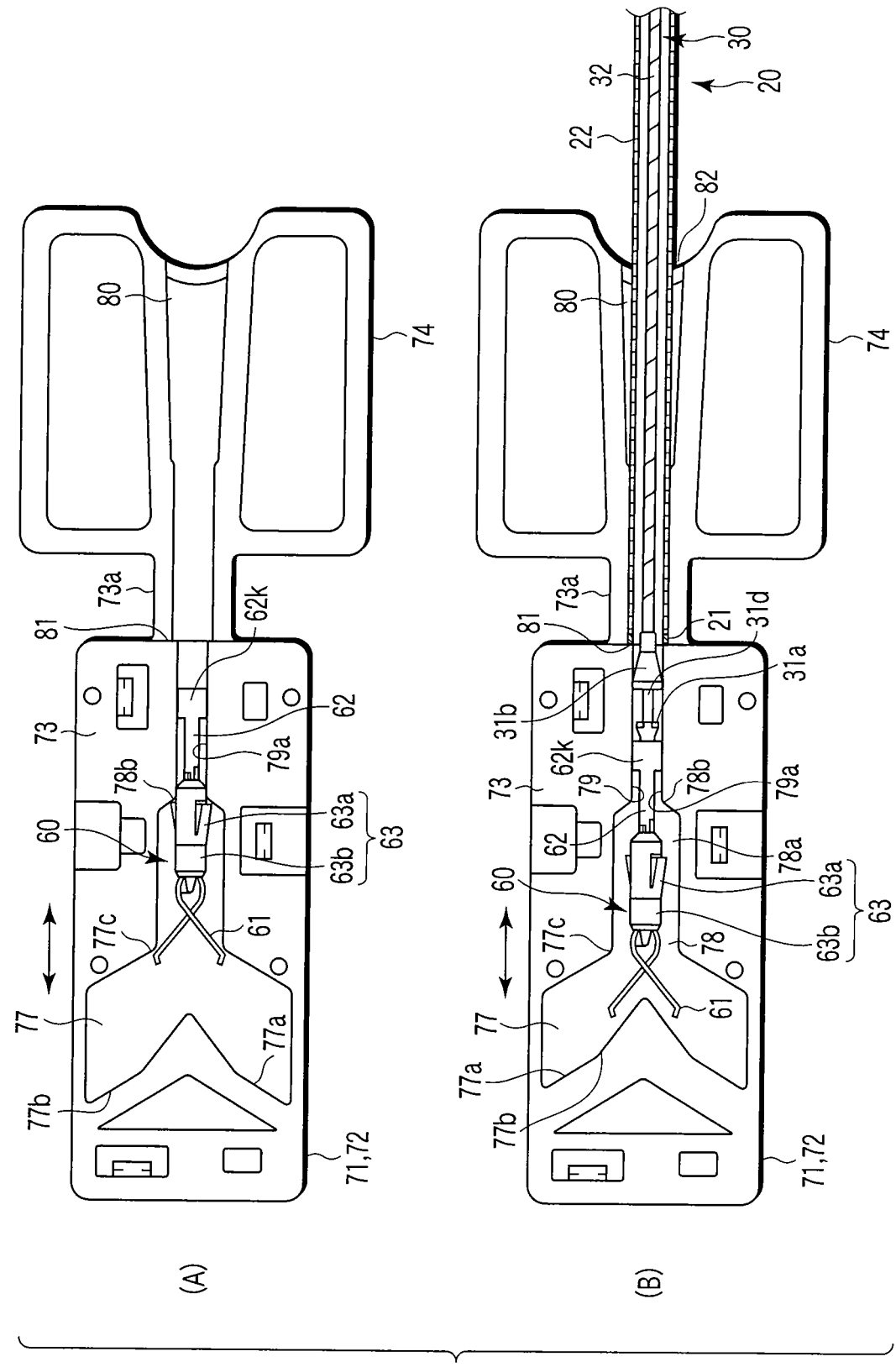
F I G. 28

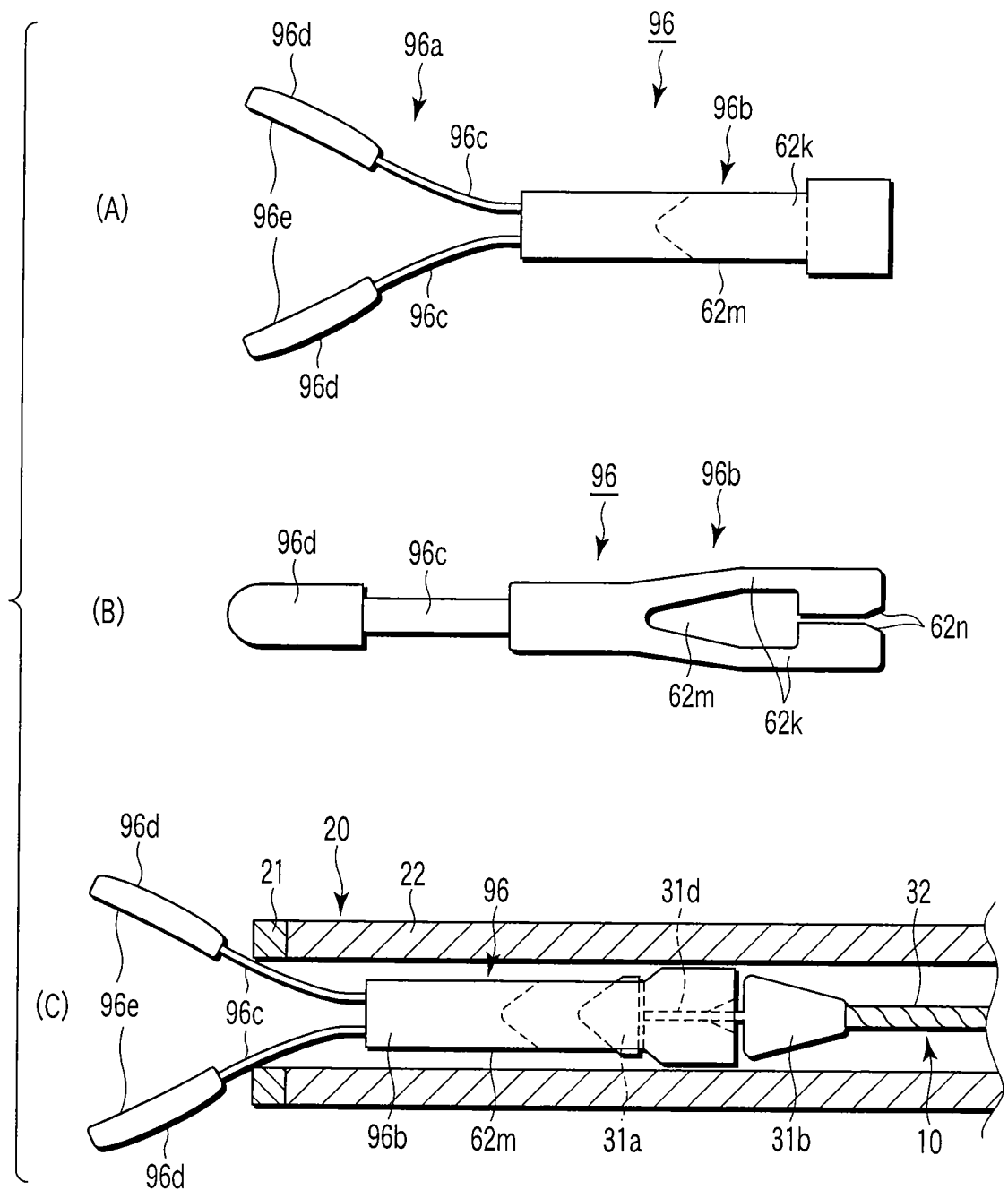
F I G. 30

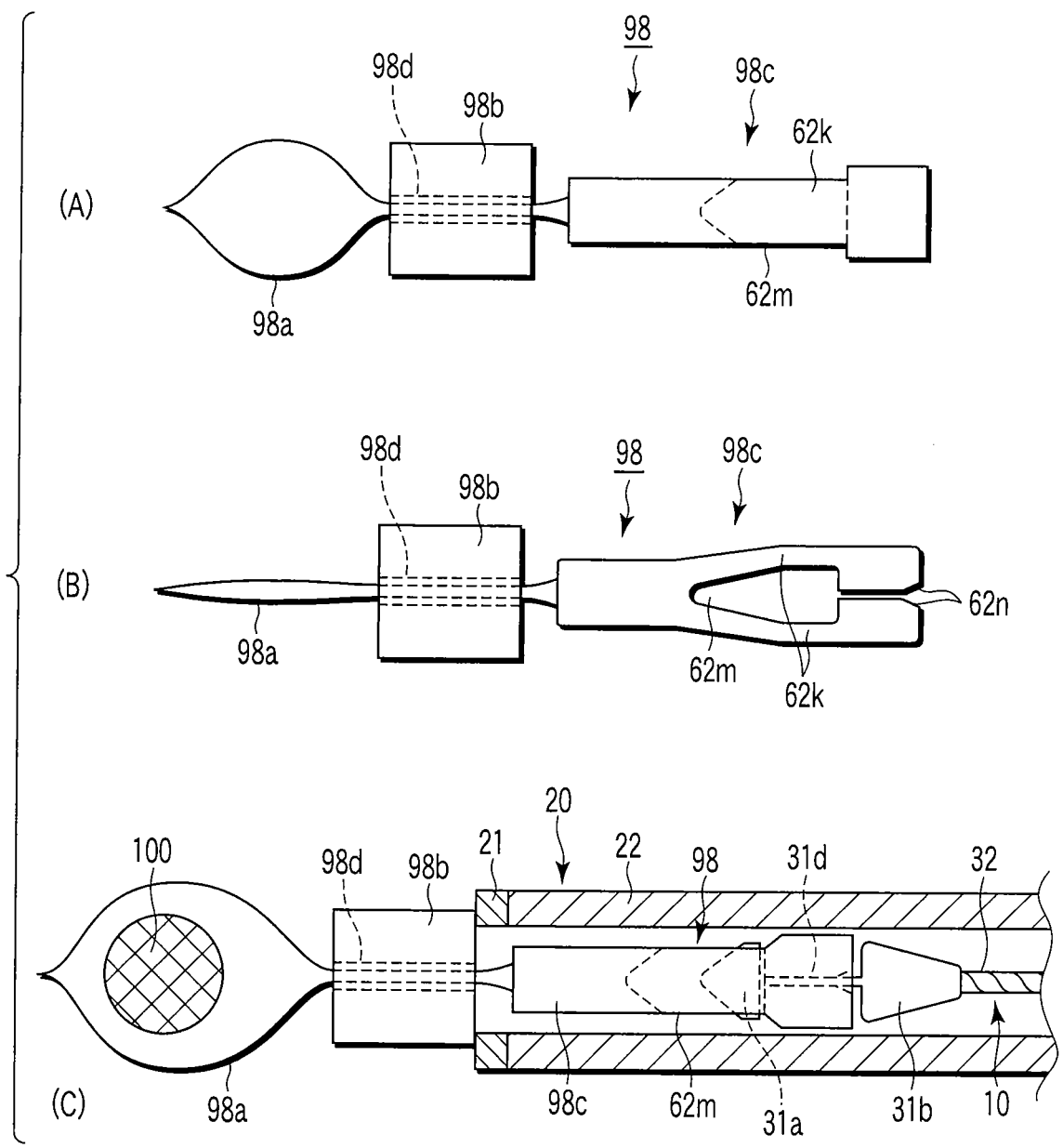
F I G. 31

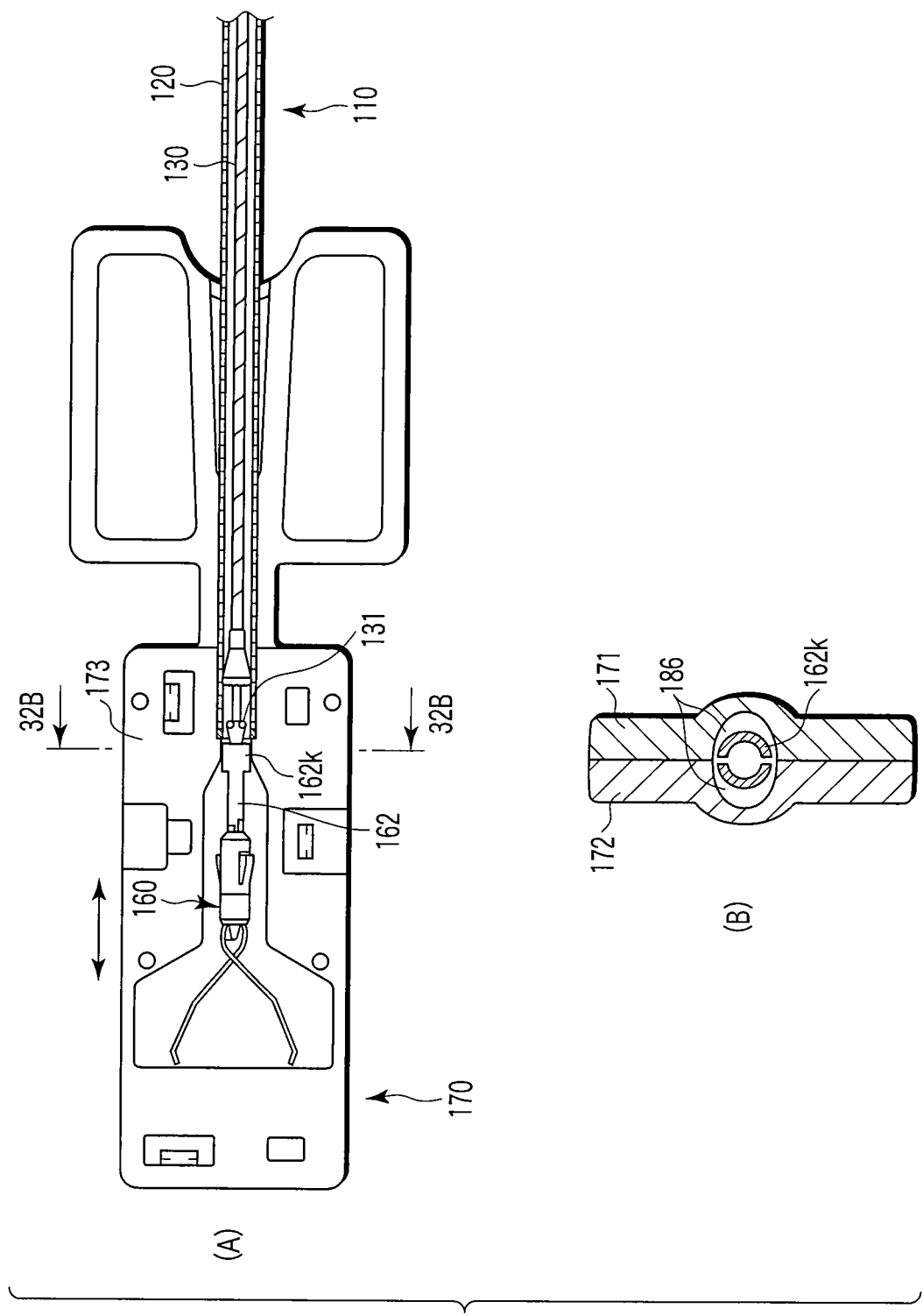
F I G. 32

ENDO-THERAPY PRODUCT SYSTEM AND CARTRIDGE INCLUDING TREATMENT DEVICE

CROSS-REFERENCE TO RELATED APPLICATIONS

This is a Continuation Application of PCT Application No. PCT/JP2005/022010, filed Nov. 30, 2005, which was published under PCT Article 21(2) in Japanese.

This application is based upon and claims the benefit of priority from prior Japanese Patent Application No. 2004-354618, filed Dec. 7, 2004, the entire contents of which are incorporated herein by reference.

BACKGROUND OF THE INVENTION

1. Field of the Invention

The present invention relates to an endo-therapy product system used together with an endoscope having a flexible inserting section, e.g., a bioptome or a clip introduction device, and a cartridge including a treatment device.

2. Description of the Related Art

For example, Jpn. Pat. Appln. KOKAI Publication No. 2002-191609 and Jpn. Pat. Appln. KOKAI Publication No. 2004-73646 disclose a clip introduction device (an introduction device), a clip unit (a treatment device) and a cartridge. As shown in FIGS. 32(A) and 32(B), a clip unit 160 included in a cartridge 170 having an upper case 171 and a lower case 172 can be connected with a clip introduction device 110. This introduction device 110 is provided with an introduction tube 120 and a wire member 130 which is retractable in a bore of this introduction tube 120 along an axial direction thereof. A hook portion (a connecting portion) 131 at a distant end of this wire member 130 can be engaged with an elastically deformable elastic arm portion 162k at a proximal end of the clip unit 160.

In this case, as shown in FIG. 32(B), a space 186 in which the elastic arm portion 162k can be expanded is formed at a proximal end of a clip unit accommodating portion 173 of the cartridge 170. Therefore, as shown in FIG. 32(A), when the hook portion 131 is brought into contact with a proximal end of the elastic arm portion 162k, the elastic arm portion 162k is opened and the hook portion 131 is held in the elastic arm portion 162k.

BRIEF SUMMARY OF THE INVENTION

According to one aspect of the present invention, an endo-therapy product system is provided with an introduction device, a treatment device and a cartridge. The introduction device has a tubular body which can be inserted into a channel of an endoscope, a wire which is movably inserted into a bore of this tubular body along an axial direction of the tubular body, and a connecting portion which is arranged at a distant end of this wire and retractable with respect to the distal end of the tubular body by movement of the wire. The treatment device has a coupling member having an engagement portion which can be engaged with the connecting portion at a proximal end, and a treatment device main body detachably provided at a distal end of the coupling member. The cartridge accommodates the treatment device and is used when engaging the connecting portion with the engagement portion. The cartridge is provided with a treatment device accommodating portion in which the treatment device is accommodated. The treatment device accommodating portion is provided with a coupling member accommodating portion and a treatment device main body accommodating portion. The coupling member accommodating portion prevents the connecting portion of the introduction device from being engaged with the engagement portion of the coupling member. The treatment device main body accommodating portion is provided on a distal end side of the coupling member accommodating portion, has the treatment device main body arranged therein, and has an allowing portion which allows engagement when the connecting portion of the introduction device is engaged with the engagement portion of the coupling member.

A cartridge according to an aspect of the present invention accommodates a treatment device which is used together with an endoscope and includes a coupling member having at a proximal end an engagement portion engaged with a distal end of the introduction device led into a body cavity and a treatment device main body provided at a distal end of the coupling member. The cartridge includes a treatment device accommodating portion in which the treatment device is accommodated. The treatment device accommodating portion is provided with a coupling member accommodating portion and a treatment device main body accommodating portion. The coupling member accommodating portion is provided at a proximal end of the treatment device accommodating portion and formed along an outer peripheral surface of the engagement portion of the treatment device, and holds the engagement portion in a state where the distal end of the introduction device is prevented from being engaged with the engagement portion of the coupling member. The treatment device main body accommodating portion has on a distal end side of the coupling member accommodating portion an engagement allowing portion which allows engagement of the engagement portion with respect to the distal end of the introduction device when a force is applied to move the engagement portion toward the distal end from the proximal end of the treatment device accommodating portion at the time of engagement of the engagement portion with the distal end of the introduction device.

BRIEF DESCRIPTION OF THE SEVERAL VIEWS OF THE DRAWING

FIG. 2 show partial cross-sectional views in the clip introduction device according to the first embodiment, in which FIG. 2(A) is a schematic partial cross-sectional view of a distal end of the clip introduction device, and FIG. 2(B) is a schematic partial cross-sectional view of a proximal end of the clip introduction device;

FIG. 3 is a schematic cross-sectional view of one end of an operating portion in the clip introduction device according to the first embodiment;

FIG. 4 is a schematic perspective view showing a structure of a distal end of an operation wire in the clip introduction device according to the first embodiment;

FIG. 5(A) is a schematic perspective view showing a configuration of a proximal end of the operation wire in the clip introduction device according to the first embodiment, and FIG. 5(B) is a schematic cross-sectional view taken along a line 5B-5B in FIG. 5(A);

FIG. 6 is a schematic perspective view showing a configuration of a first slide member of a slider of the operating portion in the clip introduction device according to the first embodiment;

FIGS. 11(A) and (B) are schematic partial cross-sectional views of the clip unit according to the first embodiment.

FIG. 12(A) is an exploded perspective view of a cartridge used when the clip unit according to the first embodiment is loaded into the clip introduction device, and FIG. 12(B) is a schematic perspective view showing a part close to a diameter reducing portion in FIG. 12(A);

FIG. 14(A) is a schematic top view showing a state in which a cartridge having the clip unit included therein is accommodated in a sterile pack according to the first embodiment, and FIG. 14(B) is a side view of FIG. 14(A);

FIG. 15(A) is a schematic plan view showing the cartridge according to the first embodiment, FIG. 15(B) is a side view of FIG. 15(A), FIG. 15(C) is a schematic view showing a state in which a sterile paper sheet is brought into contact with an arc portion of a compressing portion, and FIG. 15(D) is a schematic view showing a side elevation of FIG. 15(C) and illustrating a state in which holes are formed in the sterile paper sheet by breaking projections of the compressing portion;

FIG. 18(A) is a schematic plan view showing a state where a distal end of the hook portion of the clip introduction device is in contact with the elastic arm portion at a proximal end of the coupling member of the clip unit when a distal end tip of the introduction tube of the clip introduction device is in contact with a distal end tip contact portion of the cartridge according to the first embodiment, FIG. 18(B) is a cross-sectional view taken along a line 18B-18B in FIG. 18(A), and FIG. 18(C) is a cross-sectional view taken along a line 18C-18C in FIG. 18(A);

FIG. 20 is a schematic cross-sectional view showing a state where the clip introduction device having the clip unit attached therein is inserted into a forceps channel of an inserting section of an endoscope and the inserting section is bent according to the first embodiment;

FIG. 23(A) is a schematic cross-sectional view showing a state where leg portions of the clip in the clip unit are closed according to the first embodiment, and FIG. 23(B) is a schematic cross-sectional view showing a state where the coupling member is ruptured from the state depicted in FIG. 23(A) to separate the clip unit from the clip introduction device;

FIG. 27(A) is a schematic cross-sectional view showing the cartridge according to the second embodiment, and FIG. 27(B) is a schematic cross-sectional view showing a state where the clip unit is arranged in the cartridge according to the second embodiment;

FIG. 28(A) is a schematic plan view showing a state where the clip unit is arranged in the cartridge according to the second embodiment, and FIG. 28(B) is a schematic plan view showing a state where a distal end of a hook portion of the clip introduction device is brought into contact with an elastic arm portion at a proximal end of a coupling member of the clip unit when a distal end tip of an introduction tube of the clip introduction device is in contact with a distal end tip contact portion of the cartridge according to the second embodiment;

FIGS. 30(A) and 30(B) are schematic plan views showing a grasping forceps according to a fourth embodiment, and FIG. 30(C) is a schematic partial cross-sectional view showing a state where the grasping forceps is connected with an introduction device;

FIGS. 31(A) and 31(B) are schematic plan views showing an indwelling snare according to a fifth embodiment, and FIG. 31(C) is a schematic partial cross-sectional view showing a state where the indwelling snare is connected with an introduction device;

FIG. 32(A) is a schematic plan view showing a state where a distal end of a hook portion of a clip introduction device is brought into contact with an elastic arm portion at a proximal end of a coupling member of a clip unit when a distal end tip of an introduction tube of the clip introduction device is in contact with a distal end tip contact portion of a cartridge according to a prior art, and FIG. 32(B) is a cross-sectional view taken along a line 32B-32B in FIG. 32(A)

DETAILED DESCRIPTION OF THE INVENTION

The best mode for carrying out the present invention will now be described hereinafter with reference to the accompanying drawings. A first embodiment will be explained with reference to FIGS. 1 to 25.

An endo-therapy product system according to this embodiment uses a combination of a clip introduction device 10 (see FIGS. 1 to 6), a clip unit 60 (see FIGS. 7 to 11(B)), a cartridge 70 (see FIGS. 12(A) to 14(B)) and an endoscope (see FIG. 20).

First, a description will be given as to a configuration of the clip introduction device 10, which is an introduction device (an operation device) led to a body cavity according to this embodiment, with reference to FIGS. 1 to 6.

Figure 1:
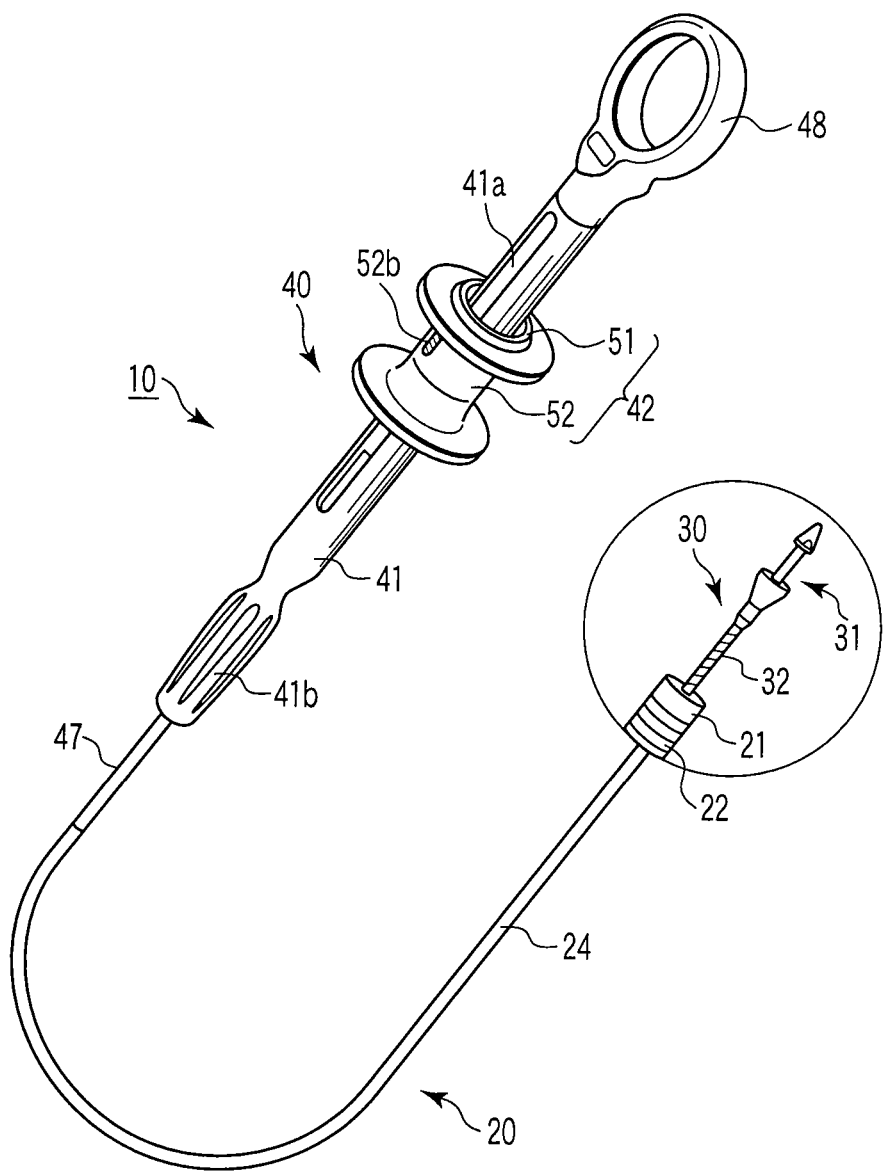
FIG. 1 is a schematic perspective view of a clip introduction device according to a first embodiment of the present invention.
Figure 2:
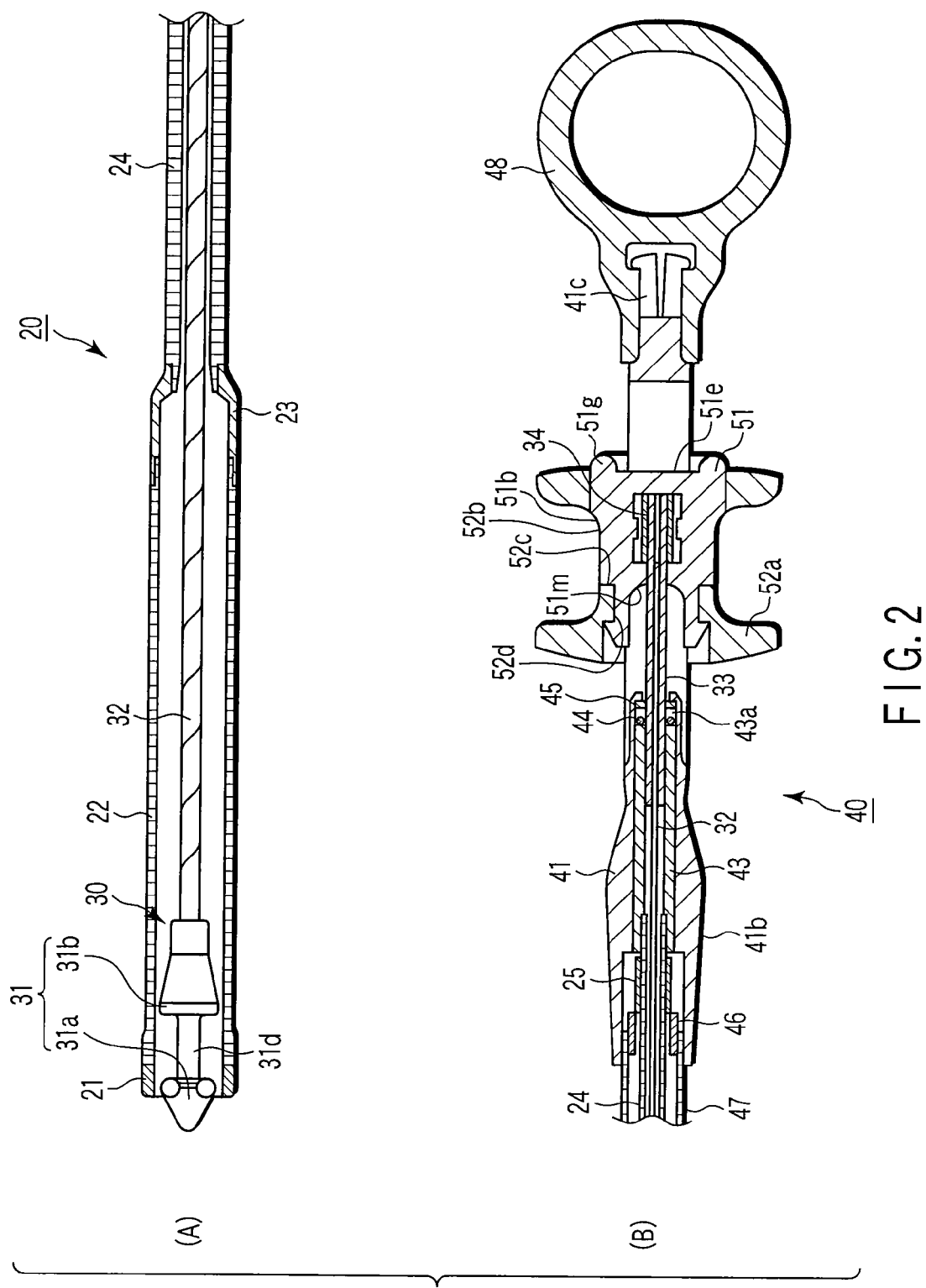

As shown in FIG. 1, this clip introduction device 10 is provided with an introduction tube 20, an operation wire (a wire member) 30, and an operating portion 40. This clip introduction device 10 is combined with an endoscope to be inserted into a treatment device insertion channel (see FIG. 20) of the endoscope, for example. Therefore, the introduction tube 20 is formed to be sufficiently longer than a length which can be inserted into the forceps channel of the endoscope. This introduction tube 20 has flexibility as a whole so that it bends in accordance with a curvature of an inserting section of the endoscope.

As shown in FIGS. 2(A), 2(B) and 3, the introduction tube 20 is equipped with a distal end tip 21, a distal-end-side coil 22, a coil connection pipe 23 and a proximal-end-side coil 24 and a coil accepting pipe 25, and formed into an elongated tubular shape as a whole.

As shown in FIG. 2(A), the distal-end-side coil 22 is arranged on a distal end side of the introduction tube 20. The distal end tip 21 is arranged at a distal end of the distal-end-side coil 22. This distal end tip 21 is formed of, e.g., a stainless steel material into an annular shape having an internal diameter of approximately 2 mm and an external diameter of approximately 2 mm to 3 mm. Therefore, a later-described arrow-head hook portion 31 of the operation wire 30 can be slidably arranged. The distal end of the introduction tube 20 which is an end of this distal end tip 21 is smoothly rounded.

A flat wire formed of a stainless steel material is formed into a close coiling spiral shape so that the distal-end-side coil 22 is formed into a cylindrical shape as a whole. This coil 22 is formed with an internal diameter of approximately 2 mm and an external diameter of approximately 2.5 mm to 3 mm.

The coil connection pipe 23 is arranged at a proximal end of the distal-end-side coil 22. This coil connection pipe 23 is formed of a stainless steel material into a substantially-pipe-like shape having a short axial length. The proximal end of the distal-end-side coil 22 and the distal end of the coil connection pipe 23 are fixed to each other through, e.g., welding. An internal diameter and an external diameter of this pipe 23 are formed to be gradually increased toward the distal end side. That is, the distal end of this pipe 23 is formed in such a manner that the internal diameter and the external diameter are larger than those of the proximal end. The distal end of this coil connection pipe 23 is formed with an internal diameter of approximately 2 mm and an external diameter of approximately 2.5 mm to 3 mm. On the other hand, the proximal end of this pipe 23 is formed with an internal diameter of approximately 1 mm and an external diameter of approximately 2 mm to 2.4 mm. Therefore, this coil connection pipe 23 has the later-described arrow-head hook portion 31 of the operation wire 30 arranged on the distal end side to restrict movement from a predetermined position toward the proximal end side.

The proximal-end-side coil 24 is arranged at the proximal end of the coil connection pipe 23. A wire formed of a stainless steel material is formed into a close coiling spiral shape so that this proximal-end-side coil 24 is formed into a cylindrical shape as a whole. The proximal end of the coil connection pipe 23 and the distal end of the proximal-end-side coil 24 are connected with each other through, e.g., welding. This coil 24 is formed with an internal diameter of approximately 1 mm and an external diameter of approximately 2 mm to 2.4 mm.

As shown in FIGS. 2(B) and 3, the coil accepting pipe 25 is arranged in a state where it covers a part of a proximal end of the proximal-end-side coil 24. This coil accepting pipe 25 is formed of a stainless steel material into a substantially-pipe-like shape. A proximal end of this coil accepting pipe 25 is connected with a distal end of the operating portion 40. An internal diameter of this pipe 25 is formed along the external diameter of the proximal-end-side coil 24, and an external diameter of the same is formed to fall within a range of approximately 2 mm to 4 mm.

As shown in FIGS. 2(A) and 2(B), the operation wire 30 includes the arrow-head hook portion (a connecting portion) 32, a wire 32, an operation pipe 33 and a wire accepting pipe 34.

Figure 7:
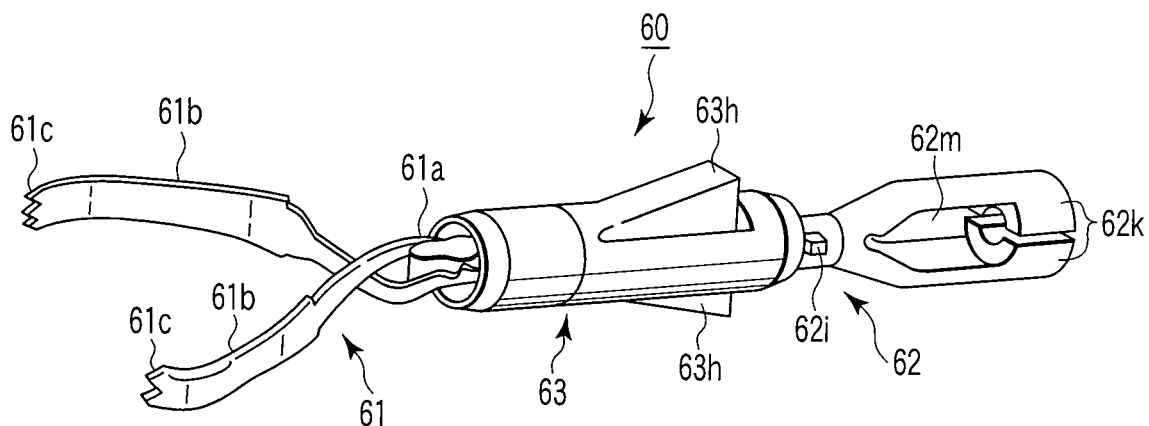
FIG. 7 is a schematic perspective view showing a clip unit according to the first embodiment.
Figure 8:
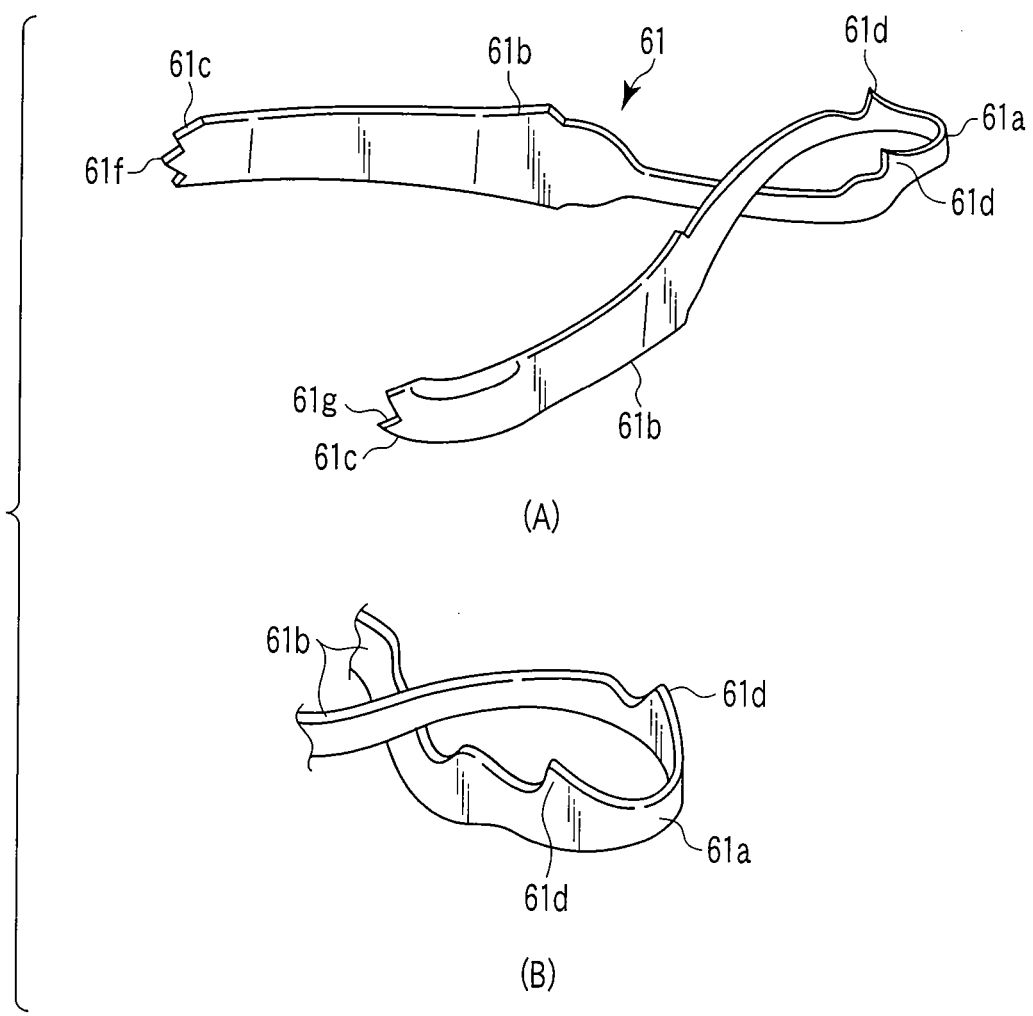
FIG. 8(A) is a schematic perspective view showing a clip in the clip unit according to the embodiment.
FIG. 8(B) is a schematic perspective view showing a part close to a loop portion in FIG. 8(A)
Figure 9:
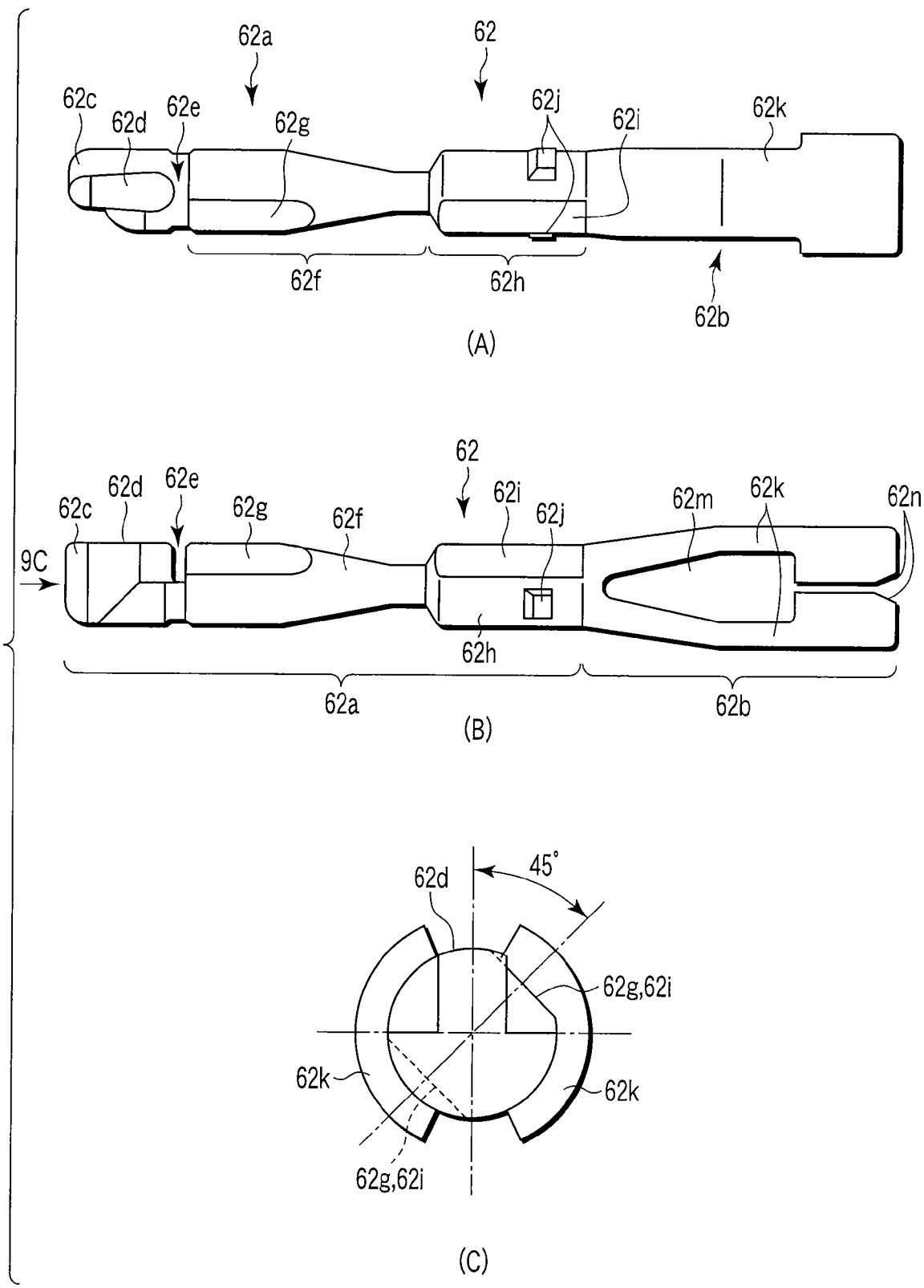
FIGS. 9(A) and 9(B) are schematic plan views showing a coupling member in the clip unit according to the first embodiment.
FIG. 9(C) is a schematic view showing a state observed from a direction of an arrow 9C in FIG. 9(B)
Figure 10:
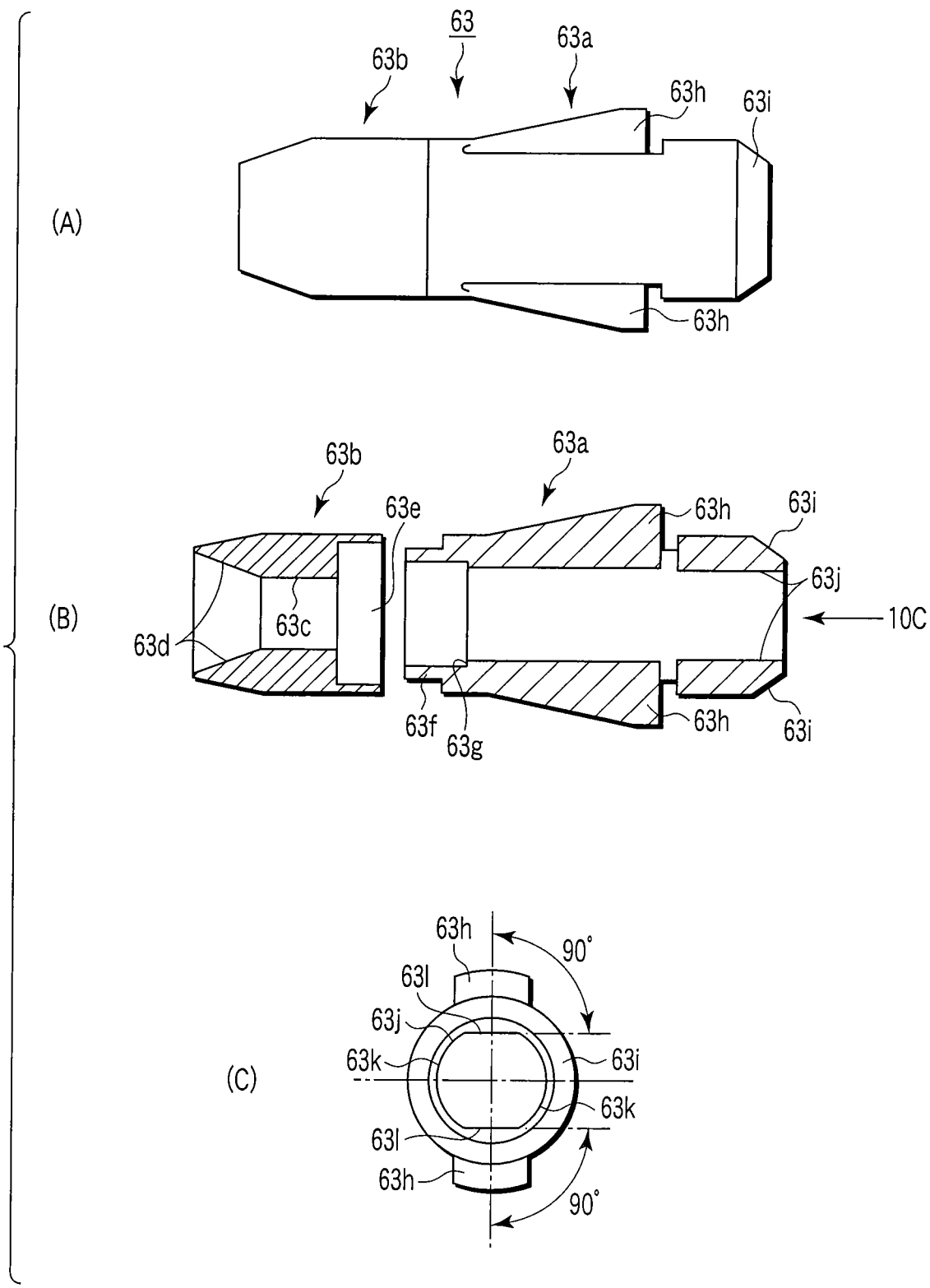
FIG. 10(A) is a schematic side view showing a pressing tube in the clip unit according to the first embodiment.
FIG. 10(B) is a schematic side view showing a state in which a distal end tube and a pressing tube main body of the pressing tube in the clip unit according to the first embodiment are separated from each other.
FIG. 10(C) is a schematic view showing a state observed from a direction of an arrow 10C in FIG. 10(B)

The hook portion 31 is used to hook a clip unit 60 (see FIG. 7). That is, the hook portion 31 is used to connect the clip unit 60. As shown in FIG. 4, a distal end side of the hook portion 31 is formed into a substantially conical shape. This hook portion 31 is formed of a metal material such as a stainless steel material. This hook portion 31 includes a substantially conical engagement portion 31a which hooks to engage with the clip unit 60, and a wire connecting portion 31b provided at a proximal end of this engagement portion 31a. This wire connecting portion 31b is formed into a substantially conical shape whose diameter is reduced from a distal end side toward a proximal end side. A plurality of flat surface portions 31c are formed on a side portion of the proximal end on the cone of the engagement portion 31a. That is, a lateral cross section of the engagement portion 31a at the distal end is formed into a substantially circular shape, and a lateral cross section of the same at the proximal end is formed into a substantially rectangular shape (see FIG. 22(B)). Therefore, the engagement portion 31a has a shape like an arrow head as a whole. The proximal end of the clip unit engagement portion 31a and the distal end of the wire connecting portion 31b are connected with each other through a gap formed by a shaft portion 31d arranged on a central axis of these portions.

A distal end of the wire 32 is fixed at the proximal end of the wire connecting portion 31b by, e.g., welding. That is, the hook portion 31 is fixed at the distal end of the wire 32. This wire 32 is retractably inserted into the introduction tube 20. The wire 32 is formed by twisting, e.g., 19 pieces of a metal signal-line wire consisting of a stainless steel material or the like.

As shown in FIGS. 3 and 5(A), the operation pipe 33 is arranged at a proximal end of the wire 32. This operation pipe 33 is formed as a thin-walled pipe (wall thickness: approximately 0.1 mm) consisting of a metal material such as a stainless steel material. This pipe 33 is caulked and fixed at the proximal end of the wire 32 together with the wire accepting pipe 34. This pipe 33 has a longer length than a movement stroke of a later-described slider 42, and is provided to cover the proximal end of the wire 32.

As shown in FIGS. 2(B) and 5(A), the wire accepting pipe 34 is arranged at the proximal end of the operation pipe 33. The wire accepting pipe 34 is formed into a thick-walled pipe shape by using, e.g., a metal material. This pipe 34 is arranged at the proximal end of the operation pipe 33. As shown in FIG. 5(B), this pipe 34 is caulked together with the operation pipe 33 and fixed at the proximal end of the wire 32. An outer peripheral surface of this pipe 34 is formed into a flat shape by caulking.

As shown in FIGS. 2(B) and 3, the operating portion 40 includes an operating portion main body 41, a slider 42, a guide pipe 43, an O-ring 44, a washer 45, a bending-stopper acceptor 46, a bending stopper 47 and a thumb ring 48.

The operating portion main body 41 is injection-molded by using, e.g., a resin material. As shown in FIG. 1, the main body 41 includes a slit portion 41a which accepts a slider 42 and a rotation grip 41b which rotates the entire main body 41 around a longitudinal axis of the main body 41 on an outer peripheral surface thereof. The rotation grip 41b is formed on a distal end side of the main body 41, and the slit portion 41a is formed on the proximal end side of the main body 41. This slit portion 41a is formed along an axial direction of the main body 41.

As shown in FIG. 2(B), an attachment portion 41c allowing attachment of the thumb ring 48 is provided at the proximal end of the main body 41. The thumb ring 48 is attached to this attachment portion 41c to allow rotation around the axis of the main body 41. Therefore, the attachment portion 41c and the thumb ring 48 can mutually rotate.

As shown in FIG. 3, a hole 41d which has a step and a diameter which is increased at the distal end and reduced at the proximal end is formed on the central axis of the main body 41. This hole 41d is closed at the proximal end of the main body 41. A proximal end of the proximal-end-side coil 24 is arranged at a distal end of the hole 41d of the main body 41. The bending-stopper acceptor 46 is arranged at the distal end of the coil accepting pipe 25 on the outer peripheral surface of the proximal end of this proximal-end-side coil 24. The bending stopper 47 is arranged on an outer peripheral surface of this bending-stopper acceptor 46. An outer peripheral surface of the proximal end of this bending stopper 47 is fixed at the distal end of the hole 41d of the main body 41.

The guide pipe 43 is arranged in the hole 41d of the main body 41. That is, this guide pipe 43 is attached on an inner peripheral surface of the main body 41. This guide pipe 43 is formed of a metal material, e.g., a stainless steel material.

This guide pipe 43 includes an O-ring accommodating portion 43a in which the O-ring 44 is accommodated, and a coil inserting portion 43b into which the proximal end of the proximal-end-side coil 24 is inserted. The O-ring 44 is arranged in the O-ring accommodating portion 43a and has an internal diameter slightly smaller than an external diameter of the operation pipe 33. Therefore, an inner peripheral surface of the O-ring 44 is appressed against an outer peripheral surface of the operation pipe 33.

The O-ring accommodating portion 43a is formed at a proximal end of the guide pipe 43. This O-ring accommodating portion 43a is concave from an inner peripheral surface of the guide pipe 43 toward the outside. This O-ring accommodating portion 43a has an inner peripheral surface having a diameter which is larger than an external diameter of the O-ring 44 and smaller than an external diameter of the guide pipe 43. Further, this O-ring accommodating portion 43a is formed with a length along which the O-ring 44 is movable with respect to the guide pipe 43 in a range of, e.g., 2 mm to 6 mm.

Furthermore, the washer 45 is arranged at the proximal end of the guide pipe 43 to cover the O-ring accommodating portion 43a from the proximal end side. This washer 45 is formed of a metal material having an internal diameter slightly larger than the external diameter of the operation pipe 33 and an external diameter which is substantially equal to that of the guide pipe 43. Therefore, the O-ring 44 can move between a state where it is in contact with the washer 45 and a state where it is separated from the washer 45 and in contact with the distal end of the O-ring accommodating portion 43a while being appressed against the outer peripheral surface of the operation pipe 33.

The slider 42 includes a first slide member 51 as a wire accepting presser, and a second slide member 52 engaged with this first slide member 51.

One pair of first slide members 51 is arranged to fix wire accepting pipe 34 (see FIGS. 5(A) and 5(B)) arranged at the proximal end of the wire 32. As shown in FIG. 6, each slide member 51 is provided with a half ring 51a, an exposure portion 51b, an engagement portion 51c and leg portions 51d and 51e. Each first slide member 51 is injection-molded by using a resin material colored, e.g., green.

The half ring 51a is formed into a semi-donut-like shape, and engaged with a proximal end of the second slide member 52. This half ring 51a is arranged around the proximal end of the main body 41. A projecting portion 51g is formed at a proximal end of this half ring 51a. The exposure portion 51b is extended from the half ring 51a toward the distal end side. When this exposure portion 51b is fitted to the second slide member 52, an outer surface of the exposure portion 51b is exposed so that a finger can be put thereon. The engagement portion 51c is extended toward the distal end side at a distal end of the exposure portion 51b. A grappling portion 51h which engages with the second slide member 52 is extended toward the outside at a distal end of this engagement portion 51c. Therefore, the grappling portion 51h is engaged with the second slide member 52. Furthermore, the grappling portion 51h receives the second slide member 52 when moving the slider 42 toward the distal end side with respect to the slit portion 41a. That is, a force is applied to the grappling portion 51h when moving the slider 42 toward the distal end side.

A receiving portion 51i which receives a force from the second slide member 52 is formed between the exposure portion 51b and the engagement portion 51c. Therefore, the receiving portion 51i receives the second slide member 52 when moving the slider 42 toward an operator's hand side with respect to the slit portion 41a. The leg portions 51d and 51e are extended toward the slit portion 41a of the main body 41 from the exposure portion 51b. The leg portions 51d and 51e are slidable with respect to the slit portion 41a. A fixing portion 51j which holds and fixes the wire accepting pipe 34 is formed between these leg portions 51d and 51e. Since the wire accepting pipe 34 is fixed by the fixing portion 51j, when the leg portions 51d and 51e move, the wire accepting pipe 34 also moves in accordance with this movement.

A slit contact surface 51m which is brought into contact with a distal end of the slit portion 41a of the main body 41 is formed on a distal end surface of the leg portion 51d on the distal end side with respect to the main body 41. On the other hand, a slit contact surface 51n which is brought into contact with a proximal end of the slit portion 41a is formed on a proximal end surface of the leg portion 51e of the proximal end side with respect to the main body 41. These slit contact surfaces 51m and 51n define an amount of movement of the slider 42 with respect to the slit portion 41a.

The second slide member 52 includes a finger hook portion 52a, a slit portion 52b, a slit end 52c and a step portion 52d. The finger hook portion 52a is formed into a pair of disc shapes parallel with each other. The slit portion 52b in which the exposure portion 51b is arranged is formed between the finger hook portion 52a on the distal end side and the finger hook portion 52a on the proximal end side. Therefore, the exposure portion 51b of the first slide member 51 is fitted in the slit portion 52b of the second slide member 52 so that outer peripheral surfaces of the second slide member 52 and the exposure portion 51b are formed as one surface. Moreover, the leg portions 51d and 51e of the first slide member 51 are arranged in this slit portion 52b. The slit end 52c on the distal end side of this slit portion 52b is in contact with the receiving portion 51i at the proximal end of the engagement portion 51c of the first slide member 51.

The step portion 52d is formed on the distal end side apart from the slit end 52c. This step portion 52d is in contact with the grappling portion 51h at the distal end of the engagement portion 51c of the first slide member 51. Therefore, the slider 42 having the first slide member 51 and the second slide member 52 fitted to each other can slide with respect to the slit portion 41a of the main body 41.

The bending-stopper acceptor 46 is arranged at the distal end of the hole 41d of the main body 41. This bending-stopper acceptor 46 has an internal diameter which is larger than the external diameter of the proximal-end-side coil 24 and smaller than the external diameter of the coil accepting pipe 25. A screw portion 46a into which the bending stopper 47 can be screwed is provided at an external diameter portion of the bending-stopper acceptor on the distal end side.

The bending stopper 47 is processed into a coil-like shape in which a single-line wire formed of, e.g., a stainless steel material is nondense on the distal end side but dense on the operator's hand side. An inner peripheral surface of the proximal end of this bending stopper 47 is screwed into the screw portion 46a of the bending-stopper acceptor 46. At this time, an outer peripheral surface of this bending stopper 47 is appressed against an inner peripheral surface of the distal end of the main body 41.

A description will now be given as to a structure of the substantially-Y-shaped clip unit 60 as an operative device (a treatment device) according to this embodiment with reference to FIGS. 7 to 11(B).

The clip unit 60 can be loaded with respect to the hook portion 31 at the distal end of the wire 32 of the clip introduction device 10. As shown in FIG. 7, the clip unit 60 includes a clip 61, a coupling member 62 and a pressing tube 63 as a fastening member.

As shown in FIG. 8(A), in the clip 61, a metal plate material such as a leaf spring material consisting of, e.g., a stainless steel material is bent at the center to form a loop portion (a base portion) 61a. In the clip 61, a pair of arms (clip arms) 61b are crossed at a position in the vicinity of the loop portion 61a and then extended in such a manner that their distal ends are separated from each other. Tissue grasping portions (clip claws) 61c are formed at distal ends of this clip 61. A distance between the distal ends of these arms 61b is formed to be, e.g., approximately 8 mm to 9 mm.

A crossing portion of the arms 61b of the clip 61 is formed to be narrower from the distal end side, and the tissue grasping portions 61c face each other. Sawtooth projections 61d which protrudes in a direction of a plate width are formed in the vicinity of the loop portion 61a of the arms 61b. As shown in FIG. 8(B), each projection 61d is formed into an inclined plane with a acute angle on the tissue grasping portion 61c side and an inclined plane with an obtuse angle on the loop portion 61a side. Therefore, the clip 61 slides on an inner surface of the pressing tube 63 when the clip 61 is moved to be pulled into the pressing tube 63, but it bites into the inner surface of the pressing tube 63 when it is moved in a direction opposite to the pull-in direction.

As shown in FIG. 8(A), the tissue grasping portions 61c are inwardly bent at substantially 90 degrees to approximately 150 degrees to face each other. A substantially triangular convex portion 61f is formed on one of the tissue grasping portions 61c. A substantially triangular concave portion 61g which engages with the convex portion 61f is formed on the other one of the tissue grasping portions 61c.

The coupling member 62 is manufactured by injection-molding a resin material having high strength such as a liquid crystal polymer or a polyamide synthetic fiber. This coupling member 62 is colored, e.g., white. As shown in FIGS. 9(A) and 9(B), the coupling member 62 includes an inserting portion 62a which is inserted into an inner space of the pressing tube 63, and a coupling portion 62b provided at a proximal end of this inserting portion 62a. The coupling portion 62b is an engagement portion with which the arrow-head hook portion 31 of the introduction device 10 is engaged (coupled).

The inserting portion 62a has at a distal end thereof a protruding portion 62c which protrudes from a distal end of the pressing tube 63 in a state where the coupling member 62 is inserted in the inner space of the pressing tube 63. This protruding portion 62c is formed into a substantially cylindrical rod shape. A flat elliptical projecting portion 62d which is long in an axial direction is formed in this protruding portion 62c. As shown in FIG. 9(C), this projecting portion 62d is a remaining part obtained when a substantially sectoral columnar portion is removed from the protruding portion 62c.

A narrow diameter portion 62e having a short axial length is formed at a proximal end of the protruding portion 62c. A substantially conical cone portion 62f is arranged at a proximal end of this narrow diameter portion 62e. The loop portion 61a of the clip 61 is hooked on the narrow diameter portion 62e between the protruding portion 62c and the cone portion 62f. A dimension of the narrow diameter portion 62e is set in such a manner that this portion is broken when a break force of, e.g., 20 N (Newton) to 60 N due to tension is applied to the protruding portion 62c by the clip 61.

The cone portion 62f is formed to have a large diameter on the distal end side and a small diameter on the proximal end side. A pair of flat surface portions 62g parallel with each other is formed on a part of a side portion of the distal end of this cone portion 62f.

A cylinder portion 62h formed into a substantially cylindrical shape having a diameter larger than that on the proximal end side is arranged at the proximal end of the cone portion 62f. A pair of flat surface portions 62i parallel with each other is formed on a side portion of this cylinder portion 62h. As shown in FIG. 9(C), the flat surface portion 62g of the cone portion 62f and the flat surface portion 62i of the cylinder portion 62h are formed to be inclined at, e.g., 45 degrees with respect to a protruding direction of the narrow diameter portion 62e. These flat surface portions 62g and 62i have shapes matched with flat surfaces 63l of the inner peripheral surface of the proximal end of a later-described pressing tube main body 63a at the proximal end of the pressing tube 63.

A pair of latch projections 62j are formed on the side portions of the flat portions 62i of the cylinder portion 62h. It is to be noted that a maximum external diameter of the distal end of the cone portion 62f and the external diameter of the cylinder portion 62h are set to sizes which allow close fitting with the inner peripheral surface of the pressing tube 63. Therefore, the latch projections 62j of the cylinder portion 62h protrude toward the outside beyond a size of the internal diameter of the pressing tube 63. Accordingly, these latch projections 62j are brought into contact with the proximal end of the pressing tube 63 (see FIG. 11(A)).

As shown in FIGS. 9(A) and 9(B), the coupling portion 62b is provided with two forked elastic arm portions (connection arm portions) 62k at the proximal end of the cylinder portion 62h of the inserting portion 62a. These elastic arm portions 62k can be elastically deformed with respect to the proximal end of the cylinder portion 62h. That is, these elastic arm portions 62k can be mutually opened/closed. Additionally, as shown in FIG. 9(B), tapered portions 62n are formed on inner peripheral surfaces of these elastic arm portions 62k at proximal ends thereof, the tapered portion 62n being used to position the distal end of the clip unit engagement portion 31a when the distal end of the clip unit engagement portion 31a of the arrow-head hook portion 31 is brought into contact with the proximal ends of the elastic arm portions 62k.

A notch portion 62m which holds and accommodates the clip unit engagement portion 31a of the arrow-head hook portion 31 is formed between these elastic arm portions 62k. This notch portion 62m is formed into a shape which is appressed against the outer peripheral surface of the clip unit engagement portion 31a of the arrow-head hook portion 31. That is, the notch portion 62m is formed into a shape with which the flat surface portions 31c of the clip unit engagement portion 31a of the hook portion 31 are engaged.

Here, respective flat surface portions 62l (see FIG. 22(B)) are formed on the inner surface of this notch portion 62m. The flat surface portions 62l hold the flat surface portions 31c of the clip unit engagement portion 31a at the distal end of the arrow-head hook portion 31 (see FIG. 4). It is to be noted that the elastic arm portions 62k are provided at the proximal end of the notch portion 62m to hold the shaft portion 31d of the hook portion 31.

As shown in FIGS. 10(A) and 10(B), the pressing tube 63 includes a pressing tube main body 63a, and a distal end tube 63b which is attached to a distal end of this pressing tube main body 63a. The pressing tube main body 63a is manufactured by injection-molding a material softer than the clip 61, e.g., a highly rigid resin material having appropriate elasticity like PPA (polyphthal amide) or PA (polyamide). This pressing tube main body 63a is colored, e.g., blue. On the other hand, the distal end tube 63b is formed of a metal material with high strength such as a stainless steel material.

As shown in FIGS. 10(A) and 10(B), an external diameter of a distal end of the distal end tube 63b is formed to be tapered with respect to the proximal end side. A maximum external diameter of this distal end tube 63b is formed to be equal to an external diameter of the pressing tube main body 63a. As shown in FIG. 10(B), in the distal end tube 63b is formed an internal diameter inclined portion 63d whose internal diameter is gradually increased toward the distal end of the distal end tube 63b from a distal end of a minimum internal diameter portion 63c. A fitting hole 63e having a diameter which allows fitting of a later-described fitting portion 63f of the pressing tube main body 63a is formed at a proximal end of this distal end tube 63b. An internal diameter of such a distal end tube 63b is approximately 1 mm to 2 mm.

The pressing tube main body 63a includes a fitting portion 63f which fits in the proximal end of the distal end tube 63b. This fitting portion 63f is formed with an external diameter which is smaller than the maximum external diameter portion.

An internal diameter of the pressing tube main body 63a is formed to be slightly larger on the distal end side, and an internal diameter step portion 63g is formed between the internal diameter on the distal end side and the internal diameter on the rear end side. A pair of retractable wings 63h are formed on the outer side of this internal diameter step portion 63g. These retractable wings 63h are retractable with respect to the inside of the pressing tube main body 63a when they are elastically deformed with respect to the proximal end of the fitting portion 63f of the pressing tube main body 63a. Each of these retractable wings 63h has an external diameter which is larger than the internal diameter of the distal end tip 21 of the introduction tube 20 in a protruding state. Further, each of these retractable wings 63h is formed to be equal to or slightly smaller than the external diameter of the distal end tube 63b of the pressing tube 63 in a retracted state. The internal diameter of such a pressing tube main body 63a is approximately 1 mm to 2 mm. It is to be noted that the external diameter of the proximal end of the pressing tube main body 63a is formed to be slightly smaller than the internal diameter of the distal end tip 21 of the introduction tube 20.

A taper portion 63i is formed on an outer peripheral surface of the proximal end of the pressing tube main body 63a. As shown in FIG. 10(C), an inner peripheral surface of the proximal end of this pressing tube main body 63a is provided with an oval hole 63j defined by two semicircular surfaces 63k and two parallel surfaces 63l. An angle formed between a parallel axis of the parallel surfaces 63l constituting this oval hole 63j and an axis connecting the centers of the pair of retractable wings 63h is set to 90 degrees.

It is to be noted that the coupling member 62 and the pressing tube main body 63a of the pressing tube 63 are colored differently, and hence a boundary part between the coupling member 62 and the pressing tube main body 63a of the pressing tube 63 can be clearly recognized.

A description will now be given as to an assembling operation of the clip unit 60 for assembling the clip 61, the coupling member 62 and the pressing tube 63.

As shown in FIG. 11(A), the coupling member 62 is inserted from the proximal end of the pressing tube main body 63a of the pressing tube 63 so that the protruding portion 62c of the coupling member 62 protrudes from the distal end tube 63b of the pressing tube 63. In this state, when the loop portion 61a is hooked on the projecting portion 62d of the protruding portion 62c of the coupling member 62, the clip 61 is engaged with the coupling member 62.

Then, when the proximal end of the coupling member 62 is lightly pulled toward the operator's hand side with respect to the pressing tube 63, the loop portion 61a of the clip 61 is brought into contact with the inner peripheral surface of the distal end tube 63b of the pressing tube 63. At this time, the latch projections 62j of the coupling member 62 are brought into contact with the proximal end surface of the pressing tube main body 63a, and the clip 61, the coupling member 62 and the pressing tube 63 are engaged with each other. Therefore, as shown in FIG. 11(A), assembling of the clip unit 60 is completed.

In this state, when the proximal end of the coupling member 62 is further pulled toward the operator's hand side with respect to the pressing tube 63, the loop portion 61a of the clip 61 is pulled toward the inside while being in contact with the minimum internal diameter portion 63c through the internal diameter inclined portion 63d of the metal distal end tube 63b of the pressing tube 63. Then, as shown in FIG. 11(B), the loop portion 61a of the clip 61 is crushed by the distal end tube 63b or the pressing tube main body 63a of the pressing tube 63, and hence the arms 61b are once opened.

As shown in FIG. 11(B), the proximal end of the coupling member 62 is further pulled toward the operator's hand side. Although not shown, the projections 61d of the clip 61 are brought into contact with the internal diameter step portion 63g of the pressing tube 63. Therefore, the pull-in operation of the clip 61 toward the inside of the pressing tube 63 is stopped. Accordingly, the arms 61b of the clip 61 are held in the maximum open state.

When the proximal end of the coupling member 62 is further pulled toward the operator's hand side with respect to the pressing tube 63 from this state, the projections 61d of the clip 61 climb over the internal diameter step portion 63g of the pressing tube main body 63a and the clip 61 is further pulled toward the inside of the pressing tube 63. Therefore, the arms 61b of the clip 61 reach the minimum internal diameter portion 63c through the internal diameter inclined portion 63d of the distal end tube 63b of the pressing tube 63 to be opened.

In this example, the pressing tube main body 63a is formed of a resin material which is softer than that of the clip 61 and has approximate elasticity. Therefore, the projections 61d of the clip 61 bite into the inner wall of the pressing tube main body 63a to be restrained, thereby preventing the clip 61 from moving in the pressing tube 63 along the axial direction. Accordingly, the arms 61b of the clip 61 are maintained in the closed state.

As shown in FIG. 8(B), the projections 61d of the clip 61 are formed into a sawtooth shape which protrudes in a direction of a plate width of the loop portion 61a. Therefore, the clip 61 slightly moves toward a fastening side (a closing direction of the arms 61b), but the projections 61d of the clip 61 bite into the inner wall of the pressing tube main body 63a on a returning side (an opening direction of the arms 61b), thereby avoiding movement.

Figure 13:
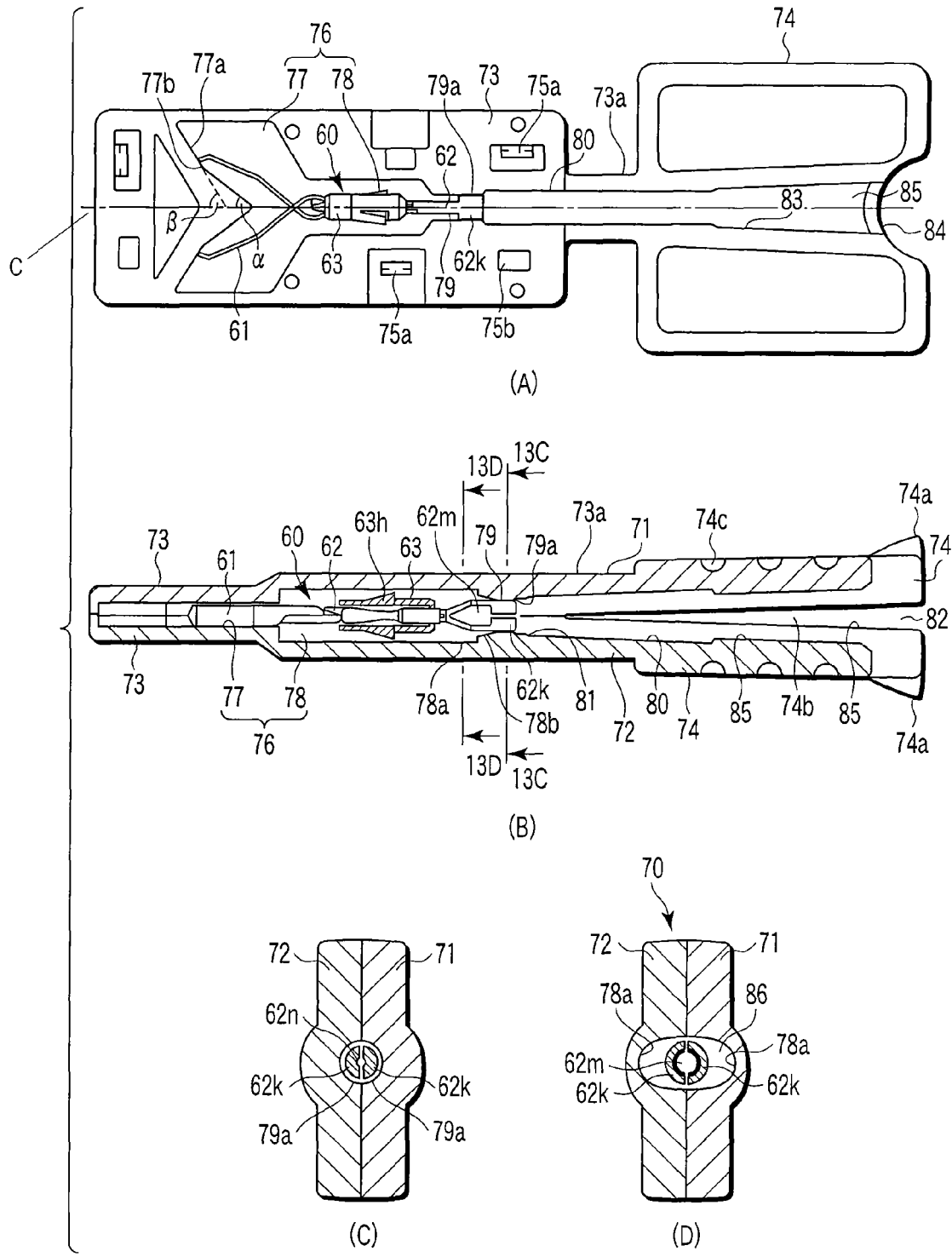
FIG. 13(A) is a schematic plan view showing a state in which the clip unit is arranged in a cartridge according to the first embodiment.
FIG. 13(B) is a schematic cross-sectional view showing a state in which the clip unit is arranged in the cartridge according to the first embodiment.
FIG. 13(C) is a schematic cross-sectional view taken along a line 13C-13C in FIG. 13(B)
FIG. 13(D) is a schematic cross-sectional view taken along a line 13D-13D in FIG. 13(B)

As shown in FIGS. 12(A) and 13(B), such a clip unit 60 is included in the cartridge (a clip case) 70 in order to facilitate loading (attachment) of the clip unit 60 into the clip introduction device 10. Therefore, a configuration of the cartridge (the clip case) 70 as an operative instrument according to this embodiment will now be described with reference to FIGS. 12(A) to 13(D).

As shown in FIGS. 12(A) and 13(B), the cartridge 70 which accommodates the clip unit 60 is provided with an upper case 71 and a lower case 72 having the same shape. The upper case 71 and the lower case 72 are manufactured by injection molding using a transparent resin material having appropriate hardness such as ABS, PC, PP, PS, acrylic, cycloolefin polymer and others. The transparent resin material is used because a judgment upon whether the clip unit 60 exists inside can be facilitated. It is preferable for these upper case 71 and lower case 72 to be appropriately colored, such as transparent red, yellow, blue or green. These colors are appropriately selected when the type of clip unit 60 needs to be discriminated or a treatment device which substitutes for the clip unit 60 is used. It is to be noted that the cartridge 70 has a width of approximately 10 mm to 20 mm, a length of approximately 50 mm and a thickness of approximately 5 mm and is formed to have a dimension helping a user's grasp.

As shown in FIG. 12(A), a clip unit accommodating portion (a treatment device accommodating portion) 73 which accommodates the clip unit 60 is formed at one end of each of the upper case 71 and the lower case 72 in the longitudinal direction. A compressing portion 74 is formed at the other end of the same. The compressing portion 74 has a size which is, e.g., approximately 20 mm×20 mm and suitable to be nipped by fingers. It is to be noted that breaking projections 74a which are used to break a blister 90b of a later-described sterile pack 90 are formed at a proximal end of the compressing portion 74.

As shown in FIG. 13(B), the coupling portions 73a between the clip unit accommodating portions 73 and the compressing portions 74 are bent in such a manner that the compressing portions 74 of the upper case 71 and the lower case 72 are separated from each other. Therefore, a gap 74b is formed between the compressing portions 74 of both the upper case 71 and the lower case 72. A plurality of, e.g., semispherical concave portions 74c are formed as slip stoppers at the time of compression are formed on outer surfaces of the compressing portions 74.

As shown in FIG. 12(A), three protruding engagement claws 75a and three engagement holes 75b are formed on an inner surface of the clip unit accommodating portion 73 in each of the upper case 71 and the lower case 72. The engagement claws 75a of the upper case 71 engage with the engagement holes 75b of the lower case 72, and the engagement claws 75a of the lower case 72 engage with the engagement holes 75b of the upper case 71. Therefore, the upper case 71 and the lower case 72 are fitted to each other.

It is to be noted that the upper case 71 and the lower case 72 have the same shape, and hence the lower case 72 as one of these cases will be described as a representative case.

As shown in FIG. 13(A), the clip unit accommodating portion 73 includes a clip main body accommodating portion (a treatment device main body accommodating portion) 76 formed of a substantially-Y-shaped concave portion and arranged on central axis "C". This clip main body accommodating portion 76 includes a clip accommodating portion 77 and a pressing tube accommodating portion (a fastening member accommodating portion) 78 provided at a proximal end of this clip accommodating portion 77.

The clip 61 of the clip unit 60 is accommodated in the clip accommodating portion 77 with the arms 61b being opened. A tapered surface 77a with which the tissue grasping portions 61c at the distal ends of the arms 61b of the clip 61 are brought into contact is formed at a distal end of this clip accommodating portion 77. A bent portion 77b is symmetrically formed with respect to a central axis of the cartridge 70 on this tapered surface 77a. Here, an angle α with respect to a central axis in a range from the central axis of the cartridge 70 to the bent portion 77b is formed to be smaller than an angle β with respect to a central axis in a range from the bent portion 77b to an end of the tapered surface 77a. That is, assuming the a friction coefficient of the tapered surface 77a is the same, the tissue grasping portions 61c at the distal ends of the arms 61b of the clip 61 can be readily slid when moving from the central axis to the bent portion 77b as compared with a case of moving from the bent portion 77b to the end of the tapered surface 77a. In regard to an amount of opening of the distal ends of the arms 61b of the clip 61, the tissue griping portions 61c at the ends of the clip 61 are usually brought into contact with the bent portion 77b of the tapered surface 77a. This tapered surface 77a allows opening/closing in a state where the end of the clip 61 of the clip unit 60 is in contact with the bent portion 77b.

An arm reducing portion 77c is formed at a proximal end of this clip accommodating portion 77. This arm reducing portion 77c is used for guiding in a direction of reducing an amount of opening of the arms 61b of the clip 61 on an opposite side of the tapered surface 77a on the distal end side for guiding in a direction of increasing an amount of opening of the arms 61b of the clip 61.

A pressing tube accommodating portion (a fastening member accommodating portion) 78 which is formed of an arc groove and usually accommodates the pressing tube 63 is formed at the proximal end of this clip accommodating portion 77. This pressing tube accommodating portion 78 includes an elastic arm portion diameter increasing portion 78a which allows opening/closing of the elastic arm portions 62k of the coupling member 62, and a retractable wing accommodating concave portion 78b.

As shown in FIG. 13(D), the elastic arm portion diameter increasing portion 78a is an opening/closing allowing portion which allows the elastic arm portions 62k of the coupling member 62 to be elastically expanded (opened/closed). A lateral cross-sectional shape of this elastic arm portion diameter increasing portion 78a is a substantially elliptic shape in a state where the upper case 71 and the lower case 72 are engaged with each other. Therefore, the elastic arm portion diameter increasing portion 78a can be deformed to open/close the elastic arm portions 62k of the coupling member 62 in a predetermined direction when the arrow-head hook portion 31 of the clip introduction device 10 is engaged with the coupling member 62 of the clip unit 60. That is, the elastic arm portion diameter increasing portion 78a is an engagement allowing portion of the elastic arm portions 62k. Therefore, the diameter increasing portion 78a allows expansion (opening/closing) of the proximal ends of the elastic arm portions 62k.

The retractable wing accommodating concave portion 78b which allows the retractable wings 63h of the pressing tube 63 to protrude with respect to the pressing tube main body 63a or to be accommodated in the pressing tube main body 63a is formed at a proximal end of the elastic arm portion diameter increasing portion 78a.

As shown in FIG. 12(B), a tapered surface 78c and a vertical surface 78d arranged at a position adjacent to this tapered surface 78c are formed in the retractable wing accommodating concave portion 78b.

A diameter of the tapered surface 78c is increased from the proximal end side toward the distal end side in a substantially tapered shape (a horn-like shape) on a ¼ circumference. Therefore, when the pressing tube 63 is slid from the distal end side toward the proximal end side, the retractable wings 63h of the pressing tube 63 are accommodated in the pressing tube 63. On the contrary, when the pressing tube 63 is slid from the proximal end side toward the distal end side, the retractable wings 63h of the pressing tube 63 protrude toward the outside of the pressing tube 63.

A coupling member accommodating portion 79 which accommodates the proximal end of the coupling member 62 is formed at a proximal end of these tapered surface 78c and vertical surface 78d, i.e., the proximal end of the pressing tube accommodating portion 78. As shown in FIGS. 12(B) and 13(B), the coupling member accommodating portion 79 is provided with an elastic arm portion diameter reducing portion (which also serves as a retractable wing diameter reducing portion) 79a. This diameter reducing portion 79a is a closing portion which holds the elastic arm portions 62k in a diameter reduced (closed) state. That is, when the clip unit 60 is accommodated in the cartridge 70, the diameter reducing portion 79a holds the elastic arm portion 62k of the coupling member 62 to be prevented from being expanded. This diameter reducing portion a is a minimum diameter portion which is a semicircular groove whose diameter is smaller than the internal diameter of the distal-end-side coil 22, e.g., approximately 1.9 mm. As shown in FIG. 13(C), a lateral cross-sectional shape of this diameter reducing portion 79a is a substantially circular shape in a state where the upper case 71 and the lower case 72 are engaged with each other. Therefore, the proximal ends of the elastic arm portions 62k are prevented from being expanded (opened/closed) by the diameter reducing portion 79a.

As described above, when the pressing tube 63 is slid from the distal end side toward the proximal end side, the retractable wings 63h of the pressing tube 63 are accommodated in the pressing tube 63. Therefore, the arm portion diameter reducing portion 79a smoothly connected with the tapered surface 78c can hold the retractable wing accommodating concave portion 78b of the pressing tube accommodating portion 78 in an accommodated state. On the contrary, when the pressing tube 63 is slid from the arm portion diameter reducing portion 79a toward the tapered surface 78c, the retractable wings 63h of the pressing tube 63 protrude.

At a proximal end of the elastic arm portion diameter reducing portion 79a is formed a distal end tip contact portion 81 with which a distal end surface of the distal end tip 21 of the introduction tube 20 is brought into contact when the introduction tube 20 is inserted into the introduction tube inserting portion 80 of the cartridge 70. The distal end tip contact portions 81 of the upper case 71 and the lower case 72 form a circular shape in a state where the upper case 71 and the lower case 72 are engaged with each other. Further, in a state where the distal end of the distal end tip 21 of the introduction tube 20 is in contact with the distal end tip contact portion 81, the internal diameter of the distal end tip 21 is equal to that of the arm portion diameter reducing portion 79a. Therefore, a surface of the arm portion diameter reducing portion 79a is smoothly connected with an inner peripheral surface of the distal end tip 21.

As shown in FIGS. 12(A) and 13(A), an introduction tube inserting portion (an introduction device inserting portion) 80 which is continuous with the diameter reducing portion 79a of the coupling member accommodating portion 79 and formed of an arc groove is formed on an inner surface of the compressing portion 74 on a proximal end side of the distal end tip contact portion 81. This introduction tube inserting portion 80 is provided with an inclined surface portion 83 (see FIG. 13(A)) whose diameter is gradually increased toward an inlet 82 (see FIG. 13(B)) on the proximal end side. A diameter of the inlet 82 is, e.g., not smaller than 3 mm, and an arc surface 84 having a semicircular shape as seen from a plane is formed. It is to be noted that this arc surface 84 does not have to be an arc, and it may have, e.g., a V-shape.

A convex portion having a length of, e.g., 1 mm to 5 mm is formed at a proximal end of the introduction tube inserting portion 80. This convex portion forms an introduction tube fixing portion 85 (see FIG. 13(B)) which presses and fixes the introduction tube 20 from a vertical direction.

It is to be noted that the clip unit 60 is arranged on a substantially central axis of the cartridge 70 in a state where the clip unit 60 is arranged in the cartridge 70.

As shown in FIGS. 14(A) and 14(B), the cartridge 70 having the clip unit 60 accommodated therein is blister-packaged and enclosed in a sterile pack 90. This sterile pack 90 includes a sterile paper sheet 90a on which the clip unit 60 is mounted and a blister 90b which covers this sterile paper sheet 90a. The blister 90b is sealed to be appressed against the sterile paper sheet 90a by heat sealing, thereby maintaining an inner sterile condition. That is, the clip unit 60 and the cartridge 70 are held in a sterile condition in the sterile pack 90. It is to be noted that the blister 90b is formed by thermo-forming a transparent sheet film consisting of PET or PS (polystyrene) into a shape allowing accommodation of the cartridge 70.

Figure 16:
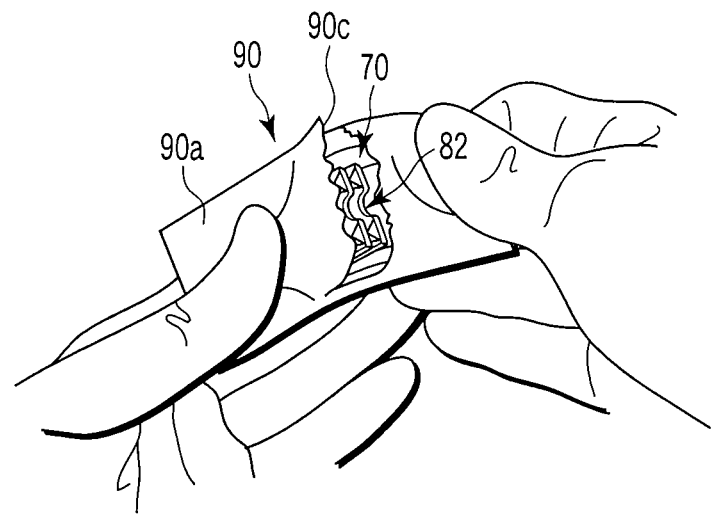
FIG. 16 is a schematic perspective view showing how the cartridge is taken out from the sterile pack according to the first embodiment.

In the sterile pack 90, when a strong thrusting force is applied from the blister 90b side, the sterile paper sheet 90a is torn open as shown in later-described FIG. 16 by breaking projections 74a formed at the proximal end of the compressing portion 74 of the cartridge 70. At this time, the inlet 82 of the introduction tube inserting portion 80 arranged at an intersection of diagonal lines of a square connecting apexes of the four breaking projections 74a appears when the sterile paper sheet 90a is torn open. Therefore, even if the cartridge 70 is not completely taken out from the sterile pack 90, the distal end of the introduction tube 20 of the clip introduction device 10 can be readily inserted toward the distal end tip contact portion 81 from the inlet 82 of the introduction tube inserting portion 80.

A description will now be given as to a function when using a combination of the clip introduction device 10, the clip unit 60 and the cartridge 70 according to this embodiment with reference to FIGS. 15(A) to 25.

The slider 42 of the clip introduction device 10 shown in FIGS. 1 and 2(B) is moved until it comes into contact with the proximal end side close to the thumb ring 48. At this time, the distal end of the clip unit engagement portion 31a of the hook portion 31 shown in FIG. 2(A) is placed in the distal-end-side coil 22 of the introduction tube 20.

As shown in FIGS. 15(A) and 15(B), the breaking projections 74a of the cartridge 70 accommodated in the sterile pack 90 in the sterile condition are pressed toward the sterile paper sheet 90a side from the blister 90b side. Then, the breaking projections 74a form two holes in the sterile paper sheet 90a.

When the breaking projections 74a are further pressed toward the sterile paper sheet 90a side from the blister 90b side of this sterile pack 90, the sterile paper sheet 90a is torn open along the arc surface 84 at the proximal end of the compressing portion 74 as shown in FIGS. 15(C) and 15(D). Therefore, as shown in FIG. 16, a torn opening 90c having a size allowing exposure of the proximal end of the compressing portion 74 of the cartridge 70 can be readily formed in the sterile paper sheet 90a with a light force.

That is, the sterile pack 90 having the cartridge 70 including the clip unit 60 enclosed therein is held with the compressing portion 74 of the cartridge 70 facing upward, and the sterile pack 90 is pulled to be bent while holding an upper end thereof. Then, as shown in FIG. 16, the blister 90b or the sterile paper sheet 90a is torn so that the inlet 82 of the introduction tube inserting portion 80 of the cartridge 70 is exposed to the outside of the sterile pack 90.

As shown in FIG. 12(A), the clip unit 60 is accommodated between the upper case 71 and the lower case 72 of the cartridge 70. The clip 61 of the clip unit 60 is set in each clip accommodating portion 77 of the upper case 71 and the lower case 72, the pressing tube 63 is set in each pressing tube accommodating portion 78, and the coupling member 62 is set in each coupling member accommodating portion 79.

The proximal end of the elastic arm portions 62k of the coupling member 62 of the clip unit 60 is arranged in the diameter reducing portion 79a which is the minimum diameter portion of the cartridge 70. Therefore, the elastic arm portions 62k at the proximal end of the coupling member 62 are prevented from being expanded. Furthermore, the tissue grasping portions 61c at the ends of the arms 61b of the clip 60 are in contact with the inner peripheral surface of the clip accommodating portion 77, and an elastic force of the arms 61b of the clip 61 restricts movement of the clip unit 60 in the axial direction.

Figure 17:
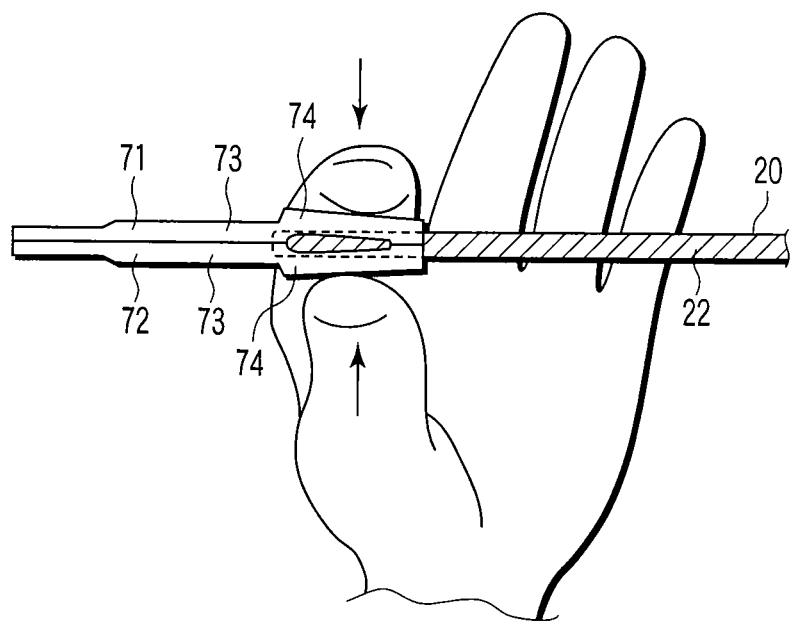
FIG. 17 is a schematic view showing a state in which an introduction tube of the clip introduction device is inserted into the cartridge having the clip unit arranged therein to fix the introduction tube to the cartridge according to the first embodiment.
Figure 19:
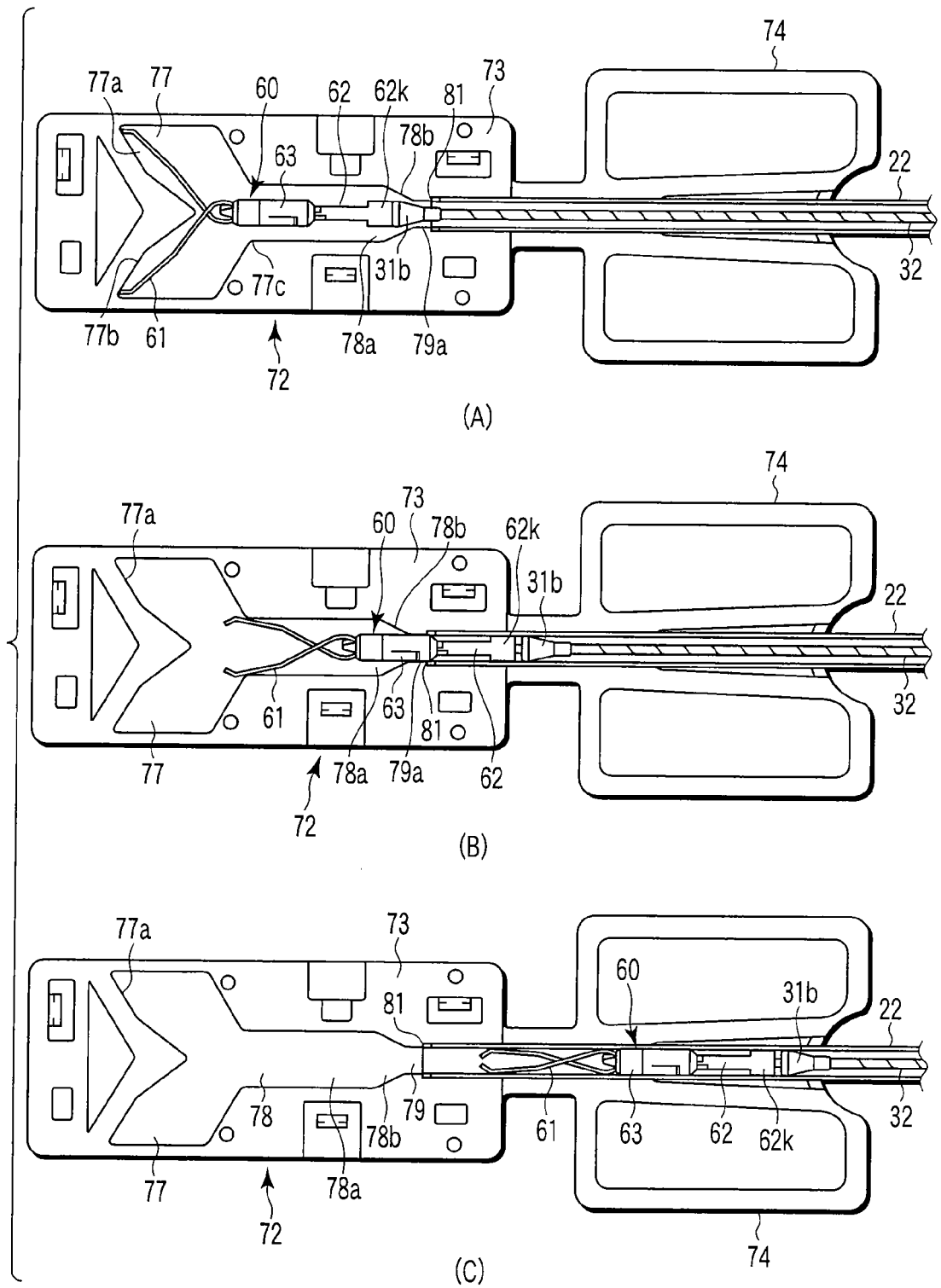
FIG. 19(A) is a schematic plan view showing a state where the clip introduction device is engaged with the clip unit according to the first embodiment.
FIG. 19(B) is a schematic plan view showing how the introduction tube is pulled out from the cartridge in a state where the clip introduction device is engaged with the clip unit according to the first embodiment.
FIG. 19(C) is a schematic plan view showing a state where the clip unit is drawn into the introduction tube when the clip introduction device is engaged with the clip unit according to the first embodiment.
Figure 21:
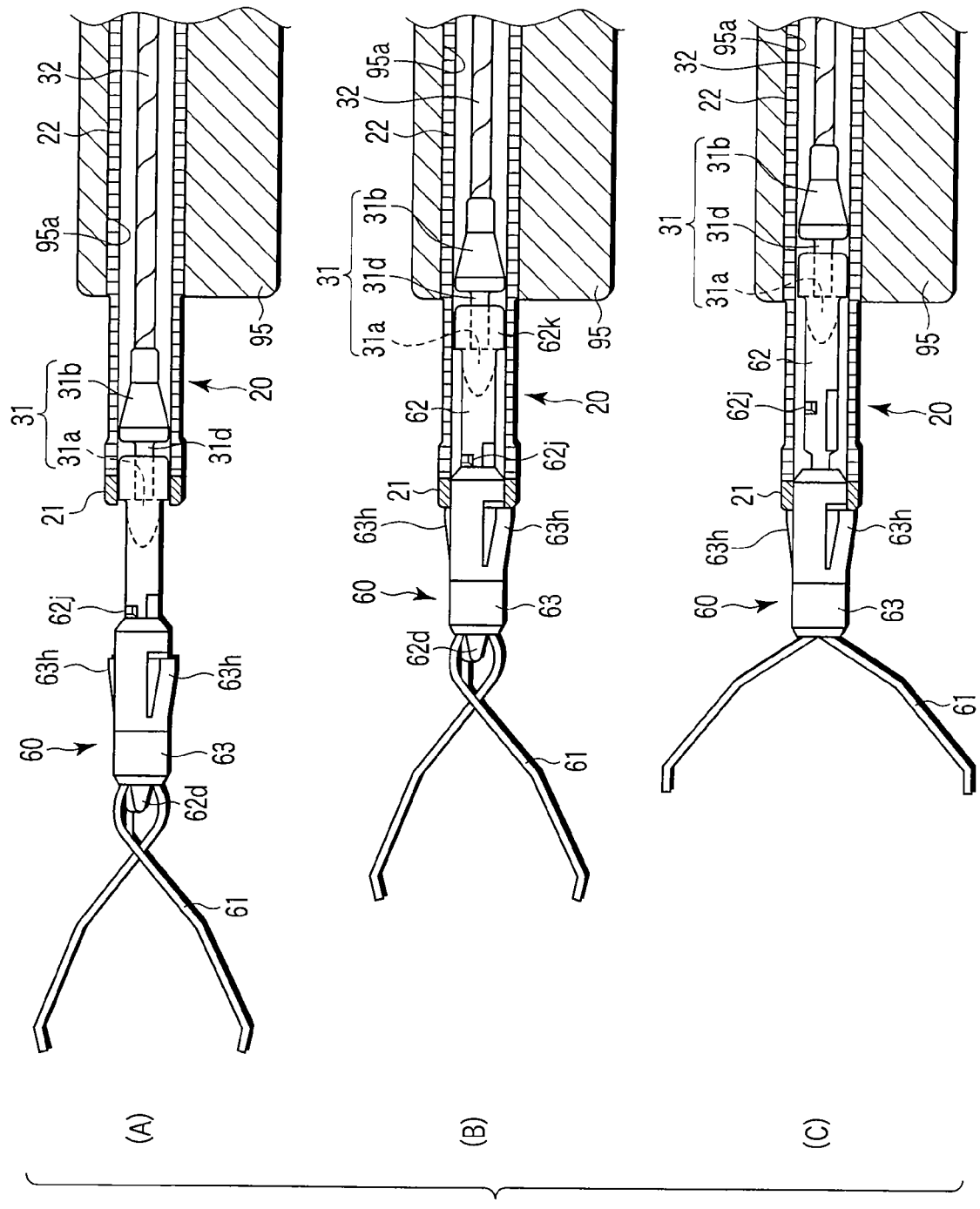
FIG. 21(A) is a schematic partial cross-sectional view showing a state where the clip unit protrudes from the distal end of the introduction tube when the clip introduction device having the clip unit attached therein is being inserted in the forceps channel of the inserting section of the endoscope according to the first embodiment.
FIG. 21(B) is a schematic partial cross-sectional view showing a state where retractable wings of the clip unit are latched at the distal end of the introduction tube when the clip introduction device having the clip unit attached therein is being inserted in the forceps channel of the inserting portion of the clip unit according to the first embodiment.
FIG. 21(C) is a schematic partial cross-sectional view showing a state where the clip is pulled toward the front side of the clip introduction device to open the clip at a maximum when the clip introduction device having the clip unit attached therein is being inserted in the forceps channel of the inserting section of the endoscope and the retractable wings of the clip unit are being latched at the distal end of the introduction tube according to the first embodiment.
Figure 22:
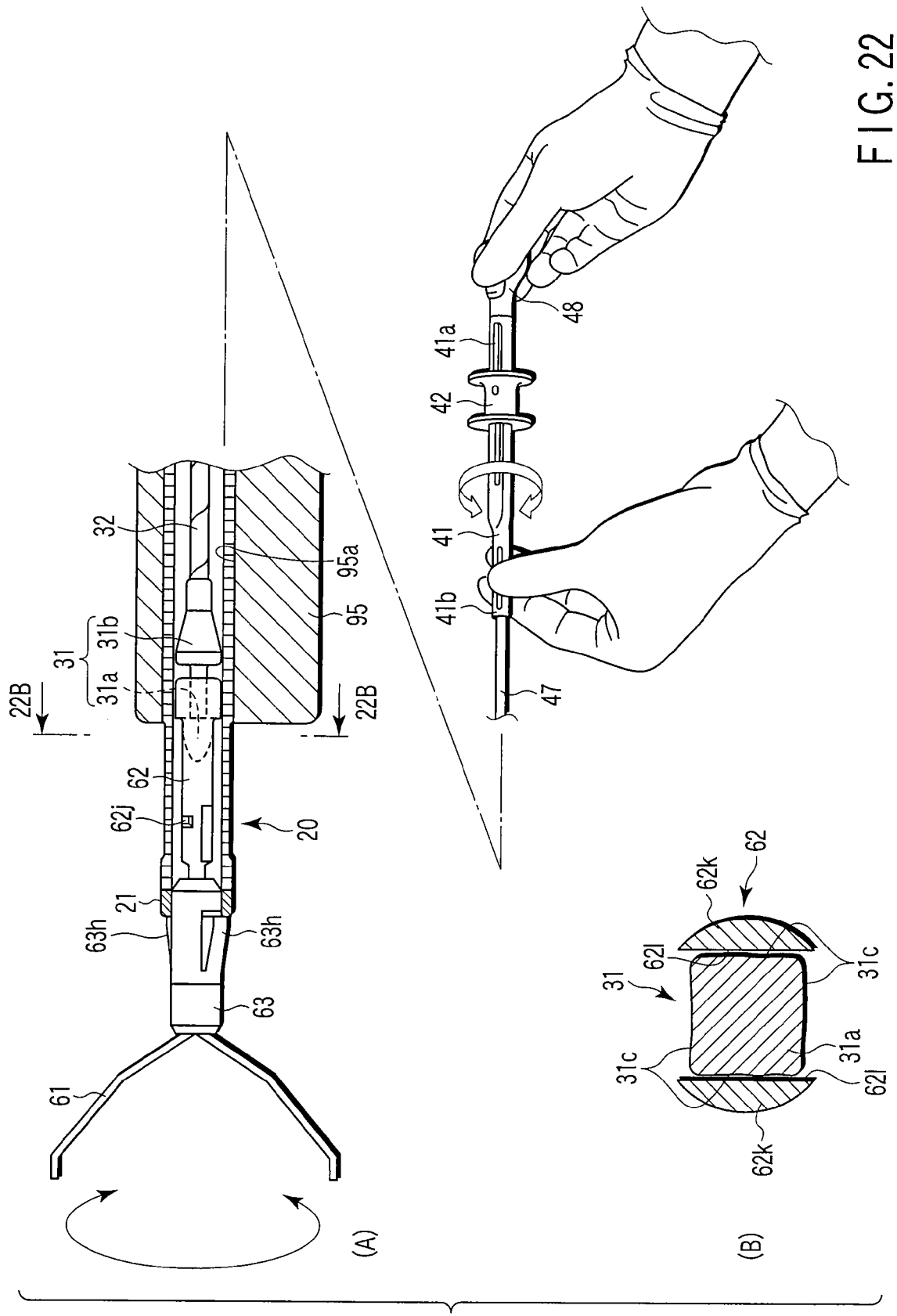
FIG. 22(A) is a schematic partial cross-sectional view showing a state where a rotation grip of an operating portion main body on the front side of the clip introduction device is rotated to turn the clip unit when the clip introduction device having the clip unit arranged therein is being inserted in the forceps channel of the inserting section of the endoscope, the retractable wings of the clip unit are being arranged at the distal end of the introduction tube and the clip is being pulled toward the front side of the clip introduction device to open the clip at a maximum according to the first embodiment.
FIG. 22(B) is a schematic cross-sectional view taken along a line 22B-22B in FIG. 22(A)
Figure 24:
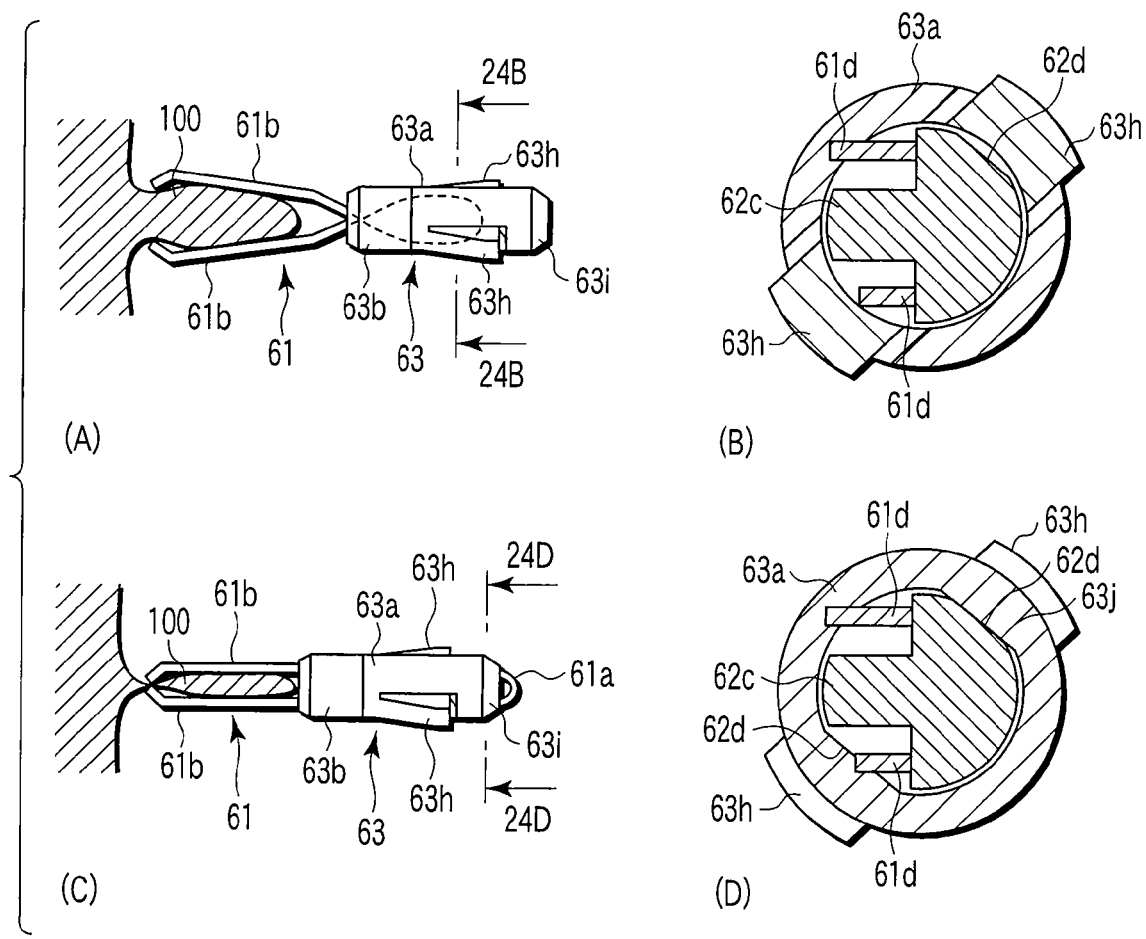
FIG. 24(A) is a schematic side view showing a state where the leg portions of the clip in the clip unit are closed to clip a biomedical tissue which is wide in a vertical direction by the clip according to the first embodiment.
FIG. 24(B) is a cross-sectional view taken along a line 24B-24B in FIG. 24(A)
FIG. 24(C) is a schematic side view showing a state where the leg portions of the clip in the clip unit are closed to clip a biomedical tissue narrow in a width along the vertical direction by the clip according to the first embodiment.
FIG. 24(D) is a cross-sectional view taken along a line 24C-24C in FIG. 24(C)

As shown in FIG. 17, the instruction tube 20 of the clip introduction device 10 is inserted all the way into the introduction tube inserting portion (the coil inserting portion) 80 from the inlet 82 of the compressing portion 74 of the cartridge 70 which is in such a state. As shown in FIG. 18(A), the distal end tip 21 of the introduction tube 20 is brought into contact with the distal end tip contact portion 81.

In this state, as shown in FIG. 17, the compressing portion 74 of the cartridge 70 is pinched and compressed by fingers. At this time, the compressing portion 74 is elastically deformed, and the introduction tube fixing portion 85 thereby holds the distal-end-side coil 22 of the introduction tube 20. Therefore, the introduction tube 20 is fixed in the axial direction.

Then, the slider 42 shown in FIGS. 1 and 2(B) is moved toward the distal end side apart from the thumb ring 48. The operation wire 30 allows the distal end of the clip unit engagement portion 31a of the arrow-head hook portion 31 to protrude with respect to the distal end tip 21 at the distal end of the introduction tube 20.

At this time, as shown in FIG. 18(A), the distal end of the clip unit engagement portion 31a of the hook portion 31 is brought into contact with the tapered portions 62n at the proximal end of the elastic arm portions 62k arranged in the diameter reducing portion 79a. At this time, the elastic arm portions 62k of the coupling member 62 are restricted from moving in a direction perpendicular to the axial direction, i.e., increasing a diameter thereof by the diameter reducing portion 79a. Therefore, the distal end of the clip engagement portion 31a of the hook portion 31 is assuredly brought into contact with the tapered portions 62n formed at the center of the proximal end of the elastic arm portions 62k of the coupling member 62 of the clip unit 60. That is, the clip unit engagement portion 31a of the hook portion 31 is engaged with the tapered portions 62n at the proximal end of the coupling member 62.

Meanwhile, as shown in FIGS. 18(A) and 18(B), in a state where the clip unit 60 is accommodated in the cartridge 70, the proximal end of the elastic arm portions 62k of the coupling member 62 of the clip unit 60 is arranged in the diameter reducing portion 79a which is the minimum diameter portion of the cartridge 70. Since the internal diameter of the diameter reducing portion 79a is substantially equal to the external diameter of the elastic arm portions 62k, there is almost no gap between the outer periphery of the proximal end of the elastic arm portions 62k and the diameter reducing portion 79a. Therefore, the distal end of the clip unit engagement portion 31a of the hook portion 31 can be prevented from deviating from the tapered portions 62n of the elastic arm portions 62k. In particular, this is effective when the distal end of the clip unit engagement portion 31a of the hook portion 31 is bent at the distal end of the shaft portion 31 due to any factor during repeated sterilization and use of the clip introduction device 10.

The clip unit engagement portion 31a of the hook portion 31 is further pushed into the cartridge 70. That is, the hook portion 31 is allowed to further protrude with respect to the distal end tip 21 of the introduction tube 20. At this time, the distal ends of the arms 61b of the clip 61 in the clip unit 60 are opened along the tapered surface 77a at the distal end of the clip accommodating portion 77. That is, the elastic arm portions 62k at the proximal end of the coupling member 62 of the clip unit 60 move toward the distal end side along the axial direction of the clip unit 60. Therefore, the proximal end of the elastic arm portions 62k is moved to a position of a cross section 18C-18C shown in FIGS. 18(A) and 18(C).

As shown in FIG. 19(A), the proximal end of the elastic arm portions 62k is arranged in the elastic arm portion diameter increasing portion 78a. At this time, since the clip 61 of the clip unit 60 is in contact with the end of the tapered surface 77a at the distal end of the clip accommodating portion 77, it is difficult to further move the clip unit 60 toward the distal end side. Since the clip unit 60 is restricted from moving toward the distal end side in this manner, further pushing the clip unit engagement portion 31a of the hook portion 31 with respect to the cartridge 70 allows the elastic arm portions 62k to be expanded from the proximal end side. Therefore, the clip unit engagement portion 31a of the hook portion 31 is inserted into the notch portion 62m between the elastic arm portions 62k.

When this clip unit engagement portion 31a is inserted into the notch portion 62m between the elastic arm portions 62k, the elastic arm portions 62 are closed due to elastic deformation. Therefore, in a state where the engagement portion 31a is arranged in the notch portion 62m of the elastic arm portions 62k, the shaft portion 31d at the proximal end of the engagement portion 31a is held between the elastic arm portions 62k. Therefore, as shown in FIG. 19(A), the hook portion 31 is coupled with the elastic arm portions 62k. That is, the clip unit 60 is coupled with the operation wire 30 of the clip introduction device 10.

It is to be noted that the engagement portion 31a of the hook portion 31 is obliquely inserted into the notch portion 62m between the elastic arm portions 62k in some cases. In such a case, the flat surface portions 62g and 62i of the coupling member 62 (see FIGS. 9(A) and 9(B)) face the parallel surfaces 63l of the pressing tube 63 (see FIG. 10(C)). Moreover, the proximal end of the clip 61 is engaged with the distal end of the coupling member 62. These structures avoid rotation of the clip unit 60. That is, in a state where the clip 61 is opened, a vertical width of the clip accommodating portion 77 is narrow, and the clip 61 cannot be rotated in a periaxial direction. Therefore, the coupling member 62 coupled with the clip 61 cannot be rotated either. Additionally, the since the flat surface portions 62g and 62i of this coupling member 62 face the parallel surfaces 63l of the pressing tube 63, the pressing tube 63 cannot be rotated with respect to the coupling member 62. Therefore, when inserting the engagement portion 31a of the hook portion 31 into the notch portion 62m of the elastic arm portions 62k, the flat surface portions 31c of the hook portion 31 are pressed by the flat surface portions 62l of the notch portion 62m between the elastic arm portions 62k. That is, the engagement portion 31a of the hook portion 31 is pressed by an elastic formed caused when the elastic arm portions 62k are to be closed, and the flat surface portions 31c of this engagement portion 31a are arranged in parallel with the flat surface portions 62l of the notch portion 62m between the elastic arm portions 62k. Then, the hook portion 31 swivels in the notch portion 62m of the elastic arm portions 62k. That is, the flat surface portions 31c of the hook portion 31 are brought into contact with the flat surface portions 62l of the elastic arm portions 62k, and the elastic arm portions 62k are closed while holding the engagement portion 31a of the hook portion 31. Further, restricting rotation of the pressing tube 63 constrains the direction of movement of the retractable wings 63h in the cartridge 70. Therefore, when pulling in the clip 61, the clip 61 can be drawn in a state where the retractable wings 63h do not come into contact with the vertical surface 78d but they face a direction along which they come into contact with the tapered surface 78c.

Subsequently, the clip unit 60 coupled with the clip introduction device 10 is pulled into the introduction tube 20 of the clip introduction device 10 in order to insert the clip unit 60 into a forceps channel 95a (see FIG. 20) of a later-described inserting section 95 of an endoscope.

The slider 42 shown in FIG. 1 is moved toward the proximal end side of the operating portion main body 41. As shown in FIG. 19(B), the clip unit 60 is pulled into the introduction tube 20 via the operation wire 30. At this time, the retractable wings 63h of the pressing tube 63 are pushed in by the tapered surface 78c of the retractable wing accommodating concave portion 78b. That is, the retractable wings 63h are pushed into the pressing tube main body 63a. At this time, the retractable wings 63h are completely pushed into the pressing tube main body 63a by the diameter reducing portion 79a. Therefore, the clip unit 60 is pulled into the introduction tube 20 while the retractable wings 63h are not caught on the end surface of the distal end tip 21 which is in contact with the distal end tip contact portion 81 at the proximal end of the diameter reducing portion 79a. That is, the pressing tube 63 is pulled into the introduction tube 20 together with the proximal end of the coupling member 62.

At this time, as shown in FIG. 19(C), the arms 61b of the clip 61 are closed by the distal end tip 21 and the distal-end-side coil 22 of the introduction tube 20 in accordance with internal diameters of these members. Since the retractable wings 63h of the pressing tube main body 63a are in contact with the inner surface of the introduction tube 20, they are maintained to be accommodated in the pressing tube main body 63*a*.

After the clip unit 60 is pulled into the introduction tube 20 in this manner, when a force of pinching the compressing portions 74 of the cartridge (the clip case) 70 is weakened, the compressing portions 74 are expanded in the vertical direction by a restoring force caused due to elasticity. That is, a space between the compressing portions 74 alone are expanded in the vertical direction with the upper case 71 and the lower case 72 being engaged with each other. Therefore, the introduction tube 20 can be pulled out from the introduction tube inserting portion 80 of the cartridge 70. That is, the introduction tube 20 is separated from the cartridge 70.

At this time, the clip unit 60 is attached to the hook portion 31 at the distal end of the operation wire 30 of the clip introduction device 10. The distal end of the clip 61 of the clip unit 60 is being pulled in with respect to the distal end of the introduction device 20. That is, the clip unit 60 is pulled out from the cartridge 70.

Then, as shown in FIG. 20, the introduction tube 20 of the clip introduction device 10 having the clip unit 60 coupled with the distal end of the operation wire 30 is inserted into the forceps channel 95*a* of the inserting section 95 of the endoscope inserted into a body cavity in advance. The distal end of the introduction tube 20 is allowed to protrude from the distal end of the forceps channel 95*a*, and the distal end of the introduction tube 20 is led to a part close to a target region while observing the body cavity by using the endoscope.

A description will now be given as to an operation of clipping a biomedical tissue by the clip 61 of the clip unit 60 from this state.

The clip unit 60 moves forward in the introduction tube 20 via the operation wire 30 by an operation of pushing out the slider 42 shown in FIGS. 1 and 2(B) toward the distal end side of the operating portion main body 41. At this time, since the external diameter of the distal end tube 63*b* of the pressing tube 63 is tapered so that its diameter is gradually reduced toward the distal end portion to facilitate sliding in the introduction tube 20, the clip unit 20 can smoothly move in the introduction tube 20. This is effective for a curved structure when a curvature radius of the inserting section 95 of the endoscope is small as shown in FIG. 20 in particular.

When the operation wire 30 is further moved forward by operating the slider 42, as shown in FIG. 21(A), the clip unit 60 is protruded with respect to the distal end tip 21 at the distal end of the introduction tube 20. At this time, since the retractable wings 63*h* of the pressing tube 63 are formed on the inclined surfaces with a downward pitch toward the distal end side, the clip unit 60 is smoothly pushed out without resistance. Furthermore, the retractable wings 63*h* of the pressing tube 63 are released from the state of contact with the inner surface of the introduction tube 20, and protrudes in an outer peripheral direction of the pressing tube 63. On the other hand, since the pair of arms 61*b* of the clip 61 have expanding properties, it is opened to some extent simultaneously with protrusion from the introduction tube 20.

At this time, since the coupling member 62 and the pressing tube 63 are formed of resin materials colored into different colors (e.g., the pressing tube main body 63*a* is blue and the coupling member 62 is white), a boundary part between the coupling member 62 and the pressing tube main body 63*a* can be clearly recognized.

Therefore, when the slider 42 is moved toward the distal end side and the clip unit 60 is protruded from the distal end of the introduction tube in the body to allow a protruding state of the retractable wings 63, even if the clip unit 60 is protruded with respect to the introduction tube 20 beyond necessity, it is possible to recognize that the clip unit 60 is excessively protruded before the clip 61 comes into contact with a body cavity wall and engagement between the hook portion 31 and the clip unit 60 is released. Therefore, a boundary between colors (a boundary between the coupling member 62 and the pressing tube main body 63*a*) can be confirmed by using an endoscopic image to check necessary protrusion of the clip unit 60, thereby avoiding excessive protrusion.

Then, the slider 42 is moved toward the proximal end side of the operating portion main body 41. As shown in FIG. 21(B), the operation wire 30 is pulled back to the proximal end side, and the proximal end surfaces of the retractable wings 63*h* of the pressing tube 63 are engaged with the distal end surface of the distal end tip 21 of the introduction tube 20.

As shown in FIG. 21(C), when the slider 42 is further moved toward the proximal end side to pull back the operation wire 30, the loop portion 61*a* of the clip 61 is pulled into the pressing tube 63 through the coupling member 62. Therefore, the clip 61 is further opened. Then, projections 61*d* of the clip 61 come into contact with the internal diameter step portion 63*g* (see FIG. 10(B)) of the pressing tube main body 63*a*, and the arms 61*b* are fully opened.

In this state, the clip introduction device 10 is operated to move the clip 61 closer to a target region while observing the target region of the biomedical tissue by using the endoscope, and the tissue grasping portions 61*c* of the clip 61 are appressed against this region. At this time, a thumb is inserted into the thumb ring 48 of the operating portion 40, and an index finger and a middle fingers are used to hold the slider 42 for the operation. In this state, the thumb ring 48 is rotatable with respect to the operating portion main body 41.

Therefore, as shown in FIG. 22(A), a hand is released from the slider 42. Moreover, the rotation grip 41*b* of the operating portion main body 41 is held by a left hand with the thumb ring 48 being held by a right hand, and the rotation grip 41*b* is rotated in a periaxial direction of the main body 41. Then, the operation wire 30 rotates through each first slide member (the wire accepting pipe presser) 51 and the wire accepting pipe 34. That is, the hook portion 31 rotates. Therefore, as shown in FIG. 22(B), a force is applied to the flat surface portions 62*l* on the inner surface of the notch portion 62*m* of the coupling member 62 in the clip unit 60 by the flat surface portions 31*c* provided on the clip unit engagement portion 31*a* of the hook portion 31. Therefore, the clip unit 60 rotates in a periaxial direction. When rotating the clip unit 60 to change a direction in this manner, the rotation grip 41*b* of the operating portion main body 41 is held to rotate the main body 41, but the operating portion main body 41 can be rotated while keeping the thumb in the thumb ring 48.

In a state where the clip unit 60 is rotated in a desired condition, when the slider 42 is further moved toward the proximal end side, the operation wire 30 moves back, and the arms 61*b* of the clip 61 are pulled into the distal end tube 63*b* of the pressing tube 63 through the coupling member 62. Therefore, the projections 61*d* of the clip 61 climb over the internal diameter step portion 63*g* of the pressing tube 63, and the arms 61*b* of the clip 61 are closed as shown in FIG. 23(A). The biomedical tissue is assuredly held between the arms 61*b* of the clip 61. In this example, the pressing tube main body 63*a* is formed of a resin material which is softer than the clip 61 and has appropriate elasticity. Therefore, the projections 61*d* (see FIG. 8(B)) of the clip 61 bite in the inner wall of the pressing tube main body 63*a*, and the clip 61 is restrained from moving in the pressing tube main body 63*a* along the axial direction and maintained in the closed state. That is, the clip 61 is maintained in a state where the biomedical tissue is held.

The slider 42 is further moved toward the proximal end side from this state to move back the operation wire 30. The narrow diameter portion 62e of the projecting portion 62d is ruptured as a rupture portion of the coupling member 62 of the clip 61 as shown in FIG. 23(B). Therefore, coupling of the clip 61 with respect to the coupling member 62 is released. Therefore, the clip 61 of the clip unit 60 is separated from the clip introduction device 10 to be kept in the body cavity while holding the biomedical tissue. At this time, this clip 61 is fixed to the pressing tube 63.

A function of the flat surface portions 62g and 62i of the coupling member 62 and the oval hole 63j of the pressing tube 63 will now be described.

In a state before the clip 61 shown in FIG. 7 is pulled into the pressing tube 63, each parallel surface 63l of the oval hole 63j of the pressing tube 63 is matched with the flat surface portions 62i of the coupling member 62. Therefore, the pressing tube 63, the coupling member 62 and the clip 61 are prevented from relatively rotating around the longitudinal axis of the clip unit 60. Therefore, shifting is prevented from being generated in a relative position relationship between the sawtooth projections 61d of the clip 61 and the retractable wings (blade portions) 63h of the pressing tube 63. As shown in FIGS. 24(B) and 24(D), the flat surface portions 62g of the coupling member 62 function to avoid shifting of the relative position relationship between the sawtooth projections 61d and the retractable wings 63h when the clip 61 is pulled into the pressing tube 63 like the flat surface portions 62i. As a result, when the clip 61 is pulled into the distal end tube 63b or the pressing tube main body 63a of the pressing tube 63, the sawtooth projections 61d of the clip always stick into the inner wall of the pressing tube main body 63a. Even if the clip 61 is used to clip an object (the biomedical tissue) 100 having any thickness shown in FIGS. 24(A) and 24(B) in order to avoid the retractable wings 63h or the groove around these members in this manner, a clipping force of the clip 61 can be prevented from being alleviated.

After the clip 61 clips the biomedical tissue 100 (see FIGS. 24(A) and 24(C)), i.e., after the clip 61 is kept in the body cavity, the clip introduction device 10 is removed from the forceps channel 95a of the inserting section 95 of the endoscope. In order to reload the clip unit 60, the coupling member 62 is removed from the arrow-head hook portion 31. In this case, when the coupling member 62 is swiveled in an arrow direction along an opening direction of the notch portion 62m with respect to the axial line of the operation wire 30, the arrow-head hook portion 31 can be removed from the notch portion 62m of the coupling member 62. That is, when the shaft portion 31d of the hook portion 31 is removed from the elastic arm portions 62k, engagement between the coupling member 62 of the clip unit 60 and the clip unit engagement portion 31a of the hook portion 31 is released.

Figure 25:
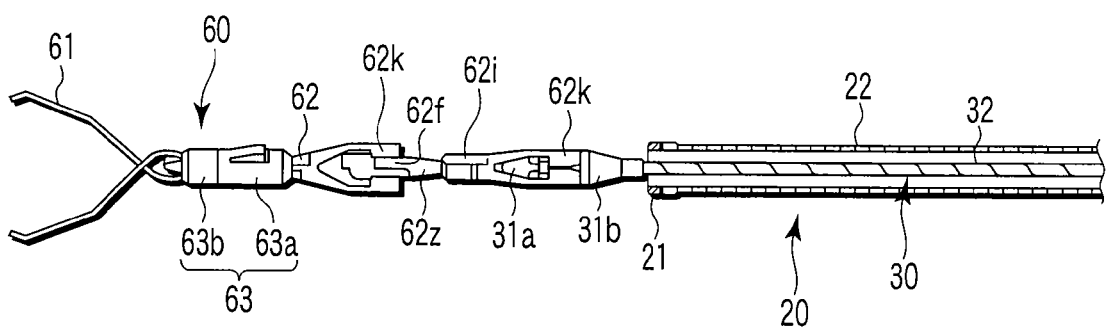
FIG. 25 is a schematic view showing a state where a distal end of a remaining coupling member is inserted into the proximal end of the coupling member of the clip unit when the remaining coupling member is being attached to the hook portion of the clip introduction device according to the first embodiment.
Figure 26:
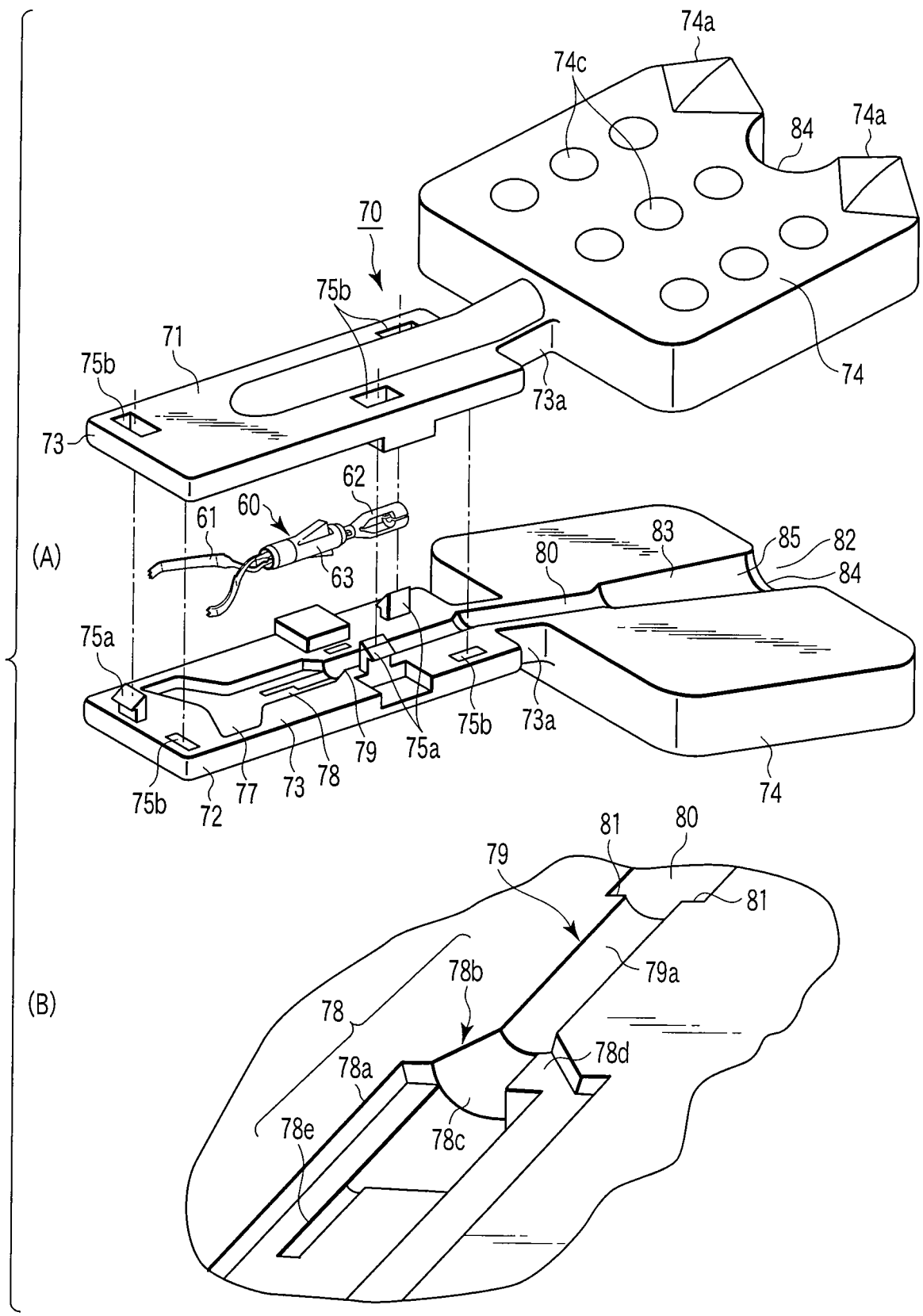
FIG. 26(A) is an exploded perspective view of a cartridge used when loading a clip unit into a clip introduction device according to a second embodiment.
FIG. 26(B) is a schematic perspective view showing a part close to a diameter reducing portion in FIG. 26(A)

Incidentally, after the clip 61 is closed to rupture the coupling member 62, the coupling member 62 remaining in the hook portion 31 (which will be referred to as a remaining coupling member 62z hereinafter) must be removed before attaching the next new clip 61. However, as shown in FIG. 25, there can be considered a possibility that an operation of removing such a remaining coupling member 62z is forgotten and the next clip 61 is attached. For example, when the remaining coupling member 62z is pulled into the introduction tube 20 in a state where the engagement portion 31a of the hook portion 31 is engaged with the remaining coupling member 62z, one may presume that the remaining coupling member 62z has been removed from the hook portion 31 in some cases. Additionally, the introduction tube 20 of the clip introduction device 10 in this state is inserted into the contact portion 81 from the inlet 82 of the cartridge 70 in order to attach the new clip unit 60 to the hook portion 31. Even if the cartridge 70 is formed of a transparent material, the remaining coupling member 62z or the clip unit 60 is very small, and, since the operating room may be dark, visually discriminating the hook portion 31 of the clip introduction device 10 or the remaining coupling member 62z arranged in the cartridge is difficult.

The cone portion 62f (see FIG. 9(A)) is formed in each of the coupling member 62 and the remaining coupling member 62z. The elastic arm portions 62k of the coupling member 62 in the new clip unit 60 are to be engaged in a state where the remaining coupling member 62z is engaged with the hook portion 31 in the clip introduction device 10. In this case, the distal end in which the protruding portion 62c of the remaining coupling member 62z is removed by rupture pushes the proximal ends of the elastic arm portions 62k of the new coupling member 62 toward the distal end side to arrange the elastic arm portions 62k in the elastic arm portion diameter increasing portion 78a. Then, the elastic arm portions 62k of the new coupling member 62 are opened, and the distal end of the remaining coupling member 62z is fitted in the notch portion 62m between the elastic arm portions 62k of the new coupling member 62. At this time, the cone portion 62f of the remaining coupling member 62z is sandwiched by the proximal ends of the elastic arm portions 62k of the new coupling member 62. Since the cone portion 62f of this remaining coupling member 62z is formed into a substantially conical shape, the elastic arm portions 62k may slide with respect to the cone portion 62f even if the elastic arm portions 62k of the coupling member 62 are engaged. That is, if these portions slide, the remaining coupling member 62z can be prevented from being engaged with the coupling member 62 of the new clip unit 60.

Furthermore, even if the clip unit 60 in the cartridge 70 is engaged to be removed to the outside of the cartridge 70 in this state, the proximal end surfaces of the expanded elastic arm portions 62k of the coupling member 62 are caught on the vertical surface 78d (see FIG. 12(B)) provided in the retractable wing accommodating concave portion 78b of the pressing tube accommodating portion 78 of the cartridge 70. Therefore, when the new clip unit 60 is to be removed from the cartridge 70, the coupling member 62 of the new clip unit 60 comes off the remaining coupling member 62z.

Therefore, in any case, in a state where the remaining coupling member 62z is coupled with the hook portion 31, the new clip unit 60 is engaged with the cone portion 62f of the remaining coupling member 62z, thereby preventing the new clip unit 60 from being removed from the cartridge 70. Then, it can be recognized that the remaining coupling member 62z is engaged with the hook portion 31.

A description will now be given as to a function in a connection structure of the proximal-end-side coil 24 and the operating portion 40.

As shown in FIG. 3, the proximal end of the proximal-end-side coil 24 of the introduction tube 20 according to this embodiment is just inserted in the guide pipe 43 but not fixed through an adhesive, welding or the like. The proximal-end-side coil 24 is sandwiched with a slight gap (a backlash) between the front-side end surface of the coil insertion hole 41d of the guide pipe 43 and the bending-stopper acceptor 46 in the axial direction. Therefore, the operating portion 40 and the introduction tube 20 can be mutually rotated without restraint.

Therefore, when the rotation grip 41*b* of the operating portion 40 is rotated around the axis of the main body 41 in order to rotate the clip unit 60, the introduction tube 20 can be prevented from being twisted. Since an excessive reactive force is not generated between the operating portion 40 and the introduction tube 20, a turning force can be efficiently transmitted to the operation wire 30 alone by rotation of the rotation grip 41*b* of the main body 41. Accordingly, rotating the rotation grip 41*b* of the operating portion main body 41 around the axis of the main body 41 can smoothly rotate the clip unit 60 through the operation wire 30 with an excellent response.

Such a function can be applied to not only the clip introduction device 10 but also all instruments which rotate a treatment portion by using the operation wire 30.

A function in a structure of the wire accepting pipe 34 will now be described.

The wire accepting pipe 34 is formed into a flat shape shown in FIG. 4(B) by caulking. On the other hand, the fixing portion 51*j* of the first slide member 51 is formed into a shape corresponding to the flat shape of the wire accepting pipe 34, and presses the flat portion of the wire accepting pipe 34 from, e.g., the vertical direction. Therefore, when the first slide member 51 rotates by the rotating operation, the wire accepting pipe 34 also rotates. Accordingly, a turning force obtained by the rotating operation of the rotation grip 41*b* of the main body 41 can be assuredly transmitted to the operation wire 30 through the fixing portion 51*j* of the first slide member 51 of the slider 42, the wire accepting pipe 34 and the operation pipe 33.

Such a function can be applied to not only the clip introduction device 10 but also all instruments which rotate the treatment portion by using the operation wire 30.

A function of the O-ring 44 will now be described.

As shown in FIG. 3, the O-ring 44 is arranged on an outer periphery of the operation pipe 33 to fasten the operation pipe 33 in an internal diameter direction. The O-ring 44 is soft-fixed to avoid movement with respect to the operation pipe 33 by a force which is approximately equal to an empty weight of the slider 42 or the main body 41. Therefore, even if a finger is unlinked from the slider 42 by a loading operation or a rotating operation of the clip unit 60, the operation pipe 33 is engaged with the main body 41 by a frictional force between the O-ring 44 and the operation pipe 33, thereby preventing the slider 42 from being accidentally moved. Therefore, the clip unit 60 accommodated in the introduction tube 20 or the hook portion 31 can be prevented from accidentally jumping out of the distal end of the introduction tube 20.

In particular, when a finger is placed on the slider 42 at the time of a rotating operation of the rotation grip 41*b*, a tensile force is generated in the operation wire 30, and the retractable wings 63*h* of the pressing tube 63 in the clip unit 60 and the end surface of the distal end tip 21 of the introduction tube 20 are pressed. That is, a strong frictional force is generated between the non-rotating introduction tube 20 and the rotating retractable wings 63*h*. Therefore, the operation wire 30 cannot be readily rotated. That is, the clip unit 60 cannot be smoothly rotated. Therefore, a finger must be unlinked from the slider 42 at the time of the rotating operation of the rotation grip 41*b*, but the O-ring 44 is soft-fixed to restrict movement of the slider 42, and hence the rotation grip 41*b* can rotated at ease.

As shown in FIG. 3, in order to assuredly alleviate the tensile force of the operation wire 30 in the rotating operation of the rotation grip 41*b*, a space (a backlash) which enables the O-ring to move back and forth by approximately 2 mm to 6 mm is provided in the O-ring accommodating portion 43*a* of the guide pipe 43. Therefore, when the slider 42 is disengaged, the tensile force of the wire 32 can be assuredly alleviated (released). That is, the entire operation wire 30 moves toward the distal end side. Therefore, when the slider 42 is disengaged in a state where the proximal ends of the retractable wings 63*h* are in contact with the distal end of the distal end tip 21, contact between the distal end of the distal end tip 21 and the proximal ends of the retractable wings 63*h* is released. That is, a frictional force acting between the distal end of the distal end tip 21 and the proximal ends of the retractable wings 63*h* is reduced or completely eliminated. Then, when the operating portion main body 41 is rotated as shown in FIG. 22(A), the frictional force between the distal end of the distal end tip 21 and the proximal ends of the retractable wings 63*h* does not act, thereby readily rotating the clip unit 60.

Such a function can be applied to not only the clip introduction device 10 but also all instruments which rotate the treatment portion.

A function in a structure of the first slide member 51 of the slider 42 will now be described.

As shown in FIG. 2(B), a length between slit contact surfaces 51*m* and 51*n* of the first slide member 51 is set to be smaller than a length of the entire slider 42. Therefore, the distal end side of the second slide member 52 of the slider 42 can move toward the distal end side beyond the slit portion 41*a* of the main body 41. Accordingly, the entire length of the main body 41 can be reduced while assuring an amount of movement of the slider 42, thereby realizing an improvement in handiness when, e.g., enclosing the clip introduction device 10 in the sterile pack 90.

Such a function can be applied to not only the clip introduction device 10 but also all instruments.

As described above, according to this embodiment, the following effects can be obtained.

Since the diameter reducing portion 79*a* is provided at the proximal end of the clip unit accommodating portion 73 of the cartridge 70, the arm portions 62*k* at the proximal end of the coupling member 62 of the clip unit 60 can be maintained in a closed state with the clip unit 60 being accommodated in the cartridge 70. Therefore, when engaging the clip introduction device 10 with the clip unit 60, the distal end of the engagement portion 31*a* of the hook portion 31 of the operation wire 30 in the clip introduction device 10 can be always brought into contact with predetermined positions (the tapered portions 62*n*) of the arm portions 62*k* at the proximal end of the coupling member 62 of the clip unit 60. That is, when engaging the clip introduction device 10 with the clip unit 60, they can be assuredly and readily positioned with each other.

Further, the tapered surface 77*a* of the clip accommodating portion 77 at the distal end of the clip unit accommodating portion 73 can be opened while sliding the distal ends of the arms 61*b* of the clip 61. That is, the entire clip unit 60 can be readily moved toward the distal end side. Therefore, the arm portions 62*k* of the coupling member 62 can be readily expanded with the coupling member 62 of the clip unit 60 and the clip introduction device 10 being positioned, thereby coupling (engaging) the coupling member 62 with the clip introduction device 10. That is, the clip introduction device 10 and the clip unit 60 can be assuredly coupled in a predetermined state.

Therefore, according to this embodiment, in an endotherapy product in which a male engagement member (the engagement portion 31*a* of the hook portion 31) is pushed into an expanding/closing female engagement member (the elastic arm portions 62*k*) to detachably couple a distal end instrument portion (the clip unit 60) with an introduction device (the clip introduction device 10), just pushing the male engagement member into the female engagement member can assuredly and readily couple these members with each other.

Furthermore, in this embodiment, as shown in FIG. 13(A), the bent portion 77b is formed on the tapered surface 77a in the clip accommodating portion 77 of the cartridge 70. Therefore, when the distal ends of the arms 61b of the clip 61 in the clip unit 60 move along the tapered surface 77a, a sliding resistance of distal ends of the arms 61b can be increased toward the distal end. Moreover, when the distal ends of the arms 61b in the clip 61 move beyond the bent portion 77b, a user can recognize that the arrow-head hook portion 31 of the introduction tube 20 is on the verge of being engaged with the notch portion 62m of the coupling member 62 at the proximal end of the clip unit 60.

An effect of the breaking projections 74a of the cartridge 70 will now be described.

When the cartridge 70 is pushed toward the sterile paper sheet 90a side from the blister 90b side with a strong force, two holes are first opened (see FIG. 15(D)) in the sterile paper sheet 90a by the breaking projections 74a. When a force is further applied, the sterile paper sheet 90a is torn in the vicinity of the inserting portion inlet 82 positioned between the two projections 74a (see FIG. 16), thereby exposing the inlet 82 of the introduction tube inserting portion 80 of the cartridge 70. Therefore, the distal end of the introduction tube 20 of the clip introduction device 10 can be readily brought into contact with the contact portion 81 from the inlet 82 of the introduction tube inserting portion 80 of the cartridge 70 along this introduction tube inserting portion 80. Additionally, since the sterile paper sheet 90a is torn to be ripped down by the two projections 74a (see FIG. 16), the large torn opening 90c from which the cartridge 70 can be exposed can be easily formed with a light force.

Providing the arc surface 84 in the compressing portion 74 of the cartridge 70 having the clip unit 60 accommodated therein is effective to all instruments using the sterile pack 90.

A second embodiment will now be described with reference to FIGS. 26(A) to 28(B). This embodiment is a modification of the first embodiment, and like reference numerals denote members equal to those described in the first embodiment, thereby eliminating the detailed explanation.

As shown in FIG. 26(A), a cartridge 70 includes the clip unit accommodating portion 73 and the compressing portion 74 like the first embodiment. As shown in FIG. 26(B), an elastic arm portion diameter reducing portion 79a of the coupling member accommodating portion 79 of this cartridge 70 is formed to be longer than the elastic arm portion diameter reducing portion 79a in the first embodiment. Therefore, a distal end tip contact portion 81 is formed on a side close to the compressing portion 74 apart from the distal end tip contact portion 81 of the first embodiment.

The pressing tube accommodating portion 78 includes each retractable wing movement concave portion 78e formed at a distal end of an elastic arm portion diameter increasing portion 78a. That is, the retractable wing movement concave portion 78e guides each retractable wing 63h in a protruding state with respect to a pressing tube main body 63a. The elastic arm portion diameter increasing portion 78a is formed to be deeper than the retractable wing movement concave portion 78e in order to expand elastic arm portions 62k when engaging an engagement portion 31a of an arrow-head hook portion 31 with a coupling member 62. Furthermore, a proximal end of the elastic arm portion diameter increasing portion 78a and a distal end of a tapered surface 78c of a retractable wing accommodating concave portion 78b are smoothly formed.

As shown in FIGS. 27(A) and 27(B), an inclined portion 88 which gently varies is formed between a clip accommodating portion 77 and the pressing tube accommodating portion 78. In particular, this inclined portion 88 is formed between the clip accommodating portion 77 and the elastic arm portion diameter increasing portion 78a. In this inclined portion 88, a vertical cross-sectional surface which smoothly change a space between the clip accommodating portion 77 and the pressing tube accommodating portion 78 is formed into a substantially straight gentle slope. It is preferable for an angle of this inclined portion 88 to be not greater than 45 degrees with respect to a surface of the pressing tube accommodating portion 78. Therefore, when a clip unit 60 is moved toward the distal end side of the clip unit accommodating portion 73, a distal end surface of a pressing tube 63 is prevented from being latched at a proximal end of the clip accommodating portion 77. That is, since the inclined portion 88 is formed into a gentle slope, smooth movement is enabled when the clip unit 60 is moved toward the distal end side of the clip unit accommodating portion 73.

On the other hand, as shown in FIG. 28(A) or FIG. 28(B) or in FIG. 18(A) mentioned above, as the clip unit 60, there is one having a small clip 61 or one having a larger clip 61. That is, as a length of each arm 61b of the clip 61, there are various kinds depending on a size of a region in which the clip 61 is latched to perform a hemostatic operation or the like.

Here, a description will be given as to a case where a length of each arm 61b of the clip 61 is shorter than that of each arm 61b explained in conjunction with the first embodiment. That is, as shown in FIG. 28(A), in the clip unit 60 according to this embodiment, the length alone of each arm 61b of the clip 61 is changed with respect to the clip unit 60 (see FIG. 18(A)) explained in the first embodiment. A distance between the distal ends of these arms 61b is formed to be, e.g., approximately 4 mm to 5 mm. That is, shapes of a loop portion 61a, tissue grasping portions 61c at the distal ends of the arms 61b and projections 61d are equal to those in the clip 61 described in the first embodiment.

Other structures in the clip unit 60 are equal to those in the clip unit 60 described in conjunction with the first embodiment. That is, the coupling member 62 and the pressing tube 63 are equal to those described in the first embodiment.

A description will now be given as to an effect when a combination of a clip introduction device 10, the clip unit 60 and the cartridge 70 according to this embodiment is used.

The cartridge 70 is set upright and held. For example, it is set upright and arranged in such a manner that the clip unit accommodating portion 73 (the distal end of the cartridge 70) thereof is placed on the lower side whilst the compressing portion 74 thereof (the proximal end of the cartridge 70) is placed on the upper side. Then, the entire clip unit 60 moves toward the distal end side of the clip unit accommodating portion 73 by the gravity of the clip unit 60. Then, the tissue grasping portions 61c at the distal ends of the arms 61b of the clip 61 are brought into contact with the tapered surface 77a. Although the arms 61c of the clip 61 are slightly opened along the tapered surface 77a by the gravity of the clip unit 60, further opening is avoided by the elastic force of the arms 61b. At this time, elastic arm portions 62k at the proximal end of the coupling member 62 of the clip unit 60 move toward the distal end side of the elastic arm portion diameter reducing portion 79a, but they are arranged in the elastic arm portion diameter reducing portion 79a.

On the other hand, for example, the clip unit accommodating portion 73 (the distal end of the cartridge 70) of the cartridge 70 is set to face the upper side, and the compressing portion 74 (the proximal end of the cartridge 70) of the same is set to face the lower side. Then, as shown in FIG. 28(A), the entire clip unit 60 moves toward the compressing portion 74 side by the gravity of the clip unit 60. In this example, the length of each arm 61b of the clip 61 is formed to be shorter than the length described in conjunction with the first embodiment. Each of these arms 61b is brought into contact with an arm reducing portion (a latch portion) 77c of the clip accommodating portion 77 in the cartridge 70. At this time, although the arms 61b of the clip 61 are slightly closed by the gravity of the clip unit 60, further closing is avoided by the elastic force of the arms 61b. Therefore, one point (a latch point) on the outer side of the arms 61b is brought into contact with the arm reducing portion 77c of the cartridge 70, thereby supporting the clip unit 60. Accordingly, when the cartridge 70 is set upright, the clip unit 60 is hooked on the arm reducing portion 77c of the cartridge 70 by the elastic force of the arms 61b.

Besides, as shown in FIG. 28(A), the proximal end of each retractable wing 63h of the pressing tube 63 of the clip unit 60 may be brought into contact with each retractable wing accommodating concave portion (a latch portion) 78b depending on an elastic force of the arms 61b. Since each of these retractable wings 63h is pressed to be expanded toward the outside, the proximal end of each retractable wing 63h may be latched in the retractable wing accommodating concave portion 78b in some cases. That is, the clip unit 60 is latched by one or both of the arms 61b of the clip 61 and the proximal end of each retractable wing 63h of the pressing tube 63.

At this time, a length between a part (a latch point) of each arm 61b at which each arm 61b of the clip 61 is brought into contact with the arm reducing portion 77c of the clip accommodating portion 77 and the proximal end of the coupling member 62 of the clip 61 is formed to be shorter than a length between the arm reducing portion 77c and the proximal end of the elastic arm portion diameter reducing portion 79a. That is, the proximal end of the coupling member 62 is arranged in the elastic arm portion diameter reducing portion 79a.

When the cartridge 70 is set upright, the proximal end of the coupling member 62 is prevented from jumping out of the introduction tube inserting portion 80. Therefore, a central axis of the clip unit 60 is arranged on substantially the same axis in the cartridge 70.

Moreover, in a state where each retractable wing 63h is in contact with the retractable wing accommodating concave portion 78b, a length between a contact point (a latch point) of the proximal end of each retractable wing 63h of the clip unit and the retractable wing accommodating concave portion 78b of the cartridge 70 and the proximal end of the coupling member 62 as the proximal end of the clip unit 60 is shorter than a length between the contact portion at the proximal end of each retractable wing 63h and the distal end tip contact portion 81. Therefore, the proximal end of the coupling member 62 is prevented from jumping out into the introduction tube inserting portion 80. Therefore, the central axis of the clip unit 60 is always arranged on substantially the same axis in the cartridge 70.

That is, the proximal end of the coupling member 62 of the clip unit 60 usually moves in the coupling member accommodating portion 79 alone when enclosed in the cartridge 70. Therefore, in a state where the clip unit 60 is enclosed in the cartridge 70, the central axis of the clip unit 60 is always arranged on substantially the same axis.

In the state where the clip unit 60 is enclosed in the cartridge 70 in this manner, the introduction tube 20 is inserted through the introduction tube inserting portion 80 of the cartridge 70. The distal end tip 21 of the introduction tube 20 is brought into contact with the distal end tip contact portion 81 of the cartridge 70. From this state, an operating portion 40 of the introduction tube 20 shown in FIG. 1 is operated to move a wire 32 in a direction along which it protrudes with respect to a distal-end-side coil 22. Therefore, the clip unit engagement portion 31a of the arrow-head hook portion 31 protrudes with respect to the distal end tip 21 to come into contact with a tapered portion 62n.

At this time, the central axis of the clip unit 60 is always arranged on substantially the same axis by the coupling member accommodating portion 79. Therefore, in a state where the central axis of the clip unit 60 matches with the central axis of the operation wire 30, the clip unit 60 moves in the cartridge 70 toward the distal end of the clip unit accommodating portion 73. At this time, since the inclined portion 88 as a gentle slop is formed between the clip accommodating portion 77 and the pressing tube accommodating portion 78, the clip 61 of the clip unit 60 smoothly moves to bring the tissue grasping portions 61c at the distal ends of the arms 61b into contact with the tapered surface 77a.

The arms 61b of the clip 61 in the clip unit 60 move while opening along this tapered surface 77a in a state where the tissue grasping portions 61c are in contact with the tapered surface 77a. The proximal end of the coupling member 62 protrudes from the elastic arm portion diameter reducing portion 79a and moves to the elastic arm portion diameter increasing portion 78a. Then, the elastic arm portions 62k at the proximal end of the coupling member 62 opens, and the clip unit engagement portion 31a at the distal end of the operation wire 30 is arranged in the notch portion 62m.

A subsequent function is the same as the function explained in the first embodiment.

As described above, according to this embodiment, the following effects can be obtained.

Since the elastic arm portion diameter reducing portion 79a of the coupling member accommodating portion 79 is formed long, the proximal end of the coupling member 62 of the clip unit 60 can be always arranged in the elastic arm portion diameter increasing portion 79a in the state where the clip unit 60 is enclosed in the cartridge 70. Therefore, the central axis of the clip unit 60 can be constantly maintained on the central axis of the cartridge 70. With such an arrangement, when attaching the arrow-head hook portion 31 of the introduction tube 20 to the clip unit 60, erroneous attachment can be avoided, thereby always facilitating attachment.

Additionally, since the inclined portion 88 is formed between the clip accommodating portion 77 and the pressing tube accommodating portion 78, a step can be eliminated, thus preventing the clip unit 60 from being latched at the proximal end of the clip accommodating portion 77. Therefore, when the clip unit 60 moves toward the distal end side of the clip unit accommodating portion 73 in the cartridge 70, the clip unit 60 can be prevented from being caught by the proximal end of the clip accommodating portion 77.

It is to be noted that the inclined portion 88 has been described as a gentle slope having a substantially straight vertical cross section in this example, but it is possible to allow various slopes, e.g., one having an inflection point at which an upwardly protruding curve varies to a downwardly protruding curve if the clip accommodating portion 77 can be smoothly connected with the pressing tube accommodating portion 78.

A third embodiment will now be described with reference to FIGS. 29(A) and 29(B). This embodiment is a modification of the first and second embodiments, and like reference numerals denote members equal to those in the first and second embodiments or members having the same functions, thereby eliminating the detailed explanation.

Figure 29:
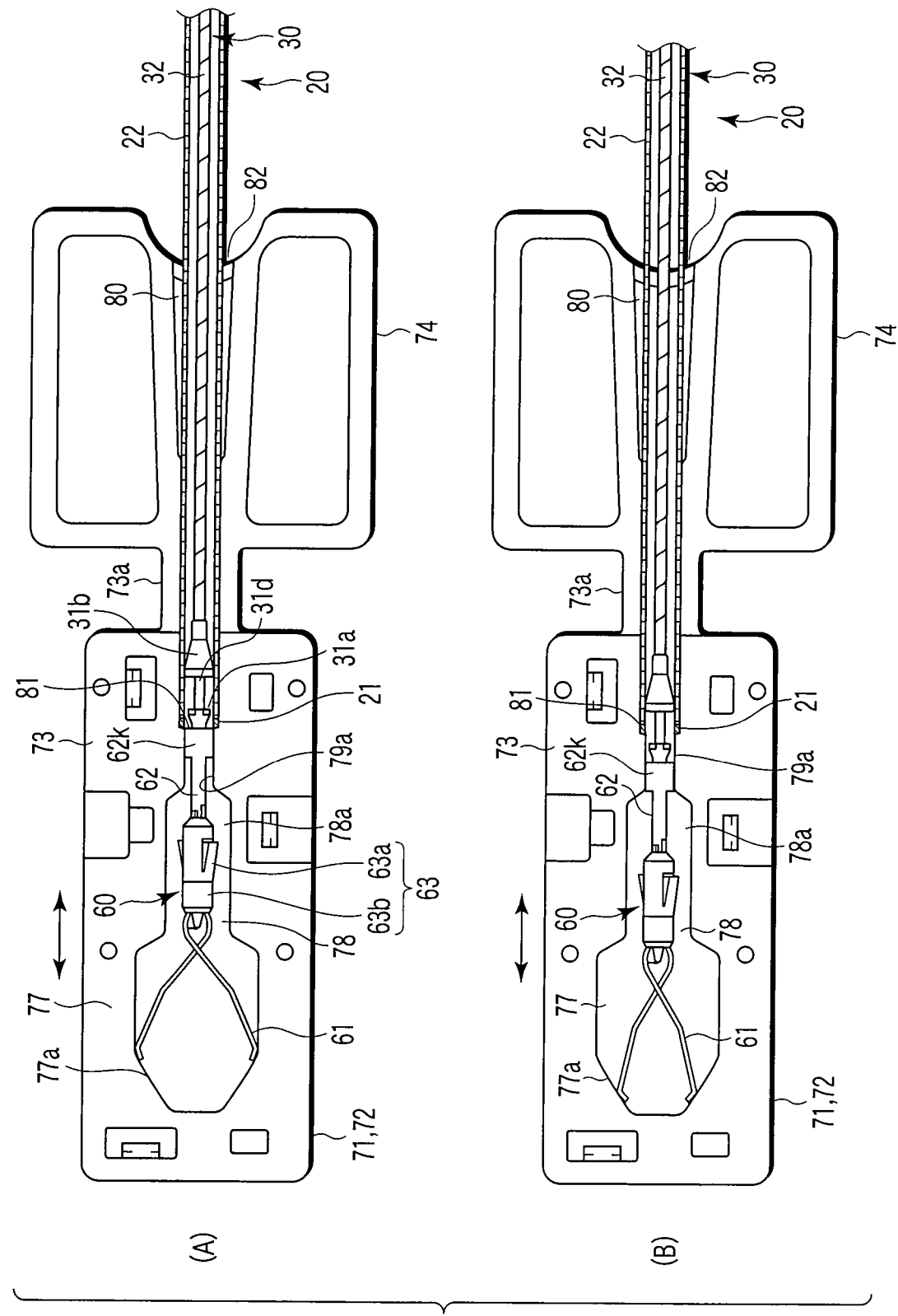
FIG. 29(A) is a schematic plan view showing a state where a distal end of a hook portion of a clip introduction device is brought into contact with an elastic arm portion at a proximal end of a coupling member of a clip unit when a distal end tip of an introduction tube of the clip introduction device is in contact with a distal end tip contact portion of a cartridge according to a third embodiment.
FIG. 29(B) is a schematic plan view showing a state where the distal end of the hook portion of the clip introduction device is brought into contact with the elastic arm portion at the proximal end of the coupling member of the clip unit to move the clip unit to a distal end side of the cartridge when the distal end tip of the introduction tube of the clip introduction device is in contact with the distal end tip contact portion of the cartridge according to the third embodiment.
Figure 33:
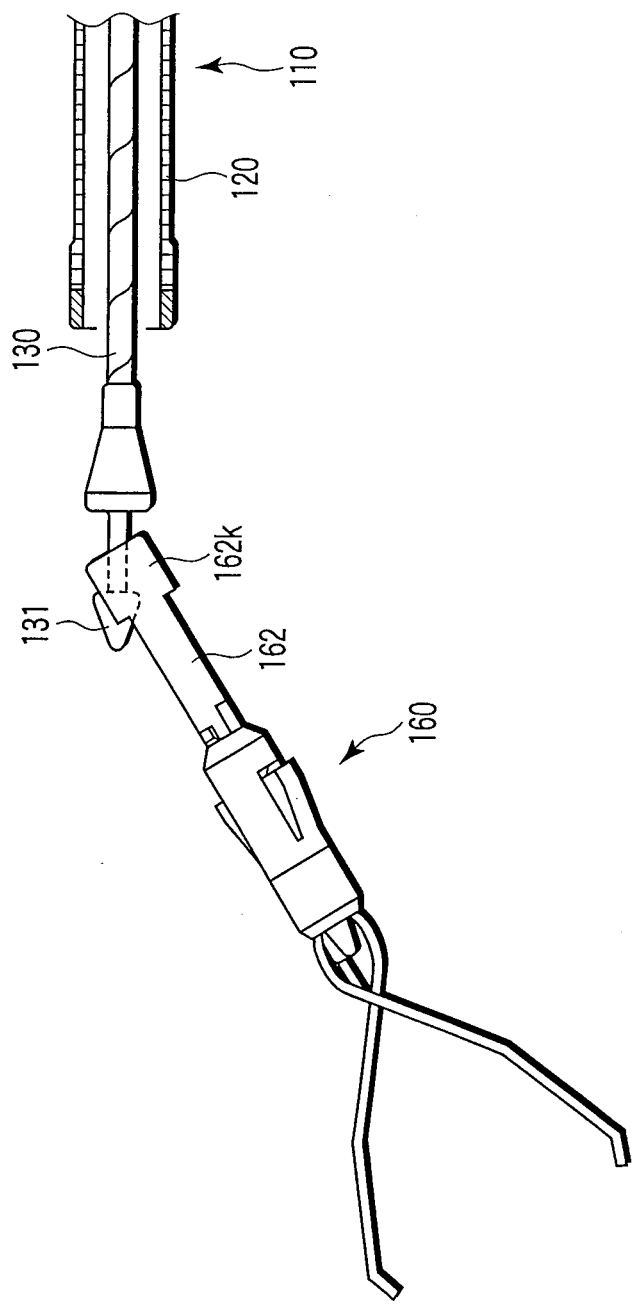
FIG. 33 is a schematic view showing a state where a biomedical tissue is clipped with a coupling member of a clip unit being coupled with a hook portion of a clip introduction device according to the prior art.

As shown in FIGS. 29(A) and 29(B), a tapered surface 77a of a clip accommodating portion 77 in a cartridge 70 according to this embodiment has a shape different from that of the tapered surface 77a described in each of the first and second embodiments. In this embodiment, the tapered surface 77a is formed into a shape which is tapered toward a distal end. That is, the tapered surface 77a includes a clip arm guide portion which guides clip arms in a direction along which an opening amount of the arms 61b of a clip 61 is reduced as a clip unit 60 moves toward a distal end side of a clip unit accommodating portion 73 of the cartridge 70.

A description will now be given as to a function when a combination of a clip introduction device 10, the clip unit 60 and the cartridge 70 according to this embodiment is used.

Like the first and second embodiments, an introduction tube 20 of the clip introduction device 10 is inserted through an inlet 82 of an introduction tube inserting portion 80 of the cartridge 70. A distal end tip 21 at a distal end of the introduction tube 20 is brought into contact with a distal end tip contact portion 81. From this state, an arrow-head hook portion 31 is caused to protrude toward the distal end of the introduction tube 20 to bring the arrow-head hook portion 31 into contact with a tapered portion 62 of the clip unit 60. In this state, elastic arm portions 62k at a proximal end of a coupling member 62 of the clip unit 60 are moved to an elastic arm portion diameter increasing portion 78a.

On the other hand, since the tapered surface 77a at the distal end of the clip accommodating portion 77 in the cartridge 70 is formed into a tapered shape, an amount of opening/closing of the arms 61b of the clip 61 is also reduced along the tapered surface 77a.

Additionally, the arm portions 62k of the coupling member 62 at the proximal end of the clip unit 60 are opened, and the arrow-head hook portion 31 is thereby engaged with a notch portion 62m.

A subsequent function is the same as the function explained in conjunction with the first embodiment.

As described above, according to this embodiment, the following effects can be obtained.

For example, in a case where a length of each arm 61b of the clip 61 is long, when the arms 61b are opened, the clip cannot be sufficiently accommodated with respect to a width of the clip unit accommodating portion 73 of the cartridge 70. In such a case, when the shape described in this embodiment is provided, the same function can be obtained without, e.g., increasing a width of the cartridge 70. Therefore, when accommodating the cartridge 70 including the clip unit 60 in a sterile pack 90 or when enclosing the cartridge 70 in the sterile pack 90 to be accommodated in a box or the like, it is not necessary to create a blister 90b or a box of the sterile pack 90 with a different size, and it is possible to use the sterile pack 90 or the box which is the same as the sterile pack 90 or the box which accommodates the cartridge 70 mentioned in the first and second embodiments.

It is to be noted that the description has been given as to the example where the tapered surface 77a is straightly formed toward the distal end as shown in FIGS. 29(A) and 29(B) in this embodiment, but increasing a sliding resistance for moving the clip 61 toward the distal end, e.g., providing the bent portion 77b explained in the first embodiment (see FIG. 13(A)) is also preferable. With such a structure, a user can recognize that moving beyond the bent portion 77b corresponds to a timing just before the arrow-head hook portion 31 of the introduction tube 20 is engaged with the coupling member 62 at the proximal end of the clip unit 60.

A fourth Embodiment will now be described with reference to FIGS. 30(A) to 30(C).

The treatment device operated by the clip introduction device 10 explained in the first embodiment is not restricted to the clip unit 60. For example, a grasping forceps 96 shown in FIGS. 30(A) and 30(B) can be used. This grasping forceps 96 includes a tissue grasping portion 96a and a coupling member 96b. Since a proximal end of the coupling member 96b has the same structure as the coupling portion 62b of the coupling member 62 described in the first embodiment, thereby eliminating the explanation thereof. In regard to the coupling member 96b, like reference numerals denote parts having the same structures as those in the coupling member 62 described in the first embodiment, thereby eliminating the explanation. A proximal end of the tissue grasping portion 96a is integrally arranged at a distal end of the coupling member 96b. This grasping portion 96a includes a pair of arms 96c and a pair of grasping hands 96d. Proximal ends of the arms 96c are fixed at the distal end of the coupling member 96b. The grasping hands 96d are fixed at the distal ends of the respective arms 96c one by one. These grasping hands 96d are provided with grasping surfaces 96e widely formed for grasping a tissue. It is preferable for these grasping surfaces 96e to be formed into rough surfaces in order to generate a friction between themselves and a biomedical tissue 100.

The pair of arms 96c are formed of an elastic material. Although widths of these arms 96c are narrowed on the proximal end side, i.e., the distal end of the coupling member 96b, the widths are gradually increased toward the distal end side. Therefore, the width of each arm 96c at the distal end thereof is increased and reduced by elastic deformation.

A description will now be given as to a function when this grasping forceps 96 is connected the introduction device (the clip introduction device) 10 to conduct a treatment like the clip unit 60.

Like the example where the clip unit 60 is arranged in the cartridge 70 (see, e.g., FIG. 13(A)) in the first and second embodiments, the grasping forceps 96 is arranged in the cartridge 70 in advance. At this time, the coupling member 96b of the grasping forceps 96 is arranged in a coupling member accommodating portion 79 of the cartridge 70.

Further, a distal end tip 21 of an introduction tube 20 is brought into contact with a contact portion 81 through an introduction tube inserting portion 80 of the cartridge 70. In this state, an engagement portion 31a is caused to protrude with respect to a distal end of the introduction tube 20, and the proximal end of the coupling member 96b is pushed out toward the distal end side of the cartridge 70. Then, the pair of arms 96c of the grasping portion 96a are gradually opened and the coupling member 96b moves to the distal end side. Therefore, the coupling member 96b of the grasping forceps 96 is arranged in an elastic arm portion diameter increasing portion 78a, and the proximal end of the coupling member 96b is engaged with an engagement portion 31a of an operation wire 30.

In this state, a wire 32 of the operation wire 30 is pulled toward an operator's hand side to arrange the grasping forceps 96 in the introduction tube 20. The introduction tube 20 having the proximal end of the grasping forceps 96 being engaged with the engagement portion 31a in this manner is inserted into the forceps channel 95a of the endoscope to be arranged in a body cavity. That is, the distal end of the introduction tube 20 is caused to protrude from a distal end of the forceps channel 95*a*.

The wire 32 of the operation wire 30 is moved to the distal end side so that the grasping forceps 96 protrudes with respect to the distal end of the introduction tube 20. Furthermore, the grasping forceps 96 is rotated to set a direction, and a biomedical tissue is grasped by the grasping surfaces 96*e* of the grasping hands 96*d* of the grasping forceps 96. At this time, the introduction tube 20 is caused to further protrude with respect to the distal end of the forceps channel 95*a*. Then, the coupling member 96*b* of the grasping forceps 96 is relatively pulled into an inner hole of the introduction tube 20, and the pair of arms 96*c* are brought into contact with an inner edge portion at the distal end of the introduction tube 20. Moreover, when the grasping forceps 96 is pulled into the inner hole of the introduction tube 20, the arms 96*c* which are in contact with the inner edge portion at the distal end of the introduction tube 20 are elastically deformed, and these arms are pulled into the inner hole of the introduction tube 20 while being moved closer to each other from the proximal end side toward the distal end side. That is, the pair of arms 96*c* are guided in a closing direction by the distal end of the introduction tube 20. Therefore, the grasping hands 96*d* of the grasping forceps 96 are finally pulled into the inner hole of the introduction tube 20.

It is to be noted that the description has been given as to the example where the grasping surfaces 96*e* are formed on the grasping hands 96*d* in this embodiment, but it is also preferable for each of the grasping hands 96*d* to be formed into a cup-like shape. Additionally, it is preferable that both the grasping hands 96*d* are joined together to be formed into a substantially oval closed state when such cup-like grasping hands 96*d* are arranged in the inner hole of the introduction tube 20.

A fifth embodiment will now be described with reference to FIGS. 31(A) to 31(C). This embodiment is a modification of the first to fourth embodiments.

A treatment device operated by the clip introduction device 10 described in the first and fourth embodiments is not restricted to the clip unit 60 or the grasping forceps 96. For example, an indwelling snare 98 shown in FIGS. 31(A) and 31(B) can be used. This indwelling snare 98 includes a snare portion 98*a*, a stopper 98*b* and a coupling member 98*c*. The snare portion 98*a* formed into a loop shape is fixed at a distal end of the coupling member 98*c*. The stopper 98*b* is arranged on a distal end side of this coupling member 98*c* and at a proximal end of the snare portion 98*a* to be slidable with respect to the snare portion 98*a*. This stopper 98*b* is formed into a substantially columnar shape, and a through hole 98*d* is formed at a central axis thereof. The snare portion 98*a* is inserted into this through hole 98*d*. It is to be noted that an external diameter of this stopper 98*b* is formed to be larger than an internal diameter of a distal end tip 21 of an introduction tube 20 and smaller than an external diameter of the same. Further, the stopper 98*b* is formed of a material such as PTFE having high slidability with respect to an inner wall of the snare portion 98*a* or the forceps channel 95*a*, and it is preferable for each edge portion of an end surface thereof to be chamfered. Therefore, when this stopper 98*b* is brought into contact with a distal end of the distal end tip 21 and inserted into the forceps channel 95*a* of the endoscope together with the introduction tube 20, insertion can be facilitated.

A description will now be given as to a function achieved when this indwelling snare 98 is connected with an introduction device (a clip introduction device) like the clip unit 60 or the grasping forceps 96 to perform a treatment.

Like the first and second embodiments, the indwelling snare 98*a* is arranged in a cartridge having an appropriate shape. This cartridge includes a portion having a diameter allowing at least the stopper 98 to be ejected. Alternatively, the indwelling snare 98 does not have to be necessarily arranged in the cartridge.

An engagement portion 31*a* at a distal end of an operation wire 30 is engaged with a proximal end of the coupling member 98*c* of the indwelling snare 98. In a state where a proximal end of the stopper 98*b* is in contact with a distal end of an introduction tube 20, the coupling member 98*c* is pulled into an inner hole of the introduction tube 20. Furthermore, a wire 32 of the operation wire 30 is pulled toward an operator's hand side to the extent that the snare portion 98*a* is not removed from the stopper 98*b*, thereby arranging the coupling member 98*c* of the indwelling snare 98 in the introduction tube 20. The introduction tube 20 having the proximal end of the indwelling snare 98 being engaged with the engagement portion 31*a* in this manner is inserted into the forceps channel 95*a* of the endoscope to be arranged in a body cavity. At this time, the stopper 98*b* is smaller than an external diameter of the introduction tube 20, and has slidability with respect to an inner wall of the forceps channel 95*a*. Therefore, the distal end of the introduction tube 20 can be caused to protrude from the distal end of the forceps channel 95*a*.

The wire 32 of the operation wire 30 is moved to the distal end side to protrude the snare portion 98*a* and the stopper 98*b* of the indwelling snare 98 with respect to the distal end of the introduction tube 20. Further, the snare portion 98*a* of the indwelling snare 98 is arranged around the biomedical tissue 100. That is, the snare portion 98*a* is hooked on the protruding biomedical tissue 100. Furthermore, the wire 32 is pulled toward the operator's hand side, and the introduction tube 20 is further protruded with respect to the forceps channel 95*a*. Then, in a state where the stopper 98*b* is in contact with the distal end tip 21 of the introduction tube 20, a loop diameter of the snare portion 98*a* fixed to the coupling member 98*c* is narrowed. Therefore, the biomedical tissue 100 is constricted.

Moreover, the indwelling snare 98 is removed from the introduction device 10 in a state where the biomedical tissue 100 is constricted by the snare portion 98*a*. Specifically, the introduction tube 20 is pulled in with respect to the operation wire 30 without moving the operation wire 30 as much as possible. Then, the coupling member 98*c* of the indwelling snare 98 protrudes with respect to the distal end of the introduction tube 20. In this state, the entire introduction device 10 is pulled toward the operator's hand side. Then, the elastic arm portions 62*k* of the coupling member 98*c* of the indwelling snare 98 cannot resist a tensile force, and are opened by an elastic force. Therefore, engagement between the operation wire 30 and the indwelling snare 98 is released, and the indwelling snare 98 indwells with the biomedical tissue 100 being constricted.

It is to be noted that the endo-therapy product is not restricted to the clip unit 60, the grasping forceps 96 and the indwelling snare 98, and it can be modified in many ways.

Although the above has specifically described several embodiments with reference to the drawings, the present invention is not restricted to the foregoing embodiments, and includes all embodiments which are carried out without departing from the scope of the invention.

According to the above description, the inventions in the following notes can be obtained. Additionally, the respective notes can be combined.

[Additional Notes]

(Additional Note 1) A treatment device for an endoscope in which a distal end treatment portion is coupled with an operation device by a female engagement member which can be elastically expanded/contracted and a male engagement member which is coupled with the female engagement member by a push-in operation, the treatment device having an aiding member which aids coupling capable of shifting from a state where the female engagement member and the male engagement member are aligned along an axis of a push-in direction to a state where the female engagement member is expanded/contracted to be coupled with the male engagement member by the push-in operation.

(Additional Note 2) An endo-therapy product system comprising:

an operation device having a hook which detachably engages a distal end treatment portion;

a distal end treatment portion having at least two engagement arms which grasp the hook, the engagement arms being capable of pushing in the hook to be coupled; and a cartridge which includes the distal end treatment portion, the cartridge shifting from a state where the engagement arms surrounding an external diameter and the hook are aligned along a push-in axis to a state where the external diameter is increased to allow expansion/contraction of the engagement arms and coupling of the treatment portion and the hook by a push-in operation.

(Additional Note 3) An endo-therapy product system according to Additional Note 2, wherein the distal end treatment portion is a clip.

(Additional Note 4)

A cartridge (70) having a narrow diameter portion (an elastic arm portion diameter reducing portion 79*a*), comprising:

a clip main body latch portion (a clip arm reducing portion 77*c*, a retractable wing accommodating concave portion 78*b*) which is provided to the cartridge and prevents a clip main body from moving to an operator's hand side;

a latch point (a clip arm 61*b*, a retractable wing 63*h*) which avoids movement of the clip main body which is in contact with the clip main body latch portion, and is provided to the clip main body; and a narrow diameter portion proximal end which is provided in such a manner that a distance from the latch portion to the narrow diameter portion proximal end becomes longer than a distance from the latch point to a proximal end of the clip main body.

(Additional Note 5)

A cartridge (70) comprising:

an arm opening/closing allowing portion (a clip accommodating portion 77) which allows opening/closing of clip arms of a clip;

an accommodating portion (a pressing tube accommodating portion 78) provided at a proximal end of the allowing portion;

a diameter increasing portion (an elastic arm portion diameter increasing portion 78*a*) provided at a proximal end of the accommodating portion; and a shifting portion (an inclined surface portion 88) which is provided between the accommodating portion and the diameter increasing portion and smoothly connects the accommodating portion with the diameter increasing portion.

(Additional Note 6)

The cartridge (70) according to Additional Note 5, wherein a width of the arm opening/closing allowing portion is narrowed toward a distal end side.

(Additional Note 7)

A clip system comprising:

a clip unit (60); and an applicator (10) which has a sheath (20) capable of accommodating the clip unit therein, and can release connection between a clip and a coupling member by rupture the clip unit (60) comprising:

a clip (61);

a coupling member (62) connected with a proximal end of the clip;

a cylindrical fastening member (63) which is coupled with the proximal end of the clip and covers a part of the coupling member, the clip indwelling on a body wall when connection between the coupling member and the clip is released by rupture, wherein the coupling member includes a coupling preventing portion (62*f*) which prevents attachment of a coupling member of another clip unit in a state where the coupling member is attached to the applicator.

(Additional Note 8)

A clip system comprising:

a clip unit (60); and a clip main body indwelling applicator (10) capable of rupturing a space between a clip main body and a coupling member of the clip unit, the clip unit (60) having:

a clip main body (61, 63) attached to a body wall; and a coupling member (62) which is connected with a proximal end of the clip main body, and disconnected from the clip main body by rupture, the clip main body indwelling applicator (10) having:

a sheath (20) capable of accommodating the clip unit therein;

a wire member (30) which has an engagement portion (31) detachable with respect to a proximal end of the coupling member of the clip unit and a wire (32) connected with a proximal end of the engagement portion, and is inserted into the sheath, wherein the coupling member includes at a distal end thereof engagement preventing means (62*f*) for preventing engagement with a proximal end of a coupling member of another clip unit.

(Additional Note 9)

The clip system according to Additional Note 8, wherein the coupling member (62) comprises at a proximal end thereof a pair of engagement arms (62*k*) which are pressed in a closing direction and can be opened/closed, and the engagement preventing means (62*f*) has a lateral cross section formed into a circular shape in such a manner that the engagement arms slide in an engaged state.

(Additional Note 10)

A clip unit comprising:

a clip (61) which has a pair of clip arms (61*b*) and indwells on a body wall when these clip arms are closed;

a cylindrical fastening member (63) which is provided at a proximal end of the clip and adjusts opening/closing of the clip arms; and a coupling member (62) which is connected with the proximal end of the clip, arranged on an inner side of the fastening member, and disconnected from the clip by rupture, wherein the coupling member includes a flat surface portion (62*g*, 62*i*) on at least a part thereof, and the fastening member includes a flat surface portion (63*l*) which avoids rotation of the coupling member with respect to the fastening member at a position facing the flat surface portion of the coupling member on an inner peripheral surface thereof.

(Additional Note 11)

A protection case (70) which accommodates a treatment device (60) therein and is arranged in a sterile pack in a sterile condition, having:
  a breaking projection (74a) which breaks the sterile pack.

(Additional Note 12)

A protection case (70) which accommodates a treatment device (60) therein and is arranged in a sterile pack (90) in a sterile condition, comprising:
  a pair of breaking projections (74a) formed on one side surface to break the sterile pack; and
  an insertion opening (82) of an applicator (10) which is provided between the one side surface and the other side surface on a central line connecting apexes of the breaking projections, and from which the treatment device is taken out from the inside of the protection case.

What is claimed is:

1. An endo-therapy product system comprising:
   an introduction device including a tubular body configured to be inserted into a channel of an endoscope, a wire inserted to be movable along an axial direction of the tubular body, and a connecting portion configured to be arranged at a distal end of the wire and retractable with respect to a distal end of the tubular body by movement of the wire;
   a treatment device including a coupling member having an engagement portion configured to be engaged with the connecting portion at a proximal end, and a treatment device-main body configured to be detachably provided at a distal end of the coupling member; and
   a cartridge including a treatment device-accommodating portion in which the treatment device is accommodated and being used when engaging the connecting portion with the engagement portion;
   wherein
   the treatment device-accommodating portion includes:
   a central axis;
   a coupling member-accommodating portion in which the coupling member of the treatment device is arranged and
   a treatment device-main body-accommodating portion in which the treatment device-main body is configured to be arranged on the central axis of the treatment device-accommodating portion and the treatment device-main body-accommodating portion comprises at a distal end thereof an inclined surface with respect to the central axis of the treatment device-accommodating portion and with respect to an orthogonal direction of the central axis on which a distal end of the treatment device main body is slidable in a contact state.

2. The endo-therapy product system according to claim 1, wherein the treatment device-main body includes a pair of openable/closable arms.

3. The endo-therapy product system according to claim 2, wherein the treatment device-main body has a substantially Y-shape.

4. The endo-therapy product system according to claim 2, wherein the inclined surface includes a pair of tapered surfaces on which distal ends of the arms are slidable, respectively.

5. The endo-therapy product system according to claim 1, wherein the cartridge includes opposed cases respectively containing the treatment device-main body-accommodating portion communicating with each other.

6. A cartridge configured to accommodate a treatment device including a coupling member with an engagement portion at a proximal end and a treatment device-main body provided at a distal end of the coupling member, the cartridge comprising a treatment device-accommodating portion configured to accommodate the treatment device;
   wherein the treatment device-accommodating portion includes:
   a central axis;
   a coupling member-accommodating portion arranged on the central axis of the treatment device-accommodating portion and provided at a proximal end of the treatment device-accommodating portion, in which the coupling member of the treatment device is arranged; and
   a treatment device-main body-accommodating portion arranged on the central axis of the treatment device-accommodating portion and arranged to a distal end side of the coupling member-accommodating portion and on which the treatment device-main body is arranged, the treatment device-main body-accommodating portion includes at a distal end thereof an inclined surface which is inclined with respect to the central axis of the treatment device-accommodating portion and with respect to an orthogonal direction of the central axis on which a distal end of the treatment device-main body is slidable in a contact state.

7. The cartridge according to claim 6, wherein
   the treatment device-main body includes a pair of openable/closable arms, and
   the inclined surface includes a pair of tapered surfaces on which distal ends of the arms are slidable, respectively.

8. The cartridge according to claim 6, further comprising opposed cases respectively including the treatment device-accommodating portion communicating with each other.

9. The cartridge according to claim 6, wherein, at least a proximal end of the coupling member is arranged to be movable in the coupling member-accommodating portion when the treatment device is freely movable in the treatment device-main body-accommodating portion and the coupling member-accommodating portion.

10. The cartridge according to claim 6, wherein
    the treatment device-main body-accommodating portion includes a latch point at which the treatment device-main body is brought into contact with a part of the treatment device-main body-accommodating portion to be latched when the treatment device-main body moves toward a side of a proximal end of the treatment device-main body-accommodating portion, and
    a length between the latch point and the proximal end of the coupling member is shorter than a length between the latch point and the proximal end of the coupling member-accommodating portion.

11. The cartridge according claim 6, wherein the distal end of the treatment device-main body-accommodating portion includes a substantially Y-shape.

12. A cartridge comprising:
    a treatment device including a coupling member with an engagement portion at a proximal end and a treatment device-main body provided at a distal end of the coupling member; and
    a treatment device-accommodating portion accommodating the treatment device;

wherein the treatment device-accommodating portion comprises:

a central axis;

a coupling member-accommodating portion arranged on the central axis of the treatment device-accommodating portion and provided at a proximal end of the treatment device-accommodating portion, in which the coupling member of the treatment device is arranged; and a treatment device-main body-accommodating portion arranged on the central axis of the treatment device-accommodating portion and arranged to a distal end side of the coupling member-accommodating portion and on which the treatment device main body is arranged, the treatment device-main body-accommodating portion includes at a distal end thereof an inclined surface which is inclined with respect to the central axis of the treatment device-accommodating portion and with respect to an orthogonal direction of the central axis on which a distal end of the treatment device main body is slidable in a contact state.

13. The cartridge according to claim 12, further comprising opposed cases respectively including the treatment device-accommodating portion communicating with each other.

14. The cartridge according to claim 12, wherein, at least a proximal end of the coupling member is arranged to be movable in the coupling member-accommodating portion when the treatment device is freely movable in the treatment device-main body-accommodating portion and the coupling member-accommodating portion.

15. The cartridge according to claim 12, wherein the treatment device-main body includes a pair of openable/closable arms.

16. The cartridge according to claim 12, wherein the distal end of the treatment device main body accommodating portion includes a substantially Y-shape.

17. The cartridge according to claim 12, wherein the treatment device-main body includes a pair of openable/closable arms, the treatment device-main body-accommodating portion includes a latch point at which the treatment device-main body is brought into contact with a part of the treatment device-main body-accommodating portion to be latched when the treatment device main body moves toward a side of a proximal end of the treatment device-main body-accommodating portion, and a length between the latch point and the proximal end of the coupling member is shorter than a length between the latch point and the proximal end of the coupling member-accommodating portion.

* * * * *